(12) United States Patent
Rodino-Klapac et al.

(10) Patent No.: US 11,406,717 B2
(45) Date of Patent: *Aug. 9, 2022

(54) ADENO-ASSOCIATED VIRUS VECTOR DELIVERY OF MICRORNA-29 AND MICRO-DYSTROPHIN TO TREAT MUSCULAR DYSTROPHY

(71) Applicant: RESEARCH INSTITUTE AT NATIONWIDE CHILDREN'S HOSPITAL, Columbus, OH (US)

(72) Inventors: Louise Rodino-Klapac, E. Groveport, OH (US); Jerry R. Mendell, Columbus, OH (US); Kristin N. Heller, Columbus, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 301 days.

This patent is subject to a terminal disclaimer.

(21) Appl. No.: 16/092,706

(22) PCT Filed: Apr. 14, 2017

(86) PCT No.: PCT/US2017/027635
§ 371 (c)(1),
(2) Date: Oct. 10, 2018

(87) PCT Pub. No.: WO2017/181014
PCT Pub. Date: Oct. 19, 2017

(65) Prior Publication Data
US 2019/0060489 A1    Feb. 28, 2019

Related U.S. Application Data

(60) Provisional application No. 62/473,253, filed on Mar. 17, 2017, provisional application No. 62/323,163, filed on Apr. 15, 2016.

(51) Int. Cl.
| | | |
|---|---|---|
| C07H 21/04 | (2006.01) |
| A61K 48/00 | (2006.01) |
| C07K 14/47 | (2006.01) |
| A61K 38/17 | (2006.01) |
| A61K 31/7088 | (2006.01) |
| C12N 15/11 | (2006.01) |
| C12N 15/113 | (2010.01) |
| C12N 15/86 | (2006.01) |
| A61P 21/00 | (2006.01) |
| A61K 9/00 | (2006.01) |
| A61P 19/04 | (2006.01) |
| A61K 35/761 | (2015.01) |
| C12N 15/864 | (2006.01) |

(52) U.S. Cl.
CPC .......... *A61K 48/005* (2013.01); *A61K 9/0019* (2013.01); *A61K 31/7088* (2013.01); *A61K 35/761* (2013.01); *A61K 38/1709* (2013.01); *A61K 38/1719* (2013.01); *A61K 48/0058* (2013.01); *A61K 48/0075* (2013.01); *A61P 19/04* (2018.01); *A61P 21/00* (2018.01); *C07K 14/4708* (2013.01); *C12N 15/111* (2013.01); *C12N 15/113* (2013.01); *C12N 15/86* (2013.01); *C12N 15/8645* (2013.01); *C12N 2310/141* (2013.01); *C12N 2320/31* (2013.01); *C12N 2330/51* (2013.01); *C12N 2750/14141* (2013.01); *C12N 2750/14143* (2013.01); *C12N 2800/22* (2013.01); *C12N 2830/008* (2013.01)

(58) Field of Classification Search
None
See application file for complete search history.

(56) References Cited

U.S. PATENT DOCUMENTS

| | | |
|---|---|---|
| 5,173,414 A | 12/1992 | Lebkowski et al. |
| 5,658,776 A | 8/1997 | Flotte et al. |
| 5,786,211 A | 7/1998 | Johnson |
| 5,871,982 A | 2/1999 | Wilson et al. |
| 6,258,595 B1 | 7/2001 | Gao et al. |
| 6,310,196 B1 | 10/2001 | Ricigliano et al. |
| 6,566,118 B1 | 5/2003 | Atkinson et al. |
| 6,869,777 B2 | 3/2005 | Chamberlain et al. |
| 7,001,761 B2 | 2/2006 | Xiao |
| 7,282,199 B2 | 10/2007 | Gao et al. |

(Continued)

FOREIGN PATENT DOCUMENTS

| | | |
|---|---|---|
| CA | 2985000 A1 | 11/2016 |
| CO | 2018012084 A2 | 2/2019 |

(Continued)

OTHER PUBLICATIONS

Naso, Michael F., et al. "Adeno-associated virus (AAV) as a vector for gene therapy." BioDrugs 31.4 (2017): 317-334.*

Ambros, MicroRNA pathways in flies and worms: growth, death, fat, stress, and timing, *Cell.* 113:673-6 (2003).

Cacchiarelli et al., MicroRNAs involved in molecular circuitries relevant for the Duchenne muscular dystrophy pathogenesis are controlled by the dystrophin/nNOS pathway, *Cell Metab.* 12:341-51 (2010).

Carnwath et al., Muscular dystrophy in the mdx mouse: histopathology of the soleus and extensor digitorum longus muscles, *J. Neurol. Sci.* 80:39-54 (1987).

(Continued)

*Primary Examiner* — Kimberly Chong
(74) *Attorney, Agent, or Firm* — Marshall, Gerstein & Borun LLP

(57) ABSTRACT

The invention provides for recombinant AAV vectors comprising a polynucleotide sequence comprising the guide strand of miR-29c and methods of using the recombinant vectors to reduce or prevent fibrosis in subjects suffering from dystrophinopathy or muscular dystrophy. The invention also provides for combination therapies comprising expressing both miR-29 and micro-dystrophin to reduce and prevent fibrosis in patients suffering from dystrophinopathy or muscular dystrophy.

9 Claims, 33 Drawing Sheets
Specification includes a Sequence Listing.

(56) References Cited

U.S. PATENT DOCUMENTS

| | | | |
|---|---|---|---|
| 7,790,449 | B2 | 9/2010 | Gao et al. |
| 10,166,272 | B2 | 1/2019 | Dickson et al. |
| 2008/0044393 | A1 | 2/2008 | White et al. |
| 2008/0249052 | A1 | 10/2008 | Duan et al. |
| 2010/0003218 | A1 | 1/2010 | Duan et al. |
| 2010/0184209 | A1 | 7/2010 | Vermeulen et al. |
| 2014/0234255 | A1 | 8/2014 | Lai et al. |
| 2014/0256802 | A1 | 9/2014 | Boye et al. |
| 2015/0368647 | A1 | 12/2015 | Croce et al. |
| 2016/0317680 | A1 | 11/2016 | Liu et al. |
| 2017/0088837 | A1 | 3/2017 | Singer et al. |
| 2018/0250423 | A1 | 9/2018 | Martin |
| 2019/0117795 | A1 | 4/2019 | Rodino-Klapac et al. |
| 2019/0167762 | A1 | 6/2019 | Dickson et al. |

FOREIGN PATENT DOCUMENTS

| | | |
|---|---|---|
| CO | 2019000395 A2 | 4/2019 |
| CO | 2021000227 A2 | 1/2021 |
| JP | 11-512297 A | 10/1999 |
| JP | 11-318467 A | 11/1999 |
| JP | 2010-535247 A | 11/2010 |
| JP | 2014-198728 A | 10/2014 |
| WO | WO-1995/13365 A1 | 5/1995 |
| WO | WO-1995/13392 | 5/1995 |
| WO | WO-1996/17947 A1 | 6/1996 |
| WO | WO-1997/06243 A1 | 2/1997 |
| WO | 1997/11190 A2 | 3/1997 |
| WO | WO-1997/08298 A1 | 3/1997 |
| WO | WO-1997/09441 A2 | 3/1997 |
| WO | WO-1997/21825 A1 | 6/1997 |
| WO | WO-1998/09657 A2 | 3/1998 |
| WO | WO-1999/11764 A2 | 3/1999 |
| WO | WO-2001/83692 A2 | 11/2001 |
| WO | 2002/06495 A2 | 1/2002 |
| WO | WO-2002/053703 A2 | 7/2002 |
| WO | 2008/088895 A2 | 7/2008 |
| WO | 2009/018493 A1 | 2/2009 |
| WO | WO-2010/071454 A1 | 6/2010 |
| WO | WO-2013/016352 A1 | 1/2013 |
| WO | 2013/078316 A1 | 5/2013 |
| WO | 2013/102904 A1 | 7/2013 |
| WO | WO-2015/107340 A1 | 7/2015 |
| WO | WO-2015110449 A1 | 7/2015 |
| WO | WO-2015/161255 | 10/2015 |
| WO | WO-2015/197232 | 12/2015 |
| WO | WO-2015/197869 A1 | 12/2015 |
| WO | 2016/115543 A2 | 7/2016 |
| WO | 2016/177911 A1 | 11/2016 |
| WO | WO-2017/165859 A1 | 9/2017 |
| WO | 2017/181011 A1 | 10/2017 |
| WO | 2017/181015 A1 | 10/2017 |
| WO | WO-2017/181014 A1 | 10/2017 |
| WO | 2017/221145 A1 | 12/2017 |
| WO | 2019/245973 A1 | 12/2019 |

OTHER PUBLICATIONS

Chao et al., Several log increase in therapeutic transgene delivery by distinct adeno-associated viral serotype vectors, *Mol. Ther.* 2:619-23 (2000).

Chao et al., Sustained and complete phenotype correction of hemophilia B mice following intramuscular injection of AAV1 serotype vectors, *Mol. Ther.* 4:217-22 (2001).

Clark et al., Recombinant adeno-associated viral vectors mediate long-term transgene expression in muscle, *Hum. Gene. Ther.* 8:659-69 (1997).

Coulton et al., The mdx mouse skeletal muscle myopathy: I. A histological, morphometric and biochemical investigation, *Neuropathol. Appl. Neurobiol.* 14:53-70 (1988).

Cserjesi et al., Myogenin induces the myocyte-specific enhancer binding factor MEF-2 independently of other muscle-specific gene products, *Mol. Cell. Biol.* 11:4854-62 (1991).

Cullen et al., Ultrastructure of the skeletal muscle in the X chromosome-linked dystrophic (mdx) mouse. Comparison with Duchenne muscular dystrophy, *Acta. Neuropathol.* 77:69-81 (1988).

Cushing et al., miR-29 is a major regulator of genes associated with pulmonary fibrosis, *Am. J. Respir. Cell. Mol. Biol.* 45:287-94 (2011).

De et al., High levels of persistent expression of alphal-antitrypsin mediated by the nonhuman primate serotype rh.10 adeno-associated virus despite preexisting immunity to common human adeno-associated viruses, *Mol. Ther.* 13:67-76 (2006).

Deconinck et al., Utrophin-dystrophin-deficient mice as a model for Duchenne muscular dystrophy, *Cell.* 90:717-27 (1997).

Desguerre et al., Endomysial fibrosis in Duchenne muscular dystrophy: a marker of poor outcome associated with macrophage alternative activation, *J. Neuropathol. Exp. Neurol.* 68:762-73 (2009).

Diprimio et al., Adeno-associated virus for the treatment of muscle diseases: toward clinical trials, *Curr. Opin. Mol. Ther.* 12:553-60 (2010).

Dupont-Versteegden et al., Differential expression of muscular dystrophy in diaphragm versus hindlimb muscles of mdx mice, *Muscle Nerve.* 15:1105-10 (1992).

Eisenberg et al., Distinctive patterns of microRNA expression in primary muscular disorders, *Proc. Natl. Acad. Sci. USA.* 104:17016-21 (2007).

Gao et al., Clades of Adeno-associated viruses are widely disseminated in human tissues, *J. Virol.* 78:6381-8 (2004).

Genbank Accession No. AF085716, Adeno-associated virus 5 DNA binding trs helicase (Rep22) and capsid protein (VP1) genes, complete cds, Feb. 9, 1999.

Genbank Accession No. AX753246, Sequence 1 from Patent EP1310571, Jun. 23, 2003.

Genbank Accession No. AX753249, Sequence 4 from Patent EP1310571, Jun. 23, 2003.

Genbank Accession No. NC_001729, Adeno-associated virus-3, complete genome, Aug. 13, 2018.

Genbank Accession No. NC_001829, Adeno-associated virus-4, complete genome, Aug. 13, 2018.

Genbank Accession No. NC_001862, Adeno-associated virus 6, complete genome, Jan. 12, 2004.

Genbank Accession No. NC_002077, Adeno-associated virus-1, complete genome, Aug. 13, 2018.

Grady et al., Skeletal and cardiac myopathies in mice lacking utrophin and dystrophin: a model for Duchenne muscular dystrophy, *Cell.* 90:729-38 (1997).

Grose et al., Homologous recombination mediates functional recovery of dysferlin deficiency following AAV5 gene transfer, *PLoS One.* 7:e39233 (2012).

Gutpell et al., Skeletal muscle fibrosis in the mdx/utrn+/− mouse validates its suitability as a murine model of Duchenne muscular dystrophy, *PloS one.* 10:e0117306 (2015).

Hakim et al., Monitoring murine skeletal muscle function for muscle gene therapy, *Methods. Mol. Biol.* 709:75-89 (2011).

Heller et al., 379 MicroRNA-29 and Micro-Dystrophin Combinatorial Therapy Suppresses Fibrosis and Restores Function to mdx/utrn+/− Mice, *Molecular Therapy.* 24:S151 (2016).

Herzog et al., Stable gene transfer and expression of human blood coagulation factor IX after intramuscular injection of recombinant adeno-associated virus, *Proc. Natl. Acad. Sci. USA.* 94:5804-9 (1997).

Hoffman et al., Dystrophin: the protein product of the Duchenne muscular dystrophy locus, *Cell.* 51:919-28 (1987).

International Preliminary Reporton Patentability, PCT/US2017/027635 (dated Oct. 16, 2018).

International Search Report and Written Opinion, PCT/US2017/027635 (dated Jul. 19, 2017).

Jiang et al., MicroRNAs and the regulation of fibrosis, *FEBS J.* 277:2015-2021 (2010).

Johnson et al., Muscle creatine kinase sequence elements regulating skeletal and cardiac muscle expression in transgenic mice, *Mol. Cell. Biol.* 9:3393-9 (1989).

Kessler et al., Gene delivery to skeletal muscle results in sustained expression and systemic delivery of a therapeutic protein, *Proc. Natl. Acad. Sci. USA.* 93:14082-7 (1996).

(56) References Cited

OTHER PUBLICATIONS

Kim et al., microRNA-directed cleavage of ATHB15 mRNA regulates vascular development in *Arabidopsis* inflorescence stems, *Plant J.* 42:84-94 (2005).
Lewis et al., Generation of neutralizing activity against human immunodeficiency virus type 1 in serum by antibody gene transfer, *J. Virol.* 76:8769-75 (2002).
Liu et al., Adeno-associated virus-mediated microdystrophin expression protects young mdx muscle from contraction-induced injury, *Mol. Ther.* 11:245-56 (2005).
Love et al., An autosomal transcript in skeletal muscle with homology to dystrophin, *Nature.* 339:55-8 (1989).
Mader et al., A steroid-inducible promoter for the controlled overexpression of cloned genes in eukaryotic cells, *Proc. Natl. Acad. Sci. USA.* 90:5603-7 (1993).
Marsic et al., Vector design Tour de Force: integrating combinatorial and rational approaches to derive novel adeno-associated virus variants, *Mol. Ther.* 22:1900-9 (2014).
Meadows et al., Reducing skeletal muscle fibrosis with AAV-Delivered miR-29 (P04.089), *Neurology.* 78:1-2 (2012).
Mendell et al., A phase 1/2a follistatin gene therapy trial for becker muscular dystrophy, *Mol. Ther.* 23:192-201 (2015).
Mendell et al., Evidence-based path to newborn screening for Duchenne muscular dystrophy, *Ann. Neurol.* 71:304-13 (2012).
Mendell et al., Limb-girdle muscular dystrophy type 2D gene therapy restores alpha-sarcoglycan and associated proteins, *Ann. Neurol.* 66:290-7 (2009).
Mendell et al., Sustained alpha-sarcoglycan gene expression after gene transfer in limb-girdle muscular dystrophy, type 2D, *Ann. Neurol.* 68:629-38 (2010).
Mori et al., Two novel adeno-associated viruses from cynomolgus monkey: pseudotyping characterization of capsid protein, *Virology.* 330:375-83 (2004).
Mulieri et al., Protection of human left ventricular myocardium from cutting injury with 2,3-butanedione monoxime, *Circ. Res.* 65:1441-9 (1989).
Murphy et al., Long-term correction of obesity and diabetes in genetically obese mice by a single intramuscular injection of recombinant adeno-associated virus encoding mouse leptin, *Proc. Natl. Acad. Sci. USA.* 94:13921-6 (1997).
Muscat et al., Multiple 5'-flanking regions of the human alpha-skeletal actin gene synergistically modulate muscle-specific expression, *Mol. Cell. Biol.* 7:4089-99 (1987).
Nevo et al., The Ras antagonist, farnesylthiosalicylic acid (FTS), decreases fibrosis and improves muscle strength in dy/dy mouse model of muscular dystrophy, *PloS one.* 6:e18049 (2011).
Rafael et al., Skeletal muscle-specific expression of a utrophin transgene rescues utrophin-dystrophin deficient mice, *Nat. Genet.* 19:79-82 (1998).
Roderburg et al., Micro-RNA profiling reveals a role for miR-29 in human and murine liver fibrosis, *Hepatology.* 53:209-18 (2011).
Rodino-Klapac et al., A translational approach for limb vascular delivery of the micro-dystrophin gene without high volume or high pressure for treatment of Duchenne muscular dystrophy, *J. Transl. Med.* 5:45 (2007).
Rodino-Klapac et al., Micro-dystrophin and follistatin co-delivery restores muscle function in aged DMD model, *Hum. Mol. Genet.* 22:4929-37 (2013).
Rodino-Klapac et al., Persistent expression of FLAG-tagged micro dystrophin in nonhuman primates following intramuscular and vascular delivery, *Mol. Ther.* 18:109-117 (2010).
Ruffing et al., Mutations in the carboxy terminus of adeno-associated virus 2 capsid proteins affect viral infectivity: lack of an RGD integrin-binding motif, *J. Gen. Virol.* 75:3385-92 (1994).
Sacco et al., Short telomeres and stem cell exhaustion model Duchenne muscular dystrophy in mdx/mTR mice, *Cell.* 143:1059-71 (2010).
Semenza et al., Hypoxia-inducible nuclear factors bind to an enhancer element located 3' to the human erythropoietin gene, *Proc. Natl. Acad. Sci. USA.* 88:5680-4 (1991).

Squire et al., Prevention of pathology in mdx mice by expression of utrophin: analysis using an inducible transgenic expression system, *Hum. Mol. Genet.* 11:3333-3344 (2002).
Srivastava et al., Nucleotide sequence and organization of the adeno-associated virus 2 genome, *J. Virol.* 75:555-64 (1994).
Stedman et al., The mdx mouse diaphragm reproduces the degenerative changes of Duchenne muscular dystrophy, *Nature.* 352:536-9 (1991).
Straub et al., Muscular dystrophies and the dystrophin-glycoprotein complex, *Curr. Opin. Neurol.* 10:168-175(1997).
Tinsley et al., Expression of full-length utrophin prevents muscular dystrophy in mdx mice, *Nat. Med.* 4:1441-4(1998).
Tinsley et al., Primary structure of dystrophin-related protein, *Nature.* 360:591-3 (1992).
Van Rooij et al., Dysregulation of microRNAs after myocardial infarction reveals a role of miR-29 in cardiac fibrosis, *Proc. Natl. Acad. Sci. USA.* 105:13027-32 (2008).
Wallace et al., Mechanisms of muscle degeneration, regeneration, and repair in the muscular dystrophies, *Annu. Rev. Physiol.* 71:37-57 (2009).
Weintraub et al., The myoD gene family: nodal point during specification of the muscle cell lineage, *Science.* 251:761-6 (1991).
Xiao et al., Efficient long-term gene transfer into muscle tissue of immunocompetent mice by adeno-associated virus vector, *J. Virol.* 70:8098-108 (1996).
Zhou et al., Haploinsufficiency of utrophin gene worsens skeletal muscle inflammation and fibrosis in mdx mice, *J. Neurol. Sci.* 264:106-11 (2008).
Zhou et al., Targeting Fibrosis in Duchenne Muscular Dystrophy, *J Neuropathol. Exp. Neurol.* 69:771-6 (2010).
Guan et al., Gene therapy in monogenic congenital myopathies, *Methods,* 99:91-8 (2015).
Harper et al., Modular fexibility of dystrophin: Implications for gene therapy of Duchenne Muscular Dystrophy, *Nat. Med.,* 8(3):253-61 (2002).
Martin et al., Translational Studies of GLAGT2 Gene Therapy for Duchenne Muscular Dystrophy, https://apps.dtic.mil/dtic/tr/fulltext/u2a613577.pdf Retrieved on Dec. 12, 2018.
Salva et al., Design of tissue-specific regulatory Cassettes for High-level rAAV-mediated Expression in Skeletal and Cardiac Muscle, *Amer. Soc. Gene. Ther.* 15(2):320-9 (2007).
Extended European Search Report, Application No. 17783236.7 dated Oct. 24, 2019.
Koo et al., Long-term functional adeno-associated virus-microdystrophin expression in the dystrophic CXMDj dog, *J. Gene Med.* 13:497-506 (2011).
Anderson et al., Nucleic acid hybridisation: A practical approach, Ch. 4, IRL Press Limited (Oxford, England), 1935, 73-111.
Bulfield et al., X chromosome-linked muscular dystrophy (mdx) in the mouse, Proc. Natl. Acad. Sci. USA., 81(4):1189-1192 (1984).
Carter, Adeno-associated Virus Vectors, Current Opinions in Biotechnology, 1533-539 (1992).
Clark et al., A Stable Cell Line Carrying Adenovirus-Inducible Rep and Cap Genes Allows for Infectivity Titration of Adeno-Associated Virus Vectors, Gene Therapy, 3:1124-1132 (1996).
Clark et al., Highly purified recombinant adeno-associated virus vectors are biologically active and free of detectable helper and wild-type viruses, Hum. Gene. Ther., 10(6):1031-1039 (1999).
Clemens et al., Recombinant truncated dystrophin minigenes: construction, expression, and adenoviral delivery, Hum. Gene Ther., 6:1477-1485 (1995).
Dong et al., Quantitative analysis of the packaging capacity of recombinant adeno-associated virus, Human Gene Therapy, 7:2101-2112 (1996).
Douglas Ingram, JP Morgan 39th Annual Healthcare Conference, Jan. 11, 2021.
European Application No. 17783236, European Search Report and Opinion, dated Oct. 24, 2019.
Flotte et al., Gene Expression from Adeno-associated Virus Vectors in Airway Epithelial Cells, Am. J. Respir. Cell Mol. Biol., 7:349-356, (1992).
Foster et al., Codon and mRNA sequence optimization of microdystrophin transgenes improves expression and physiological

(56) References Cited

OTHER PUBLICATIONS outcome in dystrophic mdx mice following AAV2/8 gene transfer, Mol. Ther., 16(11):1825-1832 (2008).
Franz et al., Association of nonsense mutation of dystrophin gene with disruption of sarcoglycan complex in X-linked dilated cardiomyopathy, Lanc., 355(9217):1781-1785 (2000).
Gupta et al., Codon optimization, Project Report, 1-11 (2003).
Harper et al., Modular flexibility of dystrophin: implications for gene therapy of duchenne muscular dystrophy, Nat. Med., 8:253-261 (2002).
Hartigan-O'Connor et al., Progress toward gene therapy of duchenne muscular dystrophy, Seminars in Neurology, 19(3):323-332(1999).
Hauser et al., Functional analysis of truncated dystrophin minigenes in the muscles of mdx mice, Abstract 2081, The American Journal of Human Genetics, S61(4) (1997).
Hayashita-Kinoh et al., Intra-Amniotic rAAV-Mediated Microdystrophin Gene Transfer Improves Canine X-Linked Muscular Dystrophy and May Induce Immune Tolerance, Mol. Ther., 23(4):627-637 (2015).
Heller et al., 379. MicroRNA-29 and Micro-Dystrophin Combinatorial Therapy Suppresses Fibrosis and Restores Function to mdx/utm+/− Mice, Mol. Ther., 24(1): S151 (2016).
Heller et al., Alternative to gene replacement for duchenne muscular dystrophy using human alpha7 integrin (ITGA7), Doctoral dissertation abstract only, 1-2 (2014).
Hermonat et al., Use of adeno-associated vims as a mammalian DNA cloning vector: transduction of neomycin resistance into mammalian tissue culture cells, Proc. Natl. Acad. Sci. U.S.A., 81(20):6466-6470 (1984).
International Application No. PCT/US19/037489, International Search Report and Written Opinion, dated Sep. 6, 2019.
International Application No. PCT/US19/37489, International Preliminary Report on Patentability, dated Dec. 30, 2020.
International Application No. PCT/US17/27630, International Preliminary Report on Patentability, dated Oct. 25, 2018.
International Application No. PCT/US17/27630, International Search Report and Written Opinion, dated Jul. 14, 2017.
International Application No. PCT/US17/27636, International Preliminary Report on Patentability, dated Oct. 25, 2018.
International Application No. PCT/US17/27636, International Search Report and Written Opinion, dated Jul. 5, 2017.
International Application No. PCT/US2017/027635, International Preliminary Report on Patentability, dated Oct. 16, 2018.
International Application No. PCT/US2017/027635, International Search Report and Written Opinion, dated Jul. 19, 2017.
International Application No. PCT/US2018/022853, International Preliminary Report on Patentability, dated May 28, 2020, 14 pages.
International Application No. PCT/US2018/022853, International Search Report and Written Opinion, dated Jun. 6, 2018, 12 pages.
International Preliminary Report on Patentability for Corresponding International Application No. PCT/IB18/001201, dated Sep. 26, 2019.
International Preliminary Report on Patentability for Corresponding International Application No. PCT/US18/22881, dated Jan. 7, 2020, 51 pages.
International Search Report and Written Opinion for Corresponding International Application No. PCT/IB2018/001201, dated Feb. 5, 2019.
International Search Report and Written Opinion for Corresponding International Application No. PCT/US18/22881, dated May 22, 2018, 12 pages.
Jaynes et al., Transcriptional Regulation of the Muscle Creatine Kinase Gene and Regulated Expression in Transfected Mouse Myoblasts, Mol. Cell. Biol., 6(8):2855-64 (1986).
Kawecka et al., Adeno-Associated Virus (AAV) Mediated Dystrophin Gene Transfer Studies and Exon Skipping Strategies for Duchenne Muscular Dystrophy (DMD), Curr. Gene. Ther., 15(4):395-415 (2015).
Kriegel et al., The miR-29 family: genomics, cell biology, and relevance to renal and cardiovascular injury, Physiological Genomics, 44:237-244 (2012).

Laughlin et al., Cloning of infectious adeno-associated virus genomes in bacterial plasmids, Gene., 23(1):65-73 (1983).
Lebkowski et al., Adena-associated vims: a vector system for efficient introduction and integration of DNA into a variety of mammalian cell types, Mol. Cell. Biol., 7:3988-96 (1988).
Lederfein et al., Kilodalton Protein is a Major Product of the Duchenne Muscular Dystrophy Gene in Brain and Other Nonmuscle Tissues, Proc. Natl. Acad. Sci. USA., 89(12):5346-5350 (1992).
Martin, Translational Studies of GALGT2 Gene Therapy for Duchenne Muscular Dystrophy, Annual Report, Approved for Public Release Distribution Unlimited The Research Institute at Nationwide Children's Hospital Columbus (2013).
Mauro et al., A critical analysis of codon optimization in human therapeutics, Trends in Molecular Medicine, 20(11):604-13 (2014).
Mclaughlin et al., Adeno-associated virus general transduction vectors: analysis of proviral structures, J. Virol., 62(6):1963-73 (1988).
Mendell et al., A randomized, double blind, placebo-controlled, gene-delivery clinical trial of rAAVrh74.MHCK7.micro-dystrophin for Duchenne muscular dystrophy; ASGCT Virtual Annual Meeting, (2021).
Muzyczka, Use of adeno-associated virus as a general transduction vector for mammalian cells, Current topics in Microbiology and Immunology, 158:97-129 (1992).
Paul et al., Increased viral titer through concentration of viral harvests from retroviral packaging lines, Human Gene Therapy, 4(5):609-615 (1993).
Perrin et al., An experimental rabies vaccine produced with a new BHK-21 suspension cell culture process: use of serum-free medium and perfusion reactor system, Vaccine, 13(13):4244-1250 (1995).
Phelps et al., Expression of full-length and truncated dystrophin mini-genes in transgenic mdx mice, Human Molecular Genetics, 4(8):4251-1258 (1995).
Pozsgai et al., Systemic AAV-mediated (Beta)-sarcoglycan delivery targeting cardiac and Skeletal muscle ameliorates histological and functional deficits in LGMD2E mice, Mol Ther., 25(4):855-869 (2017).
Recan et al., Are cysteine-rich and COOH-terminal domains of dystrophin critical for sarcolemmal localization?, J. Clin. Invest., 89:712-716 (1992).
Rodino et al., Persistent Expression of FLAG-tagged Microdystrophin in Nonhuman Primates Following Intramuscular and Vascular Delivery, Mol. Ther., 18(1):109-117 (2010).
Rodino-Klapac et al., Development of AAVrh74 Micro-dystrophin gene transfer therapy for duchenne, Muscular Dystrophy Association (MDA) Virtual Clinical and Scientific Conference (2021).
Sakamoto et al., Micro-dystrophin cDNA ameliorates dystrophic phenotypes when introduced into mdx mice as a transgene, Biochem. and Biophysical Research Comm., 293:1265-1272 (2002).
Sambrook et al., Molecular cloning: A laboratory manual, 2nd Ed., Cold Spring Harbor Laboratory (1989).
Samulski et al., A recombinant plasmid from which an infectious adeno-associated virus genome can be excised in vitro and its use to study viral replication, J. Virol., 61(10):3096-3101 (1987).
Samulski et al., Cloning of adeno-associated virus into pBR322: rescue of intact virus from the recombinant plasmid in human cells, Proc. Natl. Acad Sci. U.S.A., 79(6):2077-2081 (1982).
Samulski et al., Helper-free stocks of recombinant adeno-associated viruses: normal integration does not require viral gene expression, J. Virol., 63(9):3822-3828 (1989).
Schnepp et al., Highly purified recombinant adeno-associated virus vectors. Preparation and quantitation, Methods Mol. Med., 69:427-443 (2002).
Senapathy et al., Molecular cloning of adeno-associated virus variant genomes and generation of infectious virus by recombination in mammalian cells, J. Biol. Chem., 259:4661-4666 (1984).
Sicinski et al., The molecular basis of muscular dystrophy in the mdx mouse: a point mutation, Science, 244:1578-80 (1989).
Sondergaard et al., AAV.Dysferlin Overlap Vectors Restore Function in Dysferlinopathy Animal Models, Annals of Clinical and Translational Neurology, 2:256-270 (2015).

(56) References Cited

OTHER PUBLICATIONS

Tratschin et al., A human parvovirus, adeno-associated virus, as a eucaryotic vector: transient expression and encapsidation of the procaryotic gene for chloramphenicol acetyltransferase, Mol. Cell. Biol., 4(10):2072-2081 (1984).
Tratschin et al., Adeno-associated Virus Vector for High-Frequency Integration, Expression, and Rescue of Genes in Mammalian Cells, Mol. Cell. Biol., 5:3251-3260 (1985).
Wang et al., Adena-associated virus vector carrying human minidystrophin genes effectively ameliorates muscular dystrophy in mdx mouse model, PNAS, 97:13714-13719 (2000).
Wells et al., Expression of human full-length and minidystrophin in transgenic rndx mice: implications for gene therapy of duchenne muscular dystrophy, Hum. Mol. Gene., 4(8):1245-2250 (1995).
Xiao et al., Production of high-titer recombinant adeno-associated virus vectors in the absence of helper adenovirus, J. Virol., 12:2224-2232 (1998).
Yuasa et al., Effective restoration of dystrophin-associated proteins in vivo by adenovirus-mediated transfer of truncated dystrophin cDNAs, FEBS Letters, 425:329-336 (1998).
Chicoine et al., Plasmapheresis Eliminates the Negative Impact of AAV Antibodies on Microdystrophin Gene Expression Following Vascular Delivery, *Molec. Ther.,* 22(2):338-47 (2014).
Heller et al., MicroRNA-29 overexpression by adeno-associated virus suppresses fibrosis and restores muscle function in combination with micro-dystrophin, *JCI Insight.* 2(9):1-13 (2017).

\* cited by examiner

Figure 1

scAAVrh.74.CMV.miR29c

SEQ ID NO: 2: miR-29C IN A miR-30 BACKBONE

GGCCGGCC*tgtttgaatgaggcttcagtactttacagaat*CGTTGCCTGCACATCTTGGAAACACTTGCTGGGATTACT
TCTTCAGGTTAACCCAACAGAAGGCTCGAGAAGGTATATTGCTGTTGACAGTGAGCGCAACCGA
TTTCAAATGGTGCTAGAGTGAAGCCACAGATGTCTAGCACCATTTGAAATCGGTTATGCCTACTG
CCTCGGAATTCAAGGGGCTACTTTAGGAGCAATTATCTTGTTTACTAAAACTGAATACCTTGCTA
TCTCTTTGATACATTGGCCGGCC FSE-I cut site (restriction site)
miR-30 backbone
miR-30 stem loop (GTGAAGCCACAGATG; SEQ ID NO: 5)
miR-29c target (sense) strand (ACCGATTTCAAATGGTGCTAGA; SEQ ID NO:3))
miR-29c guide (antisense) strand (TCTAGCACCATTTGAAATCGGTTA; SEQ ID NO: 4)

Predicted hairpin structure (SEQ ID NO:6)

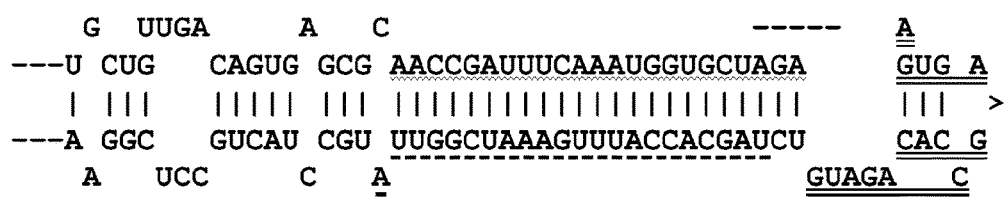

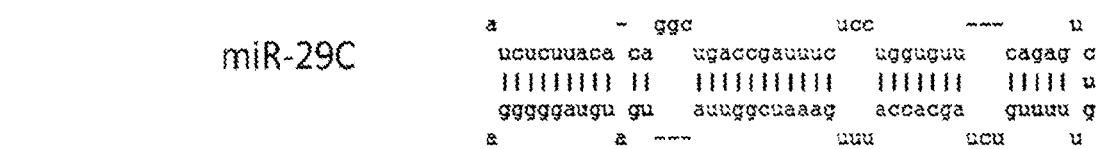

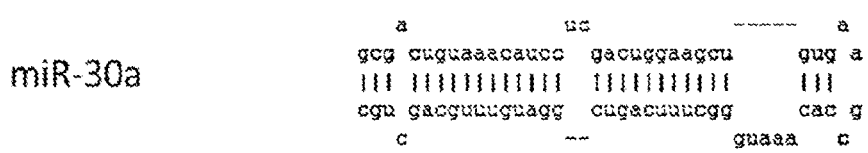

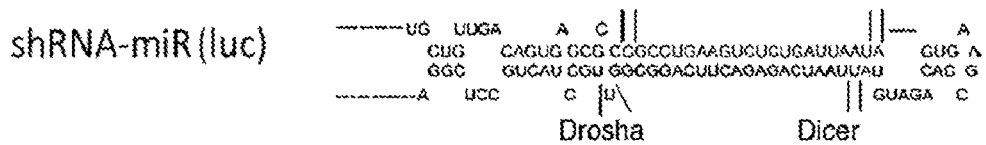

Sirius Red miR-29c

Absolute Force

Specific Force

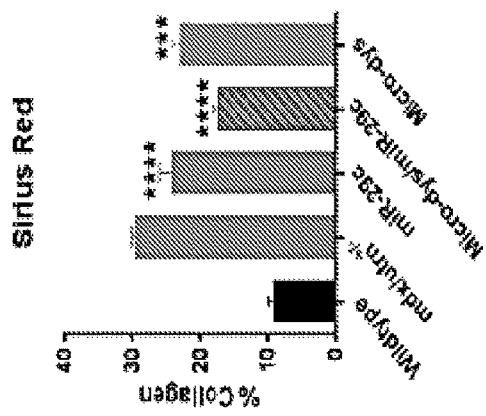
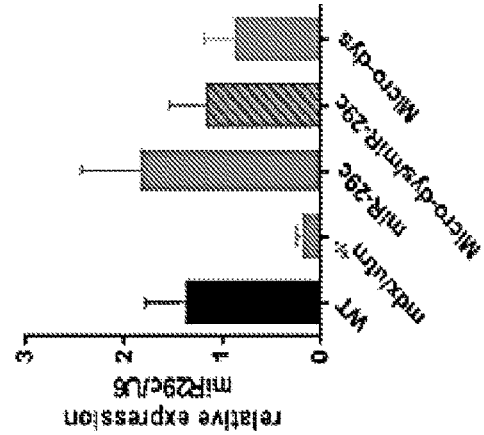
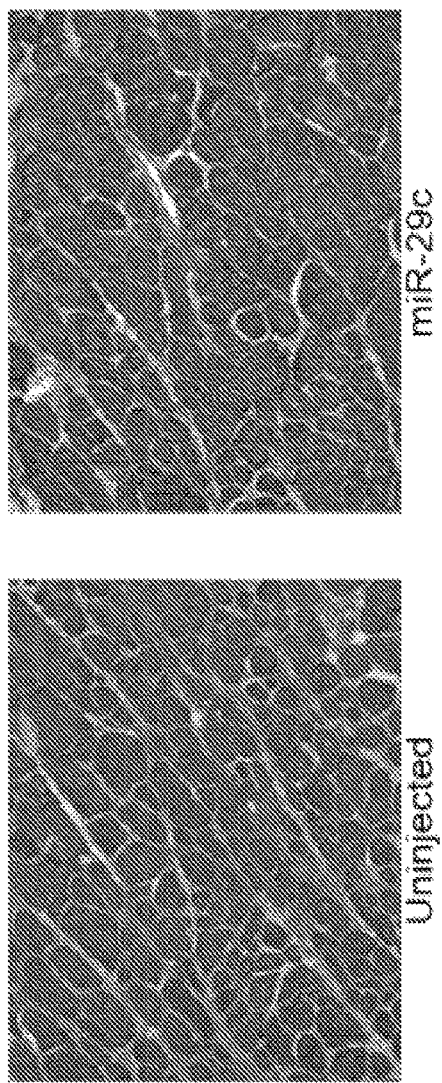

Col1A

Col3A

FBN

TGF-β

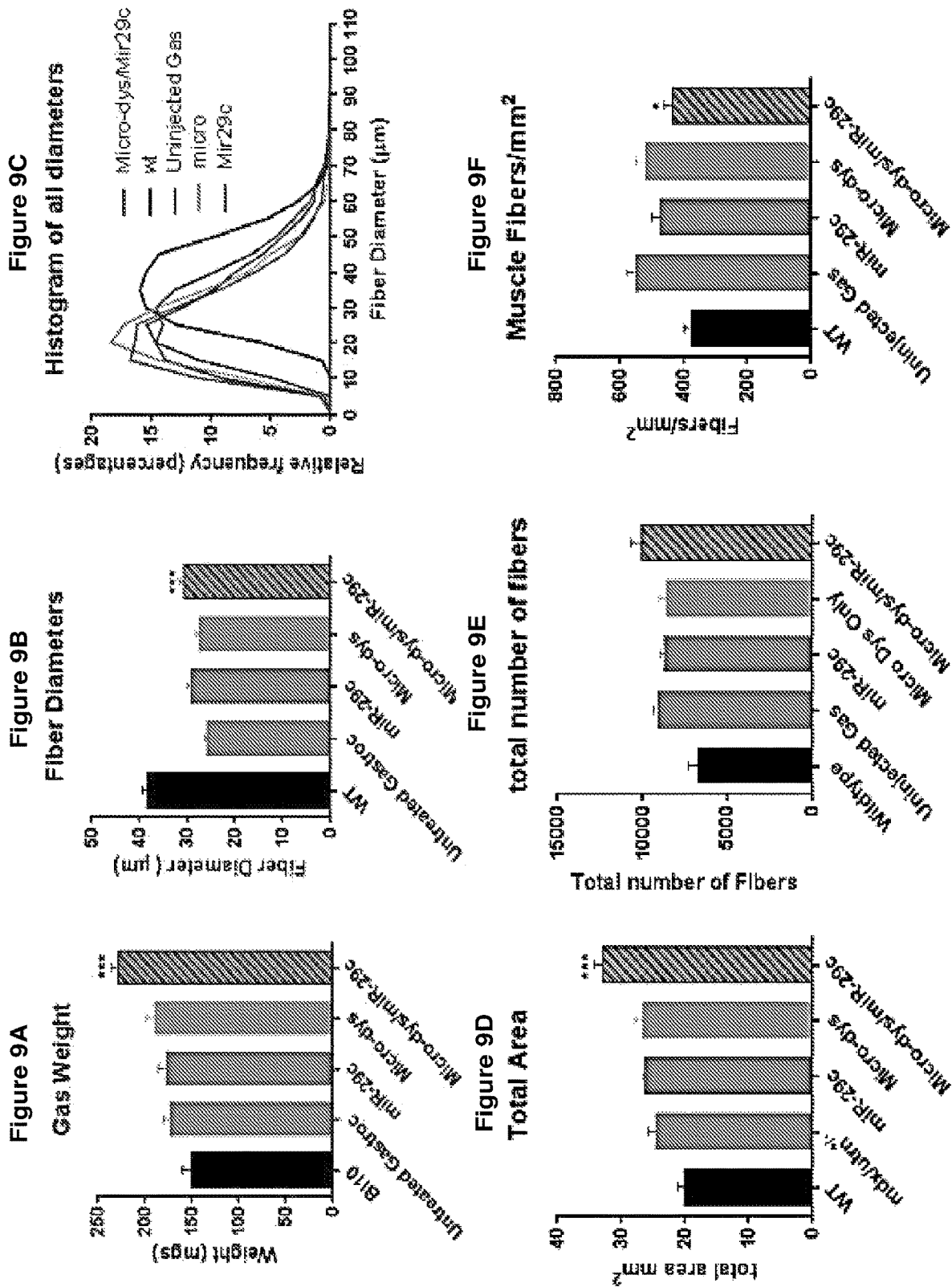

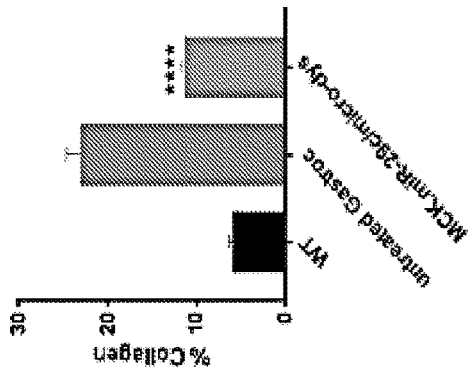
Figure 13B Sirius Red
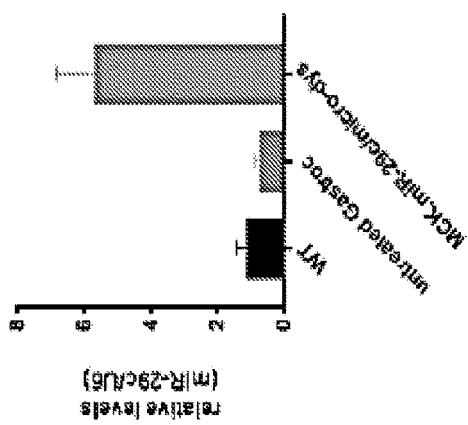
Figure 13C miR-29c
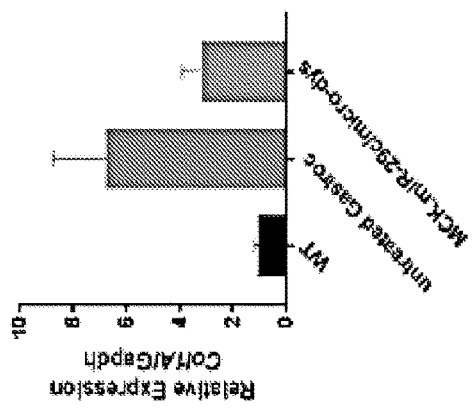
Figure 13D Col1A
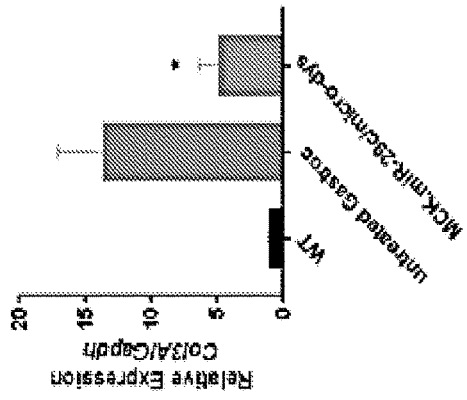
Figure 13E Col3A
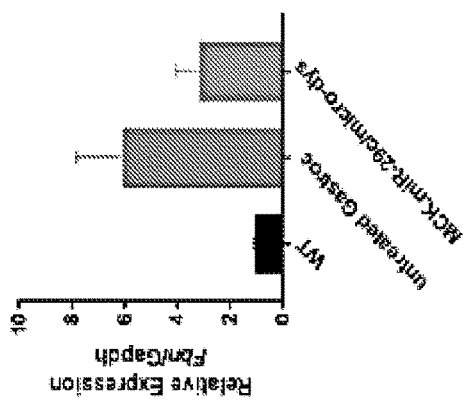
Figure 13F Fbn
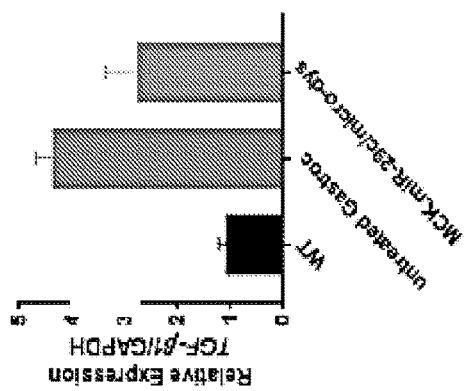
Figure 13G Tgfb1

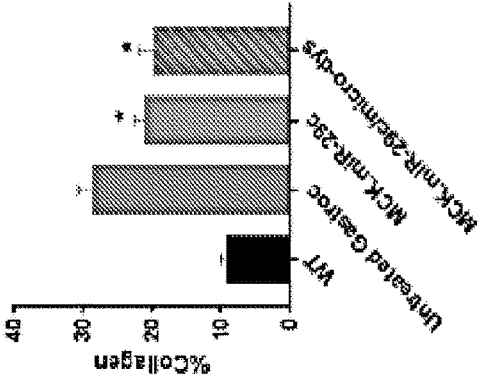
Figure 14B Sirius Red
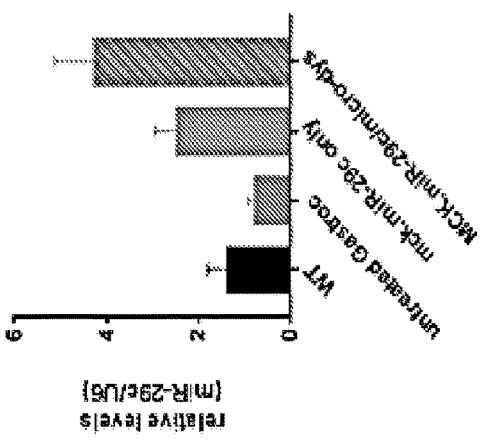
Figure 14C miR-29c levels
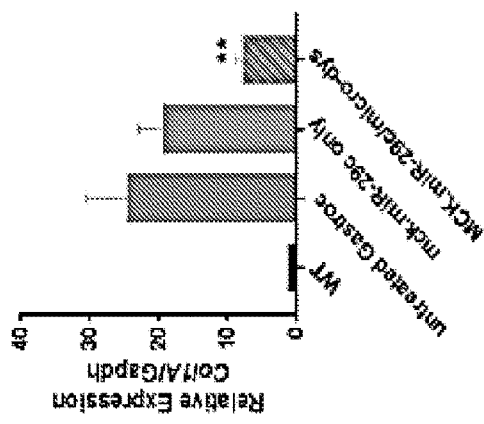
Figure 14D Col1A
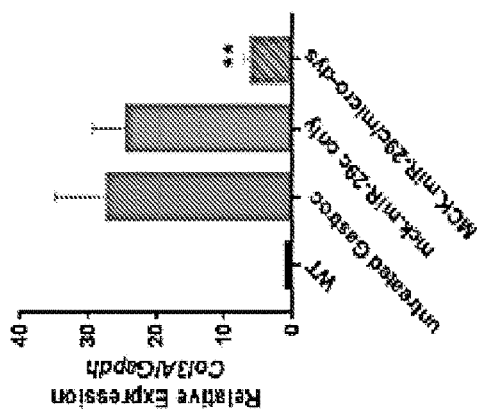
Figure 14E Col3A
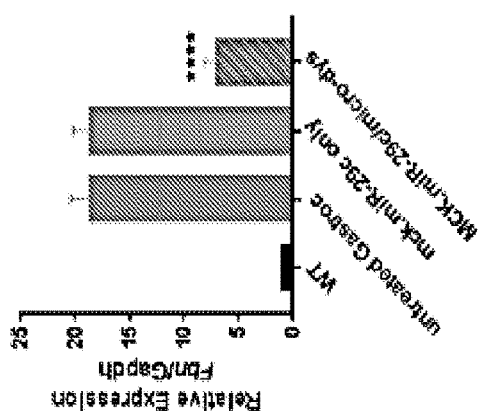
Figure 14F Fbn
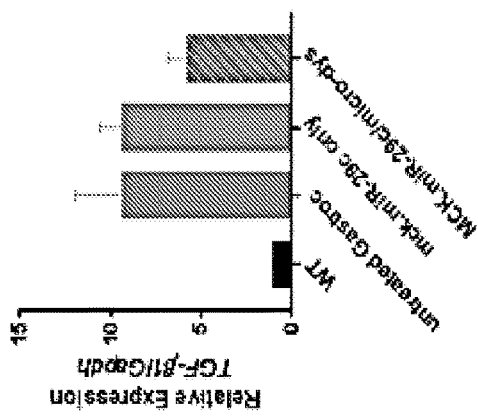
Figure 14G Tgfb1

Absolute Force

Specific Force

Gas weights

Fiber Diameter

Histogram of All diameters

Number of fibers/mm2

Figure 18A pAAV.CMV.miR29C Sequence (SEQ ID NO: 1)

Main features:
CMV promoter- 120-526
EF1a Intron- 927-1087, 1380-1854
miR-29c- 1257-1284
shRNA-miR29-c with primary seed sequence- 1088-1375
PolyA- 1896-2091

CAGCAGCTGCGCGCTCGCTCGCTCACTGAGGCCGCCCGGGCAAAGCCCGGGCGTCGGGCGACCTTTGGTCGCCCG
GCCTCAGTGAGCGAGCGAGCGCGCAGAGAGGGAGTGGGGTTAAACTCGTTACATAACTTACGGTAAATGGCCCG
CCTGGCTGACCGCCCAACGACCCCCGCCCATTGACGTCAATAATGACGTATGTTCCCATAGTAACGCCAATAGGGA
CTTTCCATTGACGTCAATGGGTGGAGTATTTACGGTAAACTGCCCACTTGGCAGTACATCAAGTGTATCATATGCC
AAGTACGCCCCCTATTGACGTCAATGACGGTAAATGGCCCGCCTGGCATTATGCCCAGTACATGACCTTATGGGAC
TTTCCTACTTGGCAGTACATCTACGTATTAGTCATCGCTATTACCATGGTGATGCGGTTTTGGCAGTACATCAATGG
GCGTGGATAGCGGTTTGACTCACGGGGATTTCCAAGTCTCCACCCCATTGACGTCAATGGGAGTTTGTTTTGGCAC
CAAAATCAACGGGACTTTCCAAAATGTCGTAACAACTCCGCCCCATTGACGCAAATGGGCGGTAGGCGTGTACGG
TGGGAGGTCTATATAAGCAGAGCTCGTTTAGTGAACCGTCAGATCGCCTGGAGACGCCATCCACGCTGTTTTGACC
TCCATAGAAGACACCGGGACCGATCCAGCCTCCGGACTCTAGAGGATCCGGTACTCGAGGAACTGAAAAACCAGA
AAGTTAACTGGTAAGTTTAGTCTTTTTGTCTTTTATTTCAGGTCCCGGATCCGGTGGTGGTGCAAATCAAAGAACTG
CTCCTCAGTGGATGTTGCCTTTACTTCTAGGCCTGTACGGAAGTGTTACTTCTGCTCTAAAAGCTGCGGAATTGTAC
CCGGGGCCGATCCACCGGTCTTTTTCGCAACGGGTTTGCCGCCAGAACACAGGTAAGTGCCGTGTGTGGTTCCCG
CGGGCGGCGACGGGGCCCGTGCGTCCAGCGCACATGTTCGGCGAGGCGGGGCCTGCGAGCGCGGCCACCGAG
AATCGGACGGGGGTAGTCTCAAGCTGGCCGGCCTGTTTGAATGAGGCTTCAGTACTTTACAGAATCGTTGCCTGC
ACATCTTGGAAACACTTGCTGGGATTACTTCTTCAGGTTAACCCAACAGAAGGCTCGAGAAGGTATATTGCTGTTG
ACAGTGAGCGCAACCGATTTCAAATGGTGCTAGAGTGAAGCCACAGATGTCTAGCACCATTTGAAATCGGTTATG
CCTACTGCCTCGGAATTCAAGGGGCTACTTTAGGAGCAATTATCTTGTTTACTAAAACTGAATACCTTGCTATCTCTT
TGATACATTGGCCGGCCTGCTCTGGTGCCTGGCCTCGCGCCGCCGTGTATCGCCCCGCCCTGGGCGGCAAGGCTG
GCCCGGTCGGCACCAGTTGCGTGAGCGGAAAGATGGCCGCTTCCCGGCCCTGCTGCAGGGAGCTCAAAATGGAG
GACGCGGCGCTCGGGAGAGCGGGCGGGTGAGTCACCCACACAAAGGAAAAGGGCCTTTCCGTCCTCAGCCGTCG
CTTCATGTGACTCCACGGAGTACCGGGCGCCGTCCAGGCACCTCGATTAGTTCTCGAGCTTTTGGAGTACGTCGTC
TTTAGGTTGGGGGGAGGGGTTTTATGCGATGGAGTTTCCCCACACTGAGTGGGTGGAGACTGAAGTTAGGCCAG
CTTGGCACTTGATGTAATTCTCCTTGGAATTTGCCCTTTTTGAGTTTGGATCTTGGTTCATTCTCAAGCCTCAGACAG
TGGTTCAAAGTTTTTTTCTTCCATTTCAGGTGTCGTGAAAAGCTAGCGCTACCGGACTCAGATCTCGAGCTCAAGCT
GCGGGGATCCAGACATGATAAGATACATTGATGAGTTTGGACAAACCACAACTAGAATGCAGTGAAAAAAATGCT
TTATTTGTGAAATTTGTGATGCTATTGCTTTATTTGTAACCATTATAAGCTGCAATAAACAAGTTAACAACAACAATT
GCATTCATTTTATGTTTCAGGTTCAGGGGGAGGTGTGGGAGGTTTTTTCACTAGTAGCATGGCTACGTAGATAAGT
AGCATGGCGGGTTAATCATTAACTACAAGGAACCCCTAGTGATGGAGTTGGCCACTCCCTCTCTGCGCGCTCGCTC
GCTCACTGAGGCCGGGCGACCAAAGGTCGCCCGACGCCCGGGCTTTGCCCGGGCGGCCTCAGTGAGCGAGCGAG
CGCGCCAGCTGGCGTAATAGCGAAGAGGCCCGCACCGATCGCCCTTCCCAACAGTTGCGCAGCCTGAATGGCGAA
TGGAATTCCAGACGATTGAGCGTCAAAATGTAGGTATTTCCATGAGCGTTTTCCTGTTGCAATGGCTGGCGGTAA
TATTGTTCTGGATATTACCAGCAAGGCCGATAGTTTGAGTTCTTCTACTCAGGCAAGTGATGTTATTACTAATCAAA
GAAGTATTGCGACAACGGTTAATTTGCGTGATGGACAGACTCTTTTACTCGGTGGCCTCACTGATTATAAAAACAC
TTCTCAGGATTCTGGCGTACCGTTCCTGTCTAAAATCCCTTTAATCGGCCTCCTGTTTAGCTCCCGCTCTGATTCTAA
CGAGGAAAGCACGTTATACGTGCTCGTCAAAGCAAC

Figure 18B

```
CATAGTACGCGCCCTGTAGCGGCGCATTAAGCGCGGCGGGTGTGGTGGTTACGCGCAGCGTGACCGCTACACTTG
CCAGCGCCCTAGCGCCCGCTCCTTTCGCTTTCTTCCCTTCCTTTCTCGCCACGTTCGCCGGCTTTCCCCGTCAAGCTCT
AAATCGGGGGCTCCCTTTAGGGTTCCGATTTAGTGCTTTACGGCACCTCGACCCCAAAAAACTTGATTAGGGTGAT
GGTTCACGTAGTGGGCCATCGCCCTGATAGACGGTTTTTCGCCCTTTGACGTTGGAGTCCACGTTCTTTAATAGTG
GACTCTTGTTCCAAACTGGAACAACACTCAACCCTATCTCGGTCTATTCTTTTGATTTATAAGGGATTTTGCCGATTT
CGGCCTATTGGTTAAAAAATGAGCTGATTTAACAAAAATTTAACGCGAATTTTAACAAAATATTAACGTTTACAATT
TAAATATTTGCTTATACAATCTTCCTGTTTTTGGGGCTTTTCTGATTATCAACCGGGGTACATATGATTGACATGCTA
GTTTTACGATTACCGTTCATCGATTCTCTTGTTTGCTCCAGACTCTCAGGCAATGACCTGATAGCCTTTGTAGAGACC
TCTCAAAAATAGCTACCCTCTCCGGCATGAATTTATCAGCTAGAACGGTTGAATATCATATTGATGGTGATTTGACT
GTCTCCGGCCTTTCTCACCCGTTTGAATCTTTACCTACACATTACTCAGGCATTGCATTTAAAATATATGAGGGTTCT
AAAAATTTTTATCCTTGCGTTGAAATAAAGGCTTCTCCCGCAAAAGTATTACAGGGTCATAATGTTTTGGTACAAC
CGATTTAGCTTTATGCTCTGAGGCTTTATTGCTTAATTTTGCTAATTCTTTGCCTTGCCTGTATGATTTATTGGATGTT
GGAATTCCTGATGCGGTATTTTCTCCTTACGCATCTGTGCGGTATTTCACACCGCATATGGTGCACTCTCAGTACAA
TCTGCTCTGATGCCGCATAGTTAAGCCAGCCCCGACACCCGCCAACACCCGCTGACGCGCCCTGACGGGCTTGTCT
GCTCCCGGCATCCGCTTACAGACAAGCTGTGACCGTCTCCGGGAGCTGCATGTGTCAGAGGTTTTCACCGTCATCA
CCGAAACGCGCGAGACGAAAGGGCCTCGTGATACGCCTATTTTTATAGGTTAATGTCATGATAATAATGGTTTCTT
AGACGTCAGGTGGCACTTTTCGGGGAAATGTGCGCGGAACCCCTATTTGTTTATTTTTCTAAATACATTCAAATATG
TATCCGCTCATGAGACAATAACCCTGATAAATGCTTCAATAATATTGAAAAAGGAAGAGTATGAGTATTCAACATT
TCCGTGTCGCCCTTATTCCCTTTTTTGCGGCATTTTGCCTTCCTGTTTTTGCTCACCCAGAAACGCTGGTGAAAGTAA
AAGATGCTGAAGATCAGTTGGGTGCACGAGTGGGTTACATCGAACTGGATCTCAACAGCGGTAAGATCCTTGAGA
GTTTTCGCCCCGAAGAACGTTTTCCAATGATGAGCACTTTTAAAGTTCTGCTATGTGGCGCGGTATTATCCCGTATT
GACGCCGGGCAAGAGCAACTCGGTCGCCGCATACACTATTCTCAGAATGACTTGGTTGAGTACTCACCAGTCACA
GAAAAGCATCTTACGGATGGCATGACAGTAAGAGAATTATGCAGTGCTGCCATAACCATGAGTGATAACACTGCG
GCCAACTTACTTCTGACAACGATCGGAGGACCGAAGGAGCTAACCGCTTTTTTGCACAACATGGGGGATCATGTA
ACTCGCCTTGATCGTTGGGAACCGGAGCTGAATGAAGCCATACCAAACGACGAGCGTGACACCACGATGCCTGTA
GCAATGGCAACAACGTTGCGCAAACTATTAACTGGCGAACTACTTACTCTAGCTTCCCGGCAACAATTAATAGACT
GGATGGAGGCGGATAAAGTTGCAGGACCACTTCTGCGCTCGGCCCTTCCGGCTGGCTGGTTTATTGCTGATAAAT
CTGGAGCCGGTGAGCGTGGGTCTCGCGGTATCATTGCAGCACTGGGGCCAGATGGTAAGCCCTCCCGTATCGTAG
TTATCTACACGACGGGGAGTCAGGCAACTATGGATGAACGAAATAGACAGATCGCTGAGATAGGTGCCTCACTGA
TTAAGCATTGGTAACTGTCAGACCAAGTTTACTCATATATACTTTAGATTGATTTAAAACTTCATTTTTAATTTAAAA
GGATCTAGGTGAAGATCCTTTTTGATAATCTCATGACCAAAATCCCTTAACGTGAGTTTTCGTTCCACTGAGCGTCA
GACCCCGTAGAAAAGATCAAAGGATCTTCTTGAGATCCTTTTTTTCTGCGCGTAATCTGCTGCTTGCAAACAAAAAA
ACCACCGCTACCAGCGGTGGTTTGTTTGCCGGATCAAGAGCTACCAACTCTTTTTCCGAAGGTAACTGGCTTCAGC
AGAGCGCAGATACCAAATACTGTCCTTCTAGTGTAGCCGTAGTTAGGCCACCACTTCAAGAACTCTGTAGCACCGC
CTACATACCTCGCTCTGCTAATCCTGTTACCAGTGGCTGCTGCCAGTGGCGATAAGTCGTGTCTTACCGGGTTGGA
CTCAAGACGATAGTTACCGGATAAGGCGCAGCGGTCGGGCTGAACGGGGGGTTCGTGCACACAGCCCAGCTTGG
AGCGAACGACCTACACCGAACTGAGATACCTACAGCGTGAGCTATGAGAAAGCGCCACGCTTCCCGAAGGGAGA
AAGGCGGACAGGTATCCGGTAAGCGGCAGGGTCGGAACAGGAGAGCGCACGAGGGAGCTTCCAGGGGGAAAC
GCCTGGTATCTTTATAGTCCTGTCGGGTTTCGCCACCTCTGACTTGAGCGTCGATTTTTGTGATGCTCGTCAGGGGG
GCGGAGCCTATGGAAAAACGCCAGCAACGCGGCCTTTTTACGGTTCCTGGCCTTTTGCTGGCCTTTTGCTCACATG
TTCTTTCCTGCGTTATCCCCTGATTCTGTGGATAACCGTATTACCGCCTTTGAGTGAGCTGATACCGCTCGCCGCAG
CCGAACGACCGAGCGCAGCGAGTCAGTGAGCGAGGAAGCGGAAGAGCGCCCAATACGCAAACCGCCTCTCCCCG
CGCGTTGGCCGATTCATTAATG
```

Figure 20A

SEQ ID NO: 9
Main features:
MCK promoter
Chimeric intron sequence
Human micro-dystrophin sequence
Poly A tail
Ampicillin resistance
pGEX plasmid backbone with pBR322 origin or replication GCCCAATACGCAAACCGCCTCTCCCCGCGCGTTGGCCGATTCATTAATGCAGCTGGC
GCGCTCGCTCGCTCACTGAGGCCGCCCGGGCAAAGCCCGGGCGTCGGGCGACCTTT
GGTCGCCCGGCCTCAGTGAGCGAGCGAGCGCGCAGAGAGGGAGTGGCCAACTCCAT
CACTAGGGGTTCCTTGTAGTTAATGATTAACCCGCCATGCTAATTATCTACGTAGCC
ATGTCTAGACAGCCACTATGGGTCTAGGCTGCCCATGTAAGGAGGCAAGGCCTGGG
GACACCCGAGATGCCTGGTTATAATTAACCCAGACATGTGGCTGCTCCCCCCCCCA
ACACCTGCTGCCTGAGCCTCACCCCCACCCCGGTGCCTGGGTCTTAGGCTCTGTACA
CCATGGAGGAGAAGCTCGCTCTAAAAATAACCCTGTCCCTGGTGGGCTGTGGGGGA
CTGAGGGCAGGCTGTAACAGGCTTGGGGGCCAGGGCTTATACGTGCCTGGGACTCC
CAAAGTATTACTGTTCCATGTTCCCGGCGAAGGGCCAGCTGTCCCCGCCAGCTAGA
CTCAGCACTTAGTTTAGGAACCAGTGAGCAAGTCAGCCCTTGGGGCAGCCCATACA
AGGCCATGGGGCTGGGCAAGCTGCACGCCTGGGTCCGGGGTGGGCACGGTGCCCGG
GCAACGAGCTGAAAGCTCATCTGCTCTCAGGGGCCCCTCCCTGGGGACAGCCCCTCC
TGGCTAGTCACACCCTGTAGGCTCCTCTATATAACCCAGGGGCACAGGGGCTGCCCC
CGGGTCACCACCACCTCCACAGCACAGACAGACACTCAGGAGCCAGCCAGCCAGGT
AAGTTTAGTCTTTTTGTCTTTTATTTCAGGTCCCGGATCCGGTGGTGGTGCAAATCAA
AGAACTGCTCCTCAGTGGATGTTGCCTTTACTTCTAGGCCTGTACGGAAGTGTTACTT
CTGCTCTAAAAGCTGCGGAATTGTACCCGCGGCCGCCACCATGCTGTGGTGGGAGG
AGGTGGAGGATTGTTATGAAAGGGAGGACGTGCAGAAGAAGACTTTTACCAAGTGG
GTGAACGCTCAGTTCAGCAAATTTGGGAAGCAGCACATCGAGAATCTGTTTTCCGAC
CTGCAGGATGGGAGACGGCTGCTGGATCTGCTGGAAGGACTGACTGGCCAGAAGCT
GCCCAAAGAGAAGGGGAGCACTAGGGTGCACGCCCTGAACAACGTGAACAAAGCT
CTGAGAGTGCTGCAGAACAACAACGTGGATCTGGTGAATATTGGCAGTACTGATAT
CGTGGACGGGAACCACAAACTGACACTGGGCCTGATCTGGAACATTATTCTGCACTG
GCAGGTGAAAAATGTGATGAAGAACATCATGGCCGGGCTGCAGCAGACCAATTCCG
AGAAGATCCTGCTGTCTTGGGTGCGGCAGAGCACCCGCAACTATCCCCAGGTGAAC
GTGATTAACTTCACTACATCCTGGAGCGACGGGCTGGCCCTGAATGCTCTGATTCAC
AGCCACAGGCCTGATCTGTTCGACTGGAATAGCGTGGTGTGCCAGCAGTCTGCCACA
CAGCGCCTGGAACATGCCTTCAATATCGCTCGGTACCAGCTGGGGATCGAAAAACT
GCTGGACCCAGAGGATGTGGACACTACATACCCAGATAAAAGTCTATTCTGATGT
ACATTACTAGCCTGTTCCAGGTGCTGCCACAGCAGGTGTCTATTGAAGCCATTCAGG
AGGTGGAAATGCTGCCCCGCCCCCCAAAGTGACTAAAGAGGAGCATTTCAGCTG
CATCATCAGATGCATTACAGCCAGCAGATTACCGTGAGCCTGGCTCAGGGATATGA
GCGCACCAGTAGTCCAAAACCACGGTTCAAGTCCTACGCTTATAC

Figure 20B

CCAGGCTGCCTACGTGACAACTAGCGACCCTACTAGATCCCCCTTTCCATCCCAGCA
CCTGGAGGCCCCAGAGGACAAGAGCTTTGGGTCCAGCCTGATGG
AAAGCGAGGTGAATCTGGATCGGTACCAGACAGCCCTGGAGGAGGTGCTGAGCTGG
CTGCTGAGTGCTGAAGACACACTGCAGGCCCAGGGCGAAATTTCCAATGACGTGGA
AGTGGTGAAGGATCAGTTCCACACACACGAGGGCTATATGATGGACCTGACAGCTC
ACCAGGGGCGCGTGGGCAATATCCTGCAGCTGGGCTCTAAACTGATCGGCACCGGG
AAACTGAGTGAGGACGAGGAAACAGAAGTGCAGGAGCAGATGAACCTGCTGAACA
GCCGCTGGGAGTGTCTGAGAGTGGCTAGTATGGAGAAGCAGTCCAACCTGCACCGG
GTGCTGATGGACCTGCAGAACCAGAAACTGAAAGAGCTGAACGACTGGCTGACAAA
GACTGAGGAACGCACAAGGAAGATGGAGGAGGAGCCACTGGGACCCGACCTGGAG
GATCTGAAGAGACAGGTGCAGCAGCATAAGGTGCTGCAGGAGGATCTGGAACAGG
AGCAGGTGCGGGTGAACTCCCTGACACATATGGTGGTGGTGGTGGACGAATCTAGT
GGAGATCACGCCACCGCCGCCCTGGAGGAACAGCTGAAGGTGCTGGGGGACCGGTG
GGCCAACATTTGCCGGTGGACCGAGGACAGGTGGGTGCTGCTGCAGGACATCCTGC
TGAAATGGCAGAGGCTGACCGAGGAGCAGTGTCTGTTTAGTGCTTGGCTGAGCGAG
AAAGAGGACGCCGTGAACAAGATCCACACAACCGGCTTTAAGGATCAGAACGAAAT
GCTGTCTAGCCTGCAGAAACTGGCTGTGCTGAAGGCCGATCTGGAGAAAAAGAAGC
AGAGCATGGGCAAACTGTATAGCCTGAAACAGGACCTGCTGAGCACCCTGAAGAAC
AAGAGCGTGACCCAGAAGACAGAAGCCTGGCTGGATAACTTTGCCCGCTGCTGGGA
CAACCTGGTGCAGAAACTGGAGAAAAGTACAGCTCAGATCTCTCAGGCTGTGACCA
CAACCCAGCCTAGCCTGACCCAGACAACCGTGATGGAAACCGTGACCACCGTGACA
ACCCGCGAACAGATCCTGGTGAAACATGCCCAGGAAGAGCTGCCACCTCCACCTCC
CCAGAAGAAGAGAACCCTGGAGCGGCTGCAGGAGCTGCAGGAAGCCACTGACGAA
CTGGACCTGAAGCTGAGGCAGGCCGAAGTGATTAAGGGGTCTTGGCAGCCTGTGGG
CGATCTGCTGATTGATTCCCTGCAGGACCACCTGGAAAAGGTGAAGGCTCTGAGAG
GCGAAATTGCTCCACTGAAGGAGAACGTGAGTCATGTGAACGATCTGGCTAGACAG
CTGACAACACTGGGCATCCAGCTGAGCCCATACAATCTGAGCACACTGGAGGACCT
GAATACCAGGTGGAAGCTGCTGCAGGTGGCTGTGGAAGACCGGGTGCGGCAGCTGC
ATGAGGCCCATCGCGACTTCGGACCAGCCAGCCAGCACTTTCTGAGCACATCCGTGC
AGGGGCCCTGGGAGAGGGCCATTTCTCCCAACAAGGTGCCCTACTATATTAATCACG
AGACCCAGACCACTTGTTGGGACCATCCCAAGATGACAGAACTGTACCAGTCCCTG
GCCGATCTGAACAACGTGAGGTTTAGCGCTTACAGAACCGCTATGAAGCTGAGACG
GCTGCAGAAGGCCCTGTGCCTGGATCTGCTGTCCCTGTCCGCCGCCTGCGATGCCCT
GGATCAGCATAATCTGAAGCAGAACGATCAGCCAATGGATATCCTGCAGATCATCA
ACTGCCTGACCACTATCTACGACAGGCTGGAGCAGGAGCACAACAACCTGGTGAAC
GTGCCTCTGTGCGTGGATATGTGCCTGAACTGGCTGCTGAACGTGTATGACACTGGG
CGCACCGGCCGGATCAGAGTGCTGAGTTTTAAAACTGGGATTATCTCCCTGTGTAAG
GCCCACCTGGAGGACAAGTACAGGTACCTGTTCAAGCAGGTGGCTAGTAGCACTGG
ATTTTGTGACCAGCGCCGCCTGGGACTGCTGCTGCATGATAGTATCCAGATTCCTAG
ACAGCTGGGAGAGGTGGCTAGTTTCGGAGGATCTAACATCGAACCCAGCGTGCGCA
GCTGTTTCCAGTTTGCCAATAACAAACCTGAAATCGAGGCTGCTCTGTTCCTGGATT
GGATGCGCCTGGAACCACAGAGCATGGTGTGGCTGCCTGTGCTGCACAGAGTGG

Figure 20C

CTGCCGCCGAAACTGCCAAGCACCAGGCTAAATGCAACATCTGCAAGGAATGTCCC
ATTATCGGCTTTCGCTACAGGAGTCTGAAACATTTTAACTACGAT
ATTTGCCAGAGCTGCTTCTTTTCCGGAAGAGTGGCCAAAGGACACAAGATGCACTAC
CCTATGGTGGAATATTGCACCCCAACTACATCTGGCGAAGATGTGCGCGATTTTGCC
AAGGTGCTGAAGAATAAGTTTCGGACTAAGAGGTACTTCGCCAAGCACCCCCGCAT
GGGGTATCTGCCAGTGCAGACAGTGCTGGAAGGAGACAATATGGAGACCGATACAA
TGTGAGCGGCCGCAATAAAGATCTTTATTTTCATTAGATCTGTGTGTTGGTTTTTG
TGTGTCTAGAGCATGGCTACGTAGATAAGTAGCATGGCGGGTTAATCATTAACTACA
AGGAACCCCTAGTGATGGAGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTG
AGCGAGCGAGCGCGCCAGCTGGCGTAATAGCGAAGAGGCCCGCACCGATCGCCCTT
CCCAACAGTTGCGCAGCCTGAATGGCGAATGGAAGTTCCAGACGATTGAGCGTCAA
AATGTAGGTATTTCCATGAGCGTTTTCCTGTTGCAATGGCTGGCGGTAATATTGTTC
TGGATATTACCAGCAAGGCCGATAGTTTGAGTTCTTCTACTCAGGCAAGTGATGTTA
TTACTAATCAAAGAAGTATTGCGACAACGGTTAATTTGCGTGATGGACAGACTCTTT
TACTCGGTGGCCTCACTGATTATAAAAACACTTCTCAGGATTCTGGCGTACCGTTCCT
GTCTAAAATCCCTTTAATCGGCCTCCTGTTTAGCTCCCGCTCTGATTCTAACGAGGAA
AGCACGTTATACGTGCTCGTCAAAGCAACCATAGTACGCGCCCTGTAGCGGCGCATT
AAGCGCGGCGGGTGTGGTGGTTACGCGCAGCGTGACCGCTACACTTGCCAGCGCCC
TAGCGCCCGCTCCTTTCGCTTTCTTCCCTTCCTTTCTCGCCACGTTCGCCGGCTTTCCC
CGTCAAGCTCTAAATCGGGGGCTCCCTTTAGGGTTCCGATTTAGTGATTTACGGCAC
CTCGACCCCAAAAAACTTGATTAGGGTGATGGTTCACGTAGTGGGCCATCGCCCTGA
TAGACGGTTTTTCGCCCTTTGACGTTGGAGTCCACGTTCTTTAATAGTGGACTCTTGT
TCCAAACTGGAACAACACTCAACCCTATCTCGGTCTATTCTTTTGATTTATAAGGGAT
TTTGCCGATTTCGGCCTATTGGTTAAAAAATGAGCTGATTTAACAAAAATTTAACGC
GAATTTTAACAAAATATTAACGTTTACAATTTAAATATTTGCTTATACAATCTTCCTG
TTTTTGGGGCTTTTCTGATTATCAACCGGGGTACATATGATTGACATGCTAGTTTTAC
GATTACCGTTCATCGATTCTCTTGTTTGCTCCAGACTCTCAGGCAATGACCTGATAGC
CTTTGTAGAGACCTCTCAAAAATAGCTACCCTCTCCGGCATGAATTTATCAGCTAGA
ACGGTTGAATATCATATTGATGGTGATTTGACTGTCTCCGGCCTTTCTCACCCGTTTG
AATCTTTACCTACACATTACTCAGGCATTGCATTTAAAATATATGAGGGTTCTAAAA
ATTTTTATCCTTGCGTTGAAATAAAGGCTTCTCCCGCAAAAGTATTACAGGGTCATA
ATGTTTTTGGTACAACCGATTTAGCTTTATGCTCTGAGGCTTTATTGCTTAATTTTGCT
AATTCTTTGCCTTGCCTGTATGATTTATTGGATGTTGGAAGTTCCTGATGCGGTATTT
TCTCCTTACGCATCTGTGCGGTATTCACACCGCATATGGTGCACTCTCAGTACAATC
TGCTCTGATGCCGCATAGTTAAGCCAGCCCCGACACCCGCCAACACCCGCTGACGCG
CCCTGACGGGCTTGTCTGCTCCCGGCATCCGCTTACAGACAAGCTGTGACCGTCTCC
GGGAGCTGCATGTGTCAGAGGTTTTCACCGTCATCACCGAAACGCGCGAGACGAAA
GGGCCTCGTGATACGCCTATTTTTATAGGTTAATGTCATGATAATAATGGTTTCTTAG
ACGTCAGGTGGCACTTTTCGGGGAAATGTGCGCGGAACCCCTATTTGTTTATTTTTCT
AAATACATTCAAATATGTATCCGCTCATGAGACAATAACCCTGATAAATGCTTCAAT
AATATTGAAAAAGGAAGAGTATGAGTATTCAACATTTCCGTGTCGCCCTT

Figure 20D

ATTCCCTTTTTTGCGGCATTTTGCCTTCCTGTTTTTGCTCACCCAGAAACGCTGGTGA
AAGTAAAAGATGCTGAAGATCAGTTGGGTGCACGAGTGGGTTAC
ATCGAACTGGATCTCAACAGCGGTAAGATCCTTGAGAGTTTTCGCCCCGAAGAACGT
TTTCCAATGATGAGCACTTTTAAAGTTCTGCTATGTGGCGCGGTATTATCCCGTATTG
ACGCCGGGCAAGAGCAACTCGGTCGCCGCATACACTATTCTCAGAATGACTTGGTTG
AGTACTCACCAGTCACAGAAAAGCATCTTACGGATGGCATGACAGTAAGAGAATTA
TGCAGTGCTGCCATAACCATGAGTGATAACACTGCGGCCAACTTACTTCTGACAACG
ATCGGAGGACCGAAGGAGCTAACCGCTTTTTGCACAACATGGGGGATCATGTAAC
TCGCCTTGATCGTTGGGAACCGGAGCTGAATGAAGCCATACCAAACGACGAGCGTG
ACACCACGATGCCTGTAGCAATGGCAACAACGTTGCGCAAACTATTAACTGGCGAA
CTACTTACTCTAGCTTCCCGGCAACAATTAATAGACTGGATGGAGGCGGATAAAGTT
GCAGGACCACTTCTGCGCTCGGCCCTTCCGGCTGGCTGGTTTATTGCTGATAAATCT
GGAGCCGGTGAGCGTGGGTCTCGCGGTATCATTGCAGCACTGGGGCCAGATGGTAA
GCCCTCCCGTATCGTAGTTATCTACACGACGGGGAGTCAGGCAACTATGGATGAACG
AAATAGACAGATCGCTGAGATAGGTGCCTCACTGATTAAGCATTGGTAACTGTCAG
ACCAAGTTTACTCATATATACTTTAGATTGATTTAAAACTTCATTTTTAATTTAAAAG
GATCTAGGTGAAGATCCTTTTTGATAATCTCATGACCAAAATCCCTTAACGTGAGTT
TTCGTTCCACTGAGCGTCAGACCCCGTAGAAAAGATCAAAGGATCTTCTTGAGATCC
TTTTTTTCTGCGCGTAATCTGCTGCTTGCAAACAAAAAAACCACCGCTACCAGCGGT
GGTTTGTTTGCCGGATCAAGAGCTACCAACTCTTTTTCCGAAGGTAACTGGCTTCAG
CAGAGCGCAGATACCAAATACTGTCCTTCTAGTGTAGCCGTAGTTAGGCCACCACTT
CAAGAACTCTGTAGCACCGCGTACATACCTCGCTCTGCTAATCCTGTTACCAGTGGC
TGCTGCCAGTGGCGATAAGTCGTGTCTTACCGGGTTGGACTCAAGACGATAGTTACC
GGATAAGGCGCAGCGGTCGGGCTGAACGGGGGGTTCGTGCACACAGCCCAGCTTGG
AGCGAACGACCTACACCGAACTGAGATACCTACAGCGTGAGCTATGAGAAAGCGCC
ACGCTTCCCGAAGGGAGAAAGGCGGACAGGTATCCGGTAAGCGGCAGGGTCGGAA
CAGGAGAGCGCACGAGGGAGCTTCCAGGGGGAAACGCCTGGTATCTTTATAGTCCT
GTCGGGTTTCGCCACCTCTGACTTGAGCGTCGATTTTTGTGATGCTCGTCAGGGGGG
CGGAGCCTATGGAAAAACGCCAGCAACGCGGCCTTTTACGGTTCCTGGCCTTTTGC
TGGCCTTTTGCTCACATGTTCTTTCCTGCGTTATCCCCTGATTCTGTGGATAACCGTA
TTACCGGGTTTGAGTGAGCTGATACCGCTCGCCGCAGCCGAACGACCGAGCGCAGC
GAGTCAGTGAGCGACCAAGCGGAAGAGC

Figure 21A

SEQ ID NO: 7 : human micro-dystrophin gene

ATGCTGTGGTGGGAGGAGGTGGAGGATTGTTATGAAAGGGAGGACGTGCAGAAGA
AGACTTTTACCAAGTGGGTGAACGCTCAGTTCAGCAAATTTGGGAAGCAGCACATC
GAGAATCTGTTTTCCGACCTGCAGGATGGGAGACGGCTGCTGGATCTGCTGGAAGG
ACTGACTGGCCAGAAGCTGCCCAAAGAGAAGGGGAGCACTAGGGTGCACGCCCTGA
ACAACGTGAACAAAGCTCTGAGAGTGCTGCAGAACAACAACGTGGATCTGGTGAAT
ATTGGCAGTACTGATATCGTGGACGGGAACCACAAACTGACACTGGGCCTGATCTG
GAACATTATTCTGCACTGGCAGGTGAAAAATGTGATGAAGAACATCATGGCCGGGC
TGCAGCAGACCAATTCCGAGAAGATCCTGCTGTCTTGGGTGCGGCAGAGCACCCGC
AACTATCCCCAGGTGAACGTGATTAACTTCACTACATCCTGGAGCGACGGGCTGGCC
CTGAATGCTCTGATTCACAGCCACAGGCCTGATCTGTTCGACTGGAATAGCGTGGTG
TGCCAGCAGTCTGCCACACAGCGCCTGGAACATGCCTTCAATATCGCTCGGTACCAG
CTGGGGATCGAAAAACTGCTGGACCCAGAGGATGTGGACACTACATACCCAGATAA
AAAGTCTATTCTGATGTACATTACTAGCCTGTTCCAGGTGCTGCCACAGCAGGTGTC
TATTGAAGCCATTCAGGAGGTGGAAATGCTGCCCCGCCCCCCCAAAGTGACTAAAG
AGGAGCATTTTCAGCTGCATCATCAGATGCATTACAGCCAGCAGATTACCGTGAGCC
TGGCTCAGGGATATGAGCGCACCAGTAGTCCAAAACCACGGTTCAAGTCCTACGCTT
ATACCCAGGCTGCCTACGTGACAACTAGCGACCCTACTAGATCCCCCTTTCCATCCC
AGCACCTGGAGGCCCCAGAGGACAAGAGCTTTGGGTCCAGCCTGATGGAAAGCGAG
GTGAATCTGGATCGGTACCAGACAGCCCTGGAGGAGGTGCTGAGCTGGCTGCTGAG
TGCTGAAGACACACTGCAGGCCCAGGGCGAAATTTCCAATGACGTGGAAGTGGTGA
AGGATCAGTTCCACACACGAGGGCTATATGATGGACCTGACAGCTCACCAGGGG
CGCGTGGGCAATATCCTGCAGCTGGGCTCTAAACTGATCGGCACCGGGAAACTGAG
TGAGGACGAGGAAACAGAAGTGCAGGAGCAGATGAACCTGCTGAACAGCCGCTGG
GAGTGTCTGAGAGTGGCTAGTATGGAGAAGCAGTCCAACCTGCACCGGGTGCTGAT
GGACCTGCAGAACCAGAAACTGAAAGAGCTGAACGACTGGCTGACAAAGACTGAG
GAACGCACAAGGAAGATGGAGGAGGAGCCACTGGGACCCGACCTGGAGGATCTGA
AGAGACAGGTGCAGCAGCATAAGGTGCTGCAGGAGGATCTGGAACAGGAGCAGGT
GCGGGTGAACTCCCTGACACATATGGTGGT

Figure 21B

GGTGGTGGACGAATCTAGTGGAGATCACGCCACCGCCGCCCTGGAGGAACAGCTGA
AGGTGCTGGGGGACCGGTGGGCCAACATTTGCCGGTGGACCGAGGACAGGTGGGTG
CTGCTGCAGGACATCCTGCTGAAATGGCAGAGGCTGACCGAGGAGCAGTGTCTGTTT
AGTGCTTGGCTGAGCGAGAAGAGGACGCCGTGAACAAGATCCACACAACCGGCTT
TAAGGATCAGAACGAAATGCTGTCTAGCCTGCAGAAACTGGCTGTGCTGAAGGCCG
ATCTGGAGAAAAAGAAGCAGAGCATGGGCAAACTGTATAGCCTGAAACAGGACCTG
CTGAGCACCCTGAAGAACAAGAGCGTGACCCAGAAGACAGAAGCCTGGCTGGATA
ACTTTGCCCGCTGCTGGGACAACCTGGTGCAGAAACTGGAGAAAAGTACAGCTCAG
ATCTCTCAGGCTGTGACCACAACCCAGCCTAGCCTGACCCAGACAACCGTGATGGA
AACCGTGACCACCGTGACAACCCGCGAACAGATCCTGGTGAAACATGCCCAGGAAG
AGCTGCCACCTCCACCTCCCCAGAAGAAGAGAACCCTGGAGCGGCTGCAGGAGCTG
CAGGAAGCCACTGACGAACTGGACCTGAAGCTGAGGCAGGCCGAAGTGATTAAGGG
GTCTTGGCAGCCTGTGGGCGATCTGCTGATTGATTCCCTGCAGGACCACCTGGAAAA
GGTGAAGGCTCTGAGAGGCGAAATTGCTCCACTGAAGGAGAACGTGAGTCATGTGA
ACGATCTGGCTAGACAGCTGACAACACTGGGCATCCAGCTGAGCCCATACAATCTG
AGCACACTGGAGGACCTGAATACCAGGTGGAAGCTGCTGCAGGTGGCTGTGGAAGA
CCGGGTGCGGCAGCTGCATGAGGCCCATCGCGACTTCGGACCAGCCAGCCAGCACT
TTCTGAGCACATCCGTGCAGGGGCCCTGGGAGAGGGCCATTTCTCCCAACAAGGTG
CCCTACTATATTAATCACGAGACCCAGACCACTTGTTGGGACCATCCCAAGATGACA
GAACTGTACCAGTCCCTGGCCGATCTGAACAACGTGAGGTTTAGCGCTTACAGAACC
GCTATGAAGCTGAGACGGCTGCAGAAGGCCCTGTGCCTGGATCTGCTGTCCCTGTCC
GCCGCCTGCGATGCCCTGGATCAGCATAATCTGAAGCAGAACGATCAGCCAATGGA
TATCCTGCAGATCATCAACTGCCTGACCACTATCTACGACAGGCTGGAGCAGGAGC
ACAACAACCTGGTGAACGTGCCTCTGTGCGTGGATATGTGCCTGAACTGGCTGCTGA
ACGTGTATGACACTGGGCGCACCGGCCGGATCAGAGTGCTGAGTTTTAAAACTGGG
ATTATCTCCCTGTGTAAGGCCCACCTGGAGGACAAGTACAGGTACCTGTTCAAGCAG
GTGGCTAGTAGCACTGGATTTTGTGACCAGCGCCGCCTGGGACTGCTGCTGCATGAT
AGTATCCAGATTCCTAGACAGCTGGGAGAGG

Figure 21C

TGGCTAGTTTCGGAGGATCTAACATCGAACCCAGCGTGCGCAGCTGTTTCCAGTTTG
CCAATAACAAACCTGAAATCGAGGCTGCTCTGTTCCTGGATTGGATGCGCCTGGAAC
CACAGAGCATGGTGTGGCTGCCTGTGCTGCACAGAGTGGCTGCCGCCGAAACTGCC
AAGCACCAGGCTAAATGCAACATCTGCAAGGAATGTCCCATTATCGGCTTTCGCTAC
AGGAGTCTGAAACATTTTAACTACGATATTTGCCAGAGCTGCTTCTTTTCCGGAAGA
GTGGCCAAAGGACACAAGATGCACTACCCTATGGTGGAATATTGCACCCCAACTAC
ATCTGGCGAAGATGTGCGCGATTTTGCCAAGGTGCTGAAGAATAAGTTTCGGACTAA
GAGGTACTTCGCCAAGCACCCCGCATGGGGTATCTGCCAGTGCAGACAGTGCTGG
AAGGAGACAATATGGAGACCGATACAATGTGAGC

Figure 22A pAAV.MCK.miR29C Sequence (SEQ ID NO: 12)

Main features:
MCK enhancer- 190-395 (SEQ ID NO: 10)
MCK promoter- 396-753 (SEQ ID NO: 11)
EF1a Intron- 1155-1315, 1609-2083
miR-29c-1487-1512
shRNA-miR29-c with primary seed sequence- 1316-1608
SV40 PolyA- 2094-2146

CTGNNNNNNGCGCGCTCGCTCGCTCACTGAGGCCGCCCGGGCAAAGCCCGGGCGTC
GGGCGACCTTTGGTCGCCCGGCCTCAGTGAGCGAGCGAGCGCGCAGAGAGGGAGTG
GCCAACTCCATCACTAGGGGTTCCTTGTAGTTAATGATTAACCCGCCATGCTAATTA
TCTACGTAGCCATGTCTAGACAGCCACTATGGGTCTAGGCTGCCCATGTAAGGAGGC
AAGGCCTGGGGACACCCGAGATGCCTGGTTATAATTAACCCAGACATGTGGCTGCTC
CCCCCCCCCAACACCTGCTGCCTGAGCCTCACCCCCACCCCGGTGCCTGGGTCTTAG
GCTCTGTACACCATGGAGGAGAAGCTCGCTCTAAAAATAACCCTGTCCCTGGTGGGC
TGTGGGGGACTGAGGGCAGGCTGTAACAGGCTTGGGGGCCAGGGCTTATACGTGCC
TGGGACTCCCAAAGTATTACTGTTCCATGTTCCCGGCGAAGGGCCAGCTGTCCCCCG
CCAGCTAGACTCAGCACTTAGTTTAGGAACCAGTGAGCAAGTCAGCCCTTGGGGCA
GCCCATACAAGGCCATGGGGCTGGGCAAGCTGCACGCCTGGGTCCGGGGTGGGCAC
GGTGCCCGGGCAACGAGCTGAAAGCTCATCTGCTCTCAGGGGCCCCTCCCTGGGGA
CAGCCCCTCCTGGCTAGTCACACCCTGTAGGCTCCTCTATATAACCCAGGGGCACAG
GGGCTGCCCCCGGGTCACCACCACCTCCACAGCACAGACAGACACTCAGGAGCCAG
CCAGCCAGGTAAGTTTAGTCTTTTTGTCTTTTATTTCAGGTCCCGGATCCGGTGGTGG
TGCAAATCAAAGAACTGCTCCTCAGTGGATGTTGCCTTTACTTCTAGGCCTGTACGG
AAGTGTTACTTCTGCTCTAAAAGCTGCGGAATTGTACCCGCCTAGAGGATCCGGTAC
TCGAGGAACTGAAAAACCAGAAAGTTAACTGGTAAGTTTAGTCTTTTTGTCTTTTAT
TTCAGGTCCCGGATCCGGTGGTGGTGCAAATCAAAGAACTGCTCCTCAGTGGATGTT
GCCTTTACTTCTAGGCCTGTACGGAAGTGTTACTTCTGCTCTAAAAGCTGCGGAATT
GTACCCGGGGCCGATCCACCGGTCTTTTTCGCAACGGGTTTGCCGCCAGAACACAGG
TAAGTGCCGTGTGTGGTTCCCGCGGGCGGCGACGGGGCCCGTGCGTCCCAGCGCAC
ATGTTCGGCGAGGCGGGGCCTGCGAGCGCGGCCACCGAGAATCGGACGGGGGTAGT
CTCAAGCTGGCCGGCCTGTTTGAATGAGGCTTCAGTACTTTACAGAATCGTTGCCTG
CACATCTTGGAAACACTTGCTGGGATTACTTCTTCAGGTTAACCCAACAGAAGGCTC
GAGAAGGTATATTGCTGTTGACAGTGAGCGCAACCGATTTCAAATGGTGCTAGAGT
GAAGCCACAGATGTCTAGCACCATTTGAAATCGGTTATGCCTACTGCCTCGGAATTC
AAGGGGCTACTTTAGGAGCAATTATCTTGTTTACTAAAACTGAATACCTTGCTATCT
CTTTGATACATTGGCCGGCCTGCTCTGGTGCCTGGCCTCGCGCCGCCGTGTATCGCC
CCGCCCTGGGCGGCAAGGCTGGCCCGGTCGGCACCAGTTGCGTGAGCGGAAAGATG
GCCGCTTCCCGGCCCTGCTGCAGGGAGCTCAAAATGGAGGACGCGGCGCTCGGGAG
AGCGGGCGGGTGAGTCACCCACACAAGGAAAAGGGCCTTTCCGTCCTCAGCCGTC
GCTTCATGTGACTCCACGGAGTACCGGGCGCCGTCCAGGCACCTCGATTAGTT

Figure 22B

CTCGAGCTTTTGGAGTACGTCGTCTTTAGGTTGGGGGGAGGGGTTTTATGCGATGGA
GTTTCCCCACACTGAGTGGGTGGAGACTGAAGTTAGGCCAGCTTGGCACTTGATGTA
ATTCTCCTTGGAATTTGCCCTTTTTGAGTTTGGATCTTGGTTCATTCTCAAGCCTCAG
ACAGTGGTTCAAAGTTTTTTTCTTCCATTTCAGGTGTCGTGAAAAGCTAGTGCGGCC
GCAATAAAAGATCTTTATTTTCATTAGATCTGTGTGTTGGTTTTTTGTGTGTCTAGAC
ATGGCTACGTAGATAATTAGCATGGCGGGTTAATCATTAACTACAAGGAACCCCTAG
TGATGGAGTTGGCCACTCCCTCTCTGCGCGCTCGCTCGCTCACTGAGGCCGGGCGAC
CAAAGGTCGCCCGACGCCCGGGCTTTGCCCGGGCGGCCTCAGTGAGCGAGCGAGCG
CGCNNNNNNCAGCTGGCGTAATAGCGAAGAGGCCCGCACCGATCGCCCTTCCCAAC
AGTTGCGCAGCCTGAATGGCGAATGGAAGTTCCAGACGATTGAGCGTCAAAATGTA
GGTATTTCCATGAGCGTTTTCCTGTTGCAATGGCTGGCGGTAATATTGTTCTGGATA
TTACCAGCAAGGCCGATAGTTTGAGTTCTTCTACTCAGGCAAGTGATGTTATTACTA
ATCAAAGAAGTATTGCGACAACGGTTAATTTGCGTGATGGACAGACTCTTTTACTCG
GTGGCCTCACTGATTATAAAAACACTTCTCAGGATTCTGGCGTACCGTTCCTGTCTA
AAATCCCTTTAATCGGCCTCCTGTTTAGCTCCCGCTCTGATTCTAACGAGGAAAGCA
CGTTATACGTGCTCGTCAAAGCAACCATAGTACGCGCCCTGTAGCGGCGCATTAAGC
GCGGCGGGTGTGGTGGTTACGCGCAGCGTGACCGCTACACTTGCCAGCGCCCTAGC
GCCCGCTCCTTTCGCTTTCTTCCCTTCCTTTCTCGCCACGTTCGCCGGCTTTCCCCGTC
AAGCTCTAAATCGGGGGCTCCCTTTAGGGTTCCGATTTAGTGATTTACGGCACCTCG
ACCCCAAAAAACTTGATTAGGGTGATGGTTCACGTAGTGGGCCATCGCCCTGATAGA
CGGTTTTTCGCCCTTTGACGTTGGAGTCCACGTTCTTTAATAGTGGACTCTTGTTCCA
AACTGGAACAACACTCAACCCTATCTCGGTCTATTCTTTTGATTTATAAGGGATTTTG
CCGATTTCGGCCTATTGGTTAAAAAATGAGCTGATTTAACAAAAATTTAACGCGAAT
TTTAACAAAATATTAACGTTTACAATTTAAATATTTGCTTATACAATCTTCCTGTTTT
TGGGGCTTTTCTGATTATCAACCGGGGTACATATGATTGACATGCTAGTTTTACGATT
ACCGTTCATCGATTCTCTTGTTTGCTCCAGACTCTCAGGCAATGACCTGATAGCCTTT
GTAGAGACCTCTCAAAAATAGCTACCCTCTCCGGCATGAATTTATCAGCTAGAACGG
TTGAATATCATATTGATGGTGATTTGACTGTCTCCGGCCTTTCTCACCCGTTTGAATC
TTTACCTACACATTACTCAGGCATTGCATTTAAAATATATGAGGGTTCTAAAAATTTT
TATCCTTGCGTTGAAATAAAGGCTTCTCCCGCAAAGTATTACAGGGTCATAATGTT
TTTGGTACAACCGATTTAGCTTTATGCTCTGAGGCTTTATTGCTTAATTTTGCTAATT
CTTTGCCTTGCCTGTATGATTTATTGGATGTTGGAAGTTCCTGATGCGGTATTTTCTC
CTTACGCATCTGTGCGGTATTTCACACCGCATATGGTGCACTCTCAGTACAATCTGCT
CTGATGCCGCATAGTTAAGCCAGCCCCGACACCCGCCAACACCCGCTGACGCGCCCT
GACGGGCTTGTCTGCTCCCGGCATCCGCTTACAGACAAGCTGTGACCGTCTCCGGGA
GCTGCATGTGTCAGAGGTTTTCACCGTCATCACCGAAACGCGCGAGACGAAAGGGC
CTCGTGATACGCCTATTTTTATAGGTTAATGTCATGATAATAATGGTTTCTTAGACGT
CAGGTGGCACTTTTCGGGGAAATGTGCGCGGAACCCCTATTTGTTTATTTTTCTAAAT
ACATTCAAATATGTATCCGCTCATGAGACAATAACCCTGATAAATGCTTCAATAATA
TTGAAAAAGGAAGAGTATGAGTATTCAACATTTCCGTGTCGCCCTTATTCCCTTTTTT
GCGGCATTTTGCCTTCCTGTTTTTGCTCACCCAGAAACGCTGGTGAAAGTAAAAGAT
GCTGAAGATCAGTTGGGTGCACGAGTGGGTTACATCGAACTGGATCTCAACAGCGG
TAAGATCCTTGAGAGTTTTCGCCCCGAAGAACGTT

Figure 22C

TTCCAATGATGAGCACTTTTAAAGTTCTGCTATGTGGCGCGGTATTATCCCGTATTGA
CGCCGGGCAAGAGCAACTCGGTCGCCGCATACACTATTCTCAGAATGACTTGGTTGA
GTACTCACCAGTCACAGAAAAGCATCTTACGGATGGCATGACAGTAAGAGAATTAT
GCAGTGCTGCCATAACCATGAGTGATAACACTGCGGCCAACTTACTTCTGACAACGA
TCGGAGGACCGAAGGAGCTAACCGCTTTTTGCACAACATGGGGGATCATGTAACTC
GCCTTGATCGTTGGGAACCGGAGCTGAATGAAGCCATACCAAACGACGAGCGTGAC
ACCACGATGCCTGTAGCAATGGCAACAACGTTGCGCAAACTATTAACTGGCGAACT
ACTTACTCTAGCTTCCCGGCAACAATTAATAGACTGGATGGAGGCGGATAAAGTTGC
AGGACCACTTCTGCGCTCGGCCCTTCCGGCTGGCTGGTTTATTGCTGATAAATCTGG
AGCCGGTGAGCGTGGGTCTCGCGGTATCATTGCAGCACTGGGGCCAGATGGTAAGC
CCTCCCGTATCGTAGTTATCTACACGACGGGGAGTCAGGCAACTATGGATGAACGA
AATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGA
TCTAGGTGAAGATCCTTTTTGATAATCTCATGACCAAAATCCCTTAACGTGAGTTTTC
GTTCCACTGAGCGTCAGACCCCGTAGAAAAGATCAAAGGATCTTCTTGAGATCCTTT
TTTTCTGCGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCTTCAGCAG
AGCGCAGATACCAAATACTGTCCTTCTAGTGTAGCCGTAGTTAGGCCACCACTTCAA
GAACTCTGTAGCACCGCGTACATACCTCGCTCTGCTAATCCTGTTACCAGTGGCTGC
TGCCAGTGGCGATAAGTCGTGTCTTACCGGGTTGGACTCAAGACGATAGTTACCGGA
TAAGGCGCAGCGGTCGGGCTGAACGGGGGGTTCGTGCACACAGCCCAGCTTGGAGC
GAACGACCTACACCGAACTGAGATACCTACAGCGTGAGCTATGAGAAAGCGCCACG
CTTCCCGAAGGGAGAAAGGCGGACAGGTATCCGGTAAGCGGCAGGGTCGGAACAG
GAGAGCGCACGAGGGAGCTTCCAGGGGGAAACGCCTGGTATCTTTATAGTCCTGTC
GGGTTTCGCCACCTCTGACTTGAGCGTCGATTTTGTGATGCTCGTCAGGGGGGCGG
AGCCTATGGAAAAACGCCAGCAACGCGGCCTTTTACGGTTCCTGGCCTTTTGCTGG
CCTTTTGCTCACATGTTCTTTCCTGCGTTATCCCCTGATTCTGTGGATAACCGTATTAC
CGGGTTTGAGTGAGCTGATACCGCTCGCCGCAGCCGAACGACCGAGCGCAGCGAGT
CAGTGAGCGACCAAGCGGAAGAGC

SEQUENCE LISTING

```
<160> NUMBER OF SEQ ID NOS: 13

<210> SEQ ID NO 1
<211> LENGTH: 5910
<212> TYPE: DNA
<213> ORGANISM: Adeno-associated virus
<220> FEATURE:
<221> NAME/KEY: promoter
<222> LOCATION: (120)..(526)
<223> OTHER INFORMATION: CMV promotor
<220> FEATURE:
<221> NAME/KEY: Intron
<222> LOCATION: (927)..(1087)
<223> OTHER INFORMATION: EF1a intron
<220> FEATURE:
<221> NAME/KEY: misc_feature
<222> LOCATION: (1088)..(1375)
<223> OTHER INFORMATION: shRNA-miR29-c
<220> FEATURE:
<221> NAME/KEY: misc_feature
<222> LOCATION: (1257)..(1284)
<223> OTHER INFORMATION: miR-29c
<220> FEATURE:
<221> NAME/KEY: Intron
<222> LOCATION: (1380)..(1854)
<223> OTHER INFORMATION: EF1a intron
<220> FEATURE:
<221> NAME/KEY: misc_feature
<222> LOCATION: (1896)..(2091)
<223> OTHER INFORMATION: polyA

<400> SEQUENCE: 1
cagcagctgc gcgctcgctc gctcactgag gccgcccggg caaagcccgg gcgtcgggcg      60
acctttggtc gcccggcctc agtgagcgag cgagcgcgca gagagggagt gggggttaaac    120 tcgttacata acttacggta aatggcccgc ctggctgacc gcccaacgac ccccgcccat     180
tgacgtcaat aatgacgtat gttcccatag taacgccaat agggactttc cattgacgtc     240
aatgggtgga gtatttacgg taaactgccc acttggcagt acatcaagtg tatcatatgc     300
caagtacgcc ccctattgac gtcaatgacg gtaaatggcc cgcctggcat tatgcccagt     360
acatgacctt atgggacttt cctacttggc agtacatcta cgtattagtc atcgctatta     420
ccatggtgat gcggttttgg cagtacatca atgggcgtgg atagcggttt gactcacggg     480
gatttccaag tctccacccc attgacgtca atgggagttt gttttggcac caaaatcaac     540
gggactttcc aaaatgtcgt aacaactccg ccccattgac gcaaatgggc ggtaggcgtg     600
```

```
tacggtggga ggtctatata agcagagctc gtttagtgaa ccgtcagatc gcctggagac    660
gccatccacg ctgttttgac ctccatagaa gacaccggga ccgatccagc ctccggactc    720
tagaggatcc ggtactcgag gaactgaaaa accagaaagt taactggtaa gtttagtctt    780
tttgtctttt atttcaggtc ccggatccgg tggtggtgca aatcaaagaa ctgctcctca    840
gtggatgttg cctttacttc taggcctgta cggaagtgtt acttctgctc taaaagctgc    900
ggaattgtac ccggggccga tccaccggtc ttttttcgca acgggtttgcc gccagaacac    960 aggtaagtgc cgtgtgtggt tcccgcgggc ggcgacgggg cccgtgcgtc ccagcgcaca   1020
tgttcggcga ggcggggcct gcgagcgcgg ccaccgagaa tcggacgggg gtagtctcaa   1080
gctggccggc ctgtttgaat gaggcttcag tactttacag aatcgttgcc tgcacatctt   1140
ggaaacactt gctgggatta cttcttcagg ttaacccaac agaaggctcg agaaggtata   1200
ttgctgttga cagtgagcgc aaccgatttc aaatggtgct agagtgaagc cacagatgtc   1260
tagcaccatt tgaaatcggt tatgcctact gcctcggaat tcaaggggct actttaggag   1320
caattatctt gtttactaaa actgaatacc ttgctatctc tttgatacat tggccggcct   1380
gctctggtgc ctggcctcgc gccgccgtgt atcgccccgc cctgggcggc aaggctggcc   1440
cggtcggcac cagttgcgtg agcggaaaga tggccgcttc ccggccctgc tgcagggagc   1500
tcaaaatgga ggacgcggcg ctcgggagag cgggcgggtg agtcacccac acaaaggaaa   1560
agggcctttc cgtcctcagc cgtcgcttca tgtgactcca cggagtaccg ggcgccgtcc   1620
aggcacctcg attagttctc gagcttttgg agtacgtcgt ctttaggttg ggggagggg   1680 ttttatgcga tggagtttcc ccacactgag tgggtggaga ctgaagttag gccagcttgg   1740
cacttgatgt aattctcctt ggaatttgcc cttttgagt ttggatcttg gttcattctc   1800
aagcctcaga cagtggttca agttttttt cttccatttc aggtgtcgtg aaaagctagc   1860
gctaccggac tcagatctcg agctcaagct gcggggatcc agacatgata agatacattg   1920
atgagtttgg acaaaccaca actagaatgc agtgaaaaaa atgctttatt tgtgaaattt   1980
gtgatgctat tgctttattt gtaaccatta taagctgcaa taaacaagtt aacaacaaca   2040
attgcattca ttttatgttt caggttcagg gggaggtgtg ggaggttttt tcactagtag   2100
catggctacg tagataagta gcatggcggg ttaatcatta actacaagga acccctagtg   2160
atggagttgg ccactccctc tctgcgcgct cgctcgctca ctgaggccgg gcgaccaaag   2220
gtcgcccgac gcccgggctt tgcccgggcg gcctcagtga gcgagcgagc gcgccagctg   2280
gcgtaatagc gaagaggccc gcaccgatcg cccttcccaa cagttgcgca gcctgaatgg   2340
cgaatggaat tccagacgat tgagcgtcaa aatgtaggta tttccatgag cgttttcct    2400 gttgcaatgg ctggcggtaa tattgttctg gatattacca gcaaggccga tagtttgagt   2460
tcttctactc aggcaagtga tgttattact aatcaaagaa gtattgcgac aacggttaat   2520
ttgcgtgatg gacagactct tttactcggt ggcctcactg attataaaaa cacttctcag   2580
gattctggcg taccgttcct gtctaaaatc cctttaatcg gcctcctgtt tagctcccgc   2640
tctgattcta acgaggaaag cacgttatac gtgctcgtca aagcaaccat agtacgcgcc   2700
ctgtagcggc gcattaagcg cggcgggtgt ggtggttacg cgcagcgtga ccgctacact   2760
tgccagcgcc ctagcgcccg ctcctttcgc tttcttccct tcctttctcg ccacgttcgc   2820
cggctttccc cgtcaagctc taaatcgggg ctccctttta gggttccgat ttagtgcttt   2880
acggcacctc gaccccaaaa aacttgatta gggtgatggt tcacgtagtg gccatcgcc    2940
```

-continued

```
ctgatagacg gttttttcgcc cttttgacgtt ggagtccacg ttctttaata gtggactctt      3000
gttccaaact ggaacaacac tcaaccctat ctcggtctat tcttttgatt tataagggat      3060
tttgccgatt tcggcctatt ggttaaaaaa tgagctgatt taacaaaaat ttaacgcgaa      3120
ttttaacaaa atattaacgt ttacaattta aatatttgct tatacaatct tcctgttttt      3180
ggggcttttc tgattatcaa ccggggtaca tatgattgac atgctagttt tacgattacc      3240
gttcatcgat tctcttgttt gctccagact ctcaggcaat gacctgatag cctttgtaga      3300
gacctctcaa aaatagctac cctctccggc atgaatttat cagctagaac ggttgaatat      3360
catattgatg gtgatttgac tgtctccggc ctttctcacc cgtttgaatc tttacctaca      3420
cattactcag gcattgcatt taaaatatat gagggttcta aaaattttta tccttgcgtt      3480
gaaataaagg cttctcccgc aaaagtatta cagggtcata tgttttttgg tacaaccgat      3540
ttagctttat gctctgaggc tttattgctt aattttgcta attctttgcc ttgcctgtat      3600
gatttattgg atgttggaat tcctgatgcg gtattttctc cttacgcatc tgtgcggtat      3660
ttcacaccgc atatggtgca ctctcagtac aatctgctct gatgccgcat agttaagcca      3720
gccccgacac ccgccaacac ccgctgacgc gccctgacgg gcttgtctgc tcccggcatc      3780
cgcttacaga caagctgtga ccgtctccgg gagctgcatg tgtcagaggt tttcaccgtc      3840
atcaccgaaa cgcgcgagac gaaagggcct cgtgatacgc ctatttttat aggttaatgt      3900
catgataata atggtttctt agacgtcagg tggcactttt cggggaaatg tgcgcggaac      3960
ccctatttgt ttatttttct aaatacattc aaatatgtat ccgctcatga gacaataacc      4020
ctgataaatg cttcaataat attgaaaaag gaagagtatg agtattcaac atttccgtgt      4080
cgcccttatt cccttttttg cggcattttg ccttcctgtt tttgctcacc cagaaacgct      4140
ggtgaaagta aaagatgctg aagatcagtt gggtgcacga gtgggttaca tcgaactgga      4200
tctcaacagc ggtaagatcc ttgagagttt tcgccccgaa gaacgttttc caatgatgag      4260
cacttttaaa gttctgctat gtggcgcggt attatcccgt attgacgccg ggcaagagca      4320
actcggtcgc cgcatacact attctcagaa tgacttggtt gagtactcac cagtcacaga      4380
aaagcatctt acggatggca tgacagtaag agaattatgc agtgctgcca taaccatgag      4440
tgataacact gcggccaact tacttctgac aacgatcgga ggaccgaagg agctaaccgc      4500
ttttttgcac aacatggggg atcatgtaac tcgccttgat cgttgggaac cggagctgaa      4560
tgaagccata ccaaacgacg agcgtgacac cacgatgcct gtagcaatgg caacaacgtt      4620
gcgcaaacta ttaactggcg aactacttac tctagcttcc cggcaacaat taatagactg      4680
gatggaggcg gataaagttg caggaccact tctgcgctcg gcccttccgg ctggctggtt      4740
tattgctgat aaatctggag ccggtgagcg tgggtctcgc ggtatcattg cagcactggg      4800
gccagatggt aagccctccc gtatcgtagt tatctacacg acggggagtc aggcaactat      4860
ggatgaacga aatagacaga tcgctgagat aggtgcctca ctgattaagc attggtaact      4920
gtcagaccaa gtttactcat atatacttta gattgattta aaacttcatt tttaatttaa      4980
aaggatctag gtgaagatcc tttttgataa tctcatgacc aaaatccctt aacgtgagtt      5040
ttcgttccac tgagcgtcag accccgtaga aaagatcaaa ggatcttctt gagatccttt      5100
ttttctgcgc gtaatctgct gcttgcaaac aaaaaaacca ccgctaccag cggtggtttg      5160
tttgccggat caagagctac caactctttt tccgaaggta actggcttca gcagagcgca      5220
gataccaaat actgtccttc tagtgtagcc gtagttaggc caccacttca agaactctgt      5280
agcaccgcct acatacctcg ctctgctaat cctgttacca gtggctgctg ccagtggcga      5340
```

```
taagtcgtgt cttaccgggt tggactcaag acgatagtta ccggataagg cgcagcggtc    5400
gggctgaacg gggggttcgt gcacacagcc cagcttggag cgaacgacct acaccgaact    5460
gagataccta cagcgtgagc tatgagaaag cgccacgctt cccgaaggga gaaaggcgga    5520
caggtatccg gtaagcggca gggtcggaac aggagagcgc acgagggagc ttccaggggg    5580
aaacgcctgg tatctttata gtcctgtcgg gtttcgccac ctctgacttg agcgtcgatt    5640
tttgtgatgc tcgtcagggg ggcggagcct atggaaaaac gccagcaacg cggcttttt     5700 acggttcctg gccttttgct ggccttttgc tcacatgttc tttcctgcgt tatcccctga    5760
ttctgtggat aaccgtatta ccgcctttga gtgagctgat accgctcgcc gcagccgaac    5820
gaccgagcgc agcgagtcag tgagcgagga gcggaagag cgcccaatac gcaaaccgcc     5880
tctccccgcg cgttggccga ttcattaatg                                     5910
```

<210> SEQ ID NO 2
<211> LENGTH: 296
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: FSE-I cut site
<220> FEATURE:
<221> NAME/KEY: misc_feature
<222> LOCATION: (9)..(136)
<223> OTHER INFORMATION: miR-30 backbone
<220> FEATURE:
<221> NAME/KEY: misc_feature
<222> LOCATION: (139)..(160)
<223> OTHER INFORMATION: miR-29c target (sense) strand
<220> FEATURE:
<221> NAME/KEY: misc_feature
<222> LOCATION: (161)..(175)
<223> OTHER INFORMATION: miR-29c target (sense) strand
<220> FEATURE:
<221> NAME/KEY: misc_feature
<222> LOCATION: (176)..(199)
<223> OTHER INFORMATION: miR-30 stem loop
<220> FEATURE:
<221> NAME/KEY: misc_feature
<222> LOCATION: (200)..(288)
<223> OTHER INFORMATION: miR-29c guide (antisense) strand
<220> FEATURE:
<221> NAME/KEY: misc_feature
<222> LOCATION: (289)..(296)
<223> OTHER INFORMATION: miR-30 backbone

<400> SEQUENCE: 2

```
ggccggcctg tttgaatgag gcttcagtac tttacagaat cgttgcctgc acatcttgga     60
aacacttgct gggattactt cttcaggtta acccaacaga aggctcgaga aggtatattg    120
ctgttgacag tgagcgcaac cgatttcaaa tggtgctaga gtgaagccac agatgtctag    180
caccatttga aatcggttat gcctactgcc tcggaattca aggggctact ttaggagcaa    240
ttatcttgtt tactaaaact gaataccttg ctatctcttt gatacattgg ccggcc        296
```

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 3

```
accgatttca aatggtgcta ga                                              22
```

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 4

```
tctagcacca tttgaaatcg gtta                                            24
```

<210> SEQ ID NO 5
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 5

```
gtgaagccac agatg                                                      15
```

<210> SEQ ID NO 6
<211> LENGTH: 98
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: miR-30 backbone
<220> FEATURE:
<221> NAME/KEY: misc_feature
<222> LOCATION: (20)..(42)
<223> OTHER INFORMATION: miR-29c target (sense) strand
<220> FEATURE:
<221> NAME/KEY: misc_feature
<222> LOCATION: (43)..(57)
<223> OTHER INFORMATION: miR-30 stem loop
<220> FEATURE:
<221> NAME/KEY: misc_feature
<222> LOCATION: (58)..(81)
<223> OTHER INFORMATION: miR-29c guide (antisense) strand
<220> FEATURE:
<221> NAME/KEY: misc_feature
<222> LOCATION: (82)..(98)
<223> OTHER INFORMATION: miR-30 backbone

<400> SEQUENCE: 6

```
ugcuguugac agugagcgca accgauuuca aauggugcua gagugaagcc acagaugucu     60
agcaccauuu gaaaucgguu augccuacug ccucggaa                             98
```

<210> SEQ ID NO 7
<211> LENGTH: 3581
<212> TYPE: DNA
<213> ORGANISM: Homo sapiens
<220> FEATURE:
<221> NAME/KEY: CDS
<222> LOCATION: (1)..(3579)

<400> SEQUENCE: 7

```
atg ctg tgg tgg gag gag gtg gag gat tgt tat gaa agg gag gac gtg      48
Met Leu Trp Trp Glu Glu Val Glu Asp Cys Tyr Glu Arg Glu Asp Val
1               5                   10                  15 cag aag aag act ttt acc aag tgg gtg aac gct cag ttc agc aaa ttt      96
Gln Lys Lys Thr Phe Thr Lys Trp Val Asn Ala Gln Phe Ser Lys Phe
            20                  25                  30
```

| | | |
|---|---|---|
| ggg aag cag cac atc gag aat ctg ttt tcc gac ctg cag gat ggg aga<br>Gly Lys Gln His Ile Glu Asn Leu Phe Ser Asp Leu Gln Asp Gly Arg<br>35 40 45 | 144 | |
| cgg ctg ctg gat ctg ctg gaa gga ctg act ggc cag aag ctg ccc aaa<br>Arg Leu Leu Asp Leu Leu Glu Gly Leu Thr Gly Gln Lys Leu Pro Lys<br>50 55 60 | 192 | |
| gag aag ggg agc act agg gtg cac gcc ctg aac aac gtg aac aaa gct<br>Glu Lys Gly Ser Thr Arg Val His Ala Leu Asn Asn Val Asn Lys Ala<br>65 70 75 80 | 240 | |
| ctg aga gtg ctg cag aac aac aac gtg gat ctg gtg aat att ggc agt<br>Leu Arg Val Leu Gln Asn Asn Asn Val Asp Leu Val Asn Ile Gly Ser<br>85 90 95 | 288 | |
| act gat atc gtg gac ggg aac cac aaa ctg aca ctg ggc ctg atc tgg<br>Thr Asp Ile Val Asp Gly Asn His Lys Leu Thr Leu Gly Leu Ile Trp<br>100 105 110 | 336 | |
| aac att att ctg cac tgg cag gtg aaa aat gtg atg aag aac atc atg<br>Asn Ile Ile Leu His Trp Gln Val Lys Asn Val Met Lys Asn Ile Met<br>115 120 125 | 384 | |
| gcc ggg ctg cag cag acc aat tcc gag aag atc ctg ctg tct tgg gtg<br>Ala Gly Leu Gln Gln Thr Asn Ser Glu Lys Ile Leu Leu Ser Trp Val<br>130 135 140 | 432 | |
| cgg cag agc acc cgc aac tat ccc cag gtg aac gtg att aac ttc act<br>Arg Gln Ser Thr Arg Asn Tyr Pro Gln Val Asn Val Ile Asn Phe Thr<br>145 150 155 160 | 480 | |
| aca tcc tgg agc gac ggg ctg gcc ctg aat gct ctg att cac agc cac<br>Thr Ser Trp Ser Asp Gly Leu Ala Leu Asn Ala Leu Ile His Ser His<br>165 170 175 | 528 | |
| agg cct gat ctg ttc gac tgg aat agc gtg gtg tgc cag cag tct gcc<br>Arg Pro Asp Leu Phe Asp Trp Asn Ser Val Val Cys Gln Gln Ser Ala<br>180 185 190 | 576 | |
| aca cag cgc ctg gaa cat gcc ttc aat atc gct cgg tac cag ctg ggg<br>Thr Gln Arg Leu Glu His Ala Phe Asn Ile Ala Arg Tyr Gln Leu Gly<br>195 200 205 | 624 | |
| atc gaa aaa ctg ctg gac cca gag gat gtg gac act aca tac cca gat<br>Ile Glu Lys Leu Leu Asp Pro Glu Asp Val Asp Thr Thr Tyr Pro Asp<br>210 215 220 | 672 | |
| aaa aag tct att ctg atg tac att act agc ctg ttc cag gtg ctg cca<br>Lys Lys Ser Ile Leu Met Tyr Ile Thr Ser Leu Phe Gln Val Leu Pro<br>225 230 235 240 | 720 | |
| cag cag gtg tct att gaa gcc att cag gag gtg gaa atg ctg ccc cgc<br>Gln Gln Val Ser Ile Glu Ala Ile Gln Glu Val Glu Met Leu Pro Arg<br>245 250 255 | 768 | |
| ccc ccc aaa gtg act aaa gag gag cat ttt cag ctg cat cat cag atg<br>Pro Pro Lys Val Thr Lys Glu Glu His Phe Gln Leu His His Gln Met<br>260 265 270 | 816 | |
| cat tac agc cag cag att acc gtg agc ctg gct cag gga tat gag cgc<br>His Tyr Ser Gln Gln Ile Thr Val Ser Leu Ala Gln Gly Tyr Glu Arg<br>275 280 285 | 864 | |
| acc agt agt cca aaa cca cgg ttc aag tcc tac gct tat acc cag gct<br>Thr Ser Ser Pro Lys Pro Arg Phe Lys Ser Tyr Ala Tyr Thr Gln Ala<br>290 295 300 | 912 | |
| gcc tac gtg aca act agc gac cct act aga tcc ccc ttt cca tcc cag<br>Ala Tyr Val Thr Thr Ser Asp Pro Thr Arg Ser Pro Phe Pro Ser Gln<br>305 310 315 320 | 960 | |
| cac ctg gag gcc cca gag gac aag agc ttt ggg tcc agc ctg atg gaa<br>His Leu Glu Ala Pro Glu Asp Lys Ser Phe Gly Ser Ser Leu Met Glu<br>325 330 335 | 1008 | |
| agc gag gtg aat ctg gat cgg tac cag aca gcc ctg gag gag gtg ctg<br>Ser Glu Val Asn Leu Asp Arg Tyr Gln Thr Ala Leu Glu Glu Val Leu<br>340 345 350 | 1056 | |

```
agc tgg ctg ctg agt gct gaa gac aca ctg cag gcc cag ggc gaa att    1104
Ser Trp Leu Leu Ser Ala Glu Asp Thr Leu Gln Ala Gln Gly Glu Ile
        355                 360                 365 tcc aat gac gtg gaa gtg gtg aag gat cag ttc cac aca cac gag ggc    1152
Ser Asn Asp Val Glu Val Val Lys Asp Gln Phe His Thr His Glu Gly
370                 375                 380 tat atg atg gac ctg aca gct cac cag ggg cgc gtg ggc aat atc ctg    1200
Tyr Met Met Asp Leu Thr Ala His Gln Gly Arg Val Gly Asn Ile Leu
385                 390                 395                 400 cag ctg ggc tct aaa ctg atc ggc acc ggg aaa ctg agt gag gac gag    1248
Gln Leu Gly Ser Lys Leu Ile Gly Thr Gly Lys Leu Ser Glu Asp Glu
            405                 410                 415 gaa aca gaa gtg cag gag cag atg aac ctg ctg aac agc cgc tgg gag    1296
Glu Thr Glu Val Gln Glu Gln Met Asn Leu Leu Asn Ser Arg Trp Glu
        420                 425                 430 tgt ctg aga gtg gct agt atg gag aag cag tcc aac ctg cac cgg gtg    1344
Cys Leu Arg Val Ala Ser Met Glu Lys Gln Ser Asn Leu His Arg Val
        435                 440                 445 ctg atg gac ctg cag aac cag aaa ctg aaa gag ctg aac gac tgg ctg    1392
Leu Met Asp Leu Gln Asn Gln Lys Leu Lys Glu Leu Asn Asp Trp Leu
450                 455                 460 aca aag act gag gaa cgc aca agg aag atg gag gag gag cca ctg gga    1440
Thr Lys Thr Glu Glu Arg Thr Arg Lys Met Glu Glu Glu Pro Leu Gly
465                 470                 475                 480 ccc gac ctg gag gat ctg aag aga cag gtg cag cag cat aag gtg ctg    1488
Pro Asp Leu Glu Asp Leu Lys Arg Gln Val Gln Gln His Lys Val Leu
            485                 490                 495 cag gag gat ctg gaa cag gag cag gtg cgg gtg aac tcc ctg aca cat    1536
Gln Glu Asp Leu Glu Gln Glu Gln Val Arg Val Asn Ser Leu Thr His
        500                 505                 510 atg gtg gtg gtg gac gaa tct agt gga gat cac gcc acc gcc gcc       1584
Met Val Val Val Asp Glu Ser Ser Gly Asp His Ala Thr Ala Ala
        515                 520                 525 ctg gag gaa cag ctg aag gtg ctg ggg gac cgg tgg gcc aac att tgc    1632
Leu Glu Glu Gln Leu Lys Val Leu Gly Asp Arg Trp Ala Asn Ile Cys
530                 535                 540 cgg tgg acc gag gac agg tgg gtg ctg ctg cag gac atc ctg ctg aaa    1680
Arg Trp Thr Glu Asp Arg Trp Val Leu Leu Gln Asp Ile Leu Leu Lys
545                 550                 555                 560 tgg cag agg ctg acc gag gag cag tgt ctg ttt agt gct tgg ctg agc    1728
Trp Gln Arg Leu Thr Glu Glu Gln Cys Leu Phe Ser Ala Trp Leu Ser
            565                 570                 575 gag aaa gag gac gcc gtg aac aag atc cac aca acc ggc ttt aag gat    1776
Glu Lys Glu Asp Ala Val Asn Lys Ile His Thr Thr Gly Phe Lys Asp
        580                 585                 590 cag aac gaa atg ctg tct agc ctg cag aaa ctg gct gtg ctg aag gcc    1824
Gln Asn Glu Met Leu Ser Ser Leu Gln Lys Leu Ala Val Leu Lys Ala
        595                 600                 605 gat ctg gag aaa aag aag cag agc atg ggc aaa ctg tat agc ctg aaa    1872
Asp Leu Glu Lys Lys Lys Gln Ser Met Gly Lys Leu Tyr Ser Leu Lys
        610                 615                 620 cag gac ctg ctg agc acc ctg aag aac aag agc gtg acc cag aag aca    1920
Gln Asp Leu Leu Ser Thr Leu Lys Asn Lys Ser Val Thr Gln Lys Thr
625                 630                 635                 640 gaa gcc tgg ctg gat aac ttt gcc cgc tgc tgg gac aac ctg gtg cag    1968
Glu Ala Trp Leu Asp Asn Phe Ala Arg Cys Trp Asp Asn Leu Val Gln
                645                 650                 655 aaa ctg gag aaa agt aca gct cag atc tct cag gct gtg acc aca acc    2016
Lys Leu Glu Lys Ser Thr Ala Gln Ile Ser Gln Ala Val Thr Thr Thr
```

-continued

```
                660                 665                 670
cag cct agc ctg acc cag aca acc gtg atg gaa acc gtg acc acc gtg        2064
Gln Pro Ser Leu Thr Gln Thr Thr Val Met Glu Thr Val Thr Thr Val
            675                 680                 685 aca acc cgc gaa cag atc ctg gtg aaa cat gcc cag gaa gag ctg cca        2112
Thr Thr Arg Glu Gln Ile Leu Val Lys His Ala Gln Glu Glu Leu Pro
690                 695                 700 cct cca cct ccc cag aag aag aga acc ctg gag cgg ctg cag gag ctg        2160
Pro Pro Pro Pro Gln Lys Lys Arg Thr Leu Glu Arg Leu Gln Glu Leu
705                 710                 715                 720 cag gaa gcc act gac gaa ctg gac ctg aag ctg agg cag gcc gaa gtg        2208
Gln Glu Ala Thr Asp Glu Leu Asp Leu Lys Leu Arg Gln Ala Glu Val
                725                 730                 735 att aag ggg tct tgg cag cct gtg ggc gat ctg ctg att gat tcc ctg        2256
Ile Lys Gly Ser Trp Gln Pro Val Gly Asp Leu Leu Ile Asp Ser Leu
            740                 745                 750 cag gac cac ctg gaa aag gtg aag gct ctg aga ggc gaa att gct cca        2304
Gln Asp His Leu Glu Lys Val Lys Ala Leu Arg Gly Glu Ile Ala Pro
        755                 760                 765 ctg aag gag aac gtg agt cat gtg aac gat ctg gct aga cag ctg aca        2352
Leu Lys Glu Asn Val Ser His Val Asn Asp Leu Ala Arg Gln Leu Thr
770                 775                 780 aca ctg ggc atc cag ctg agc cca tac aat ctg agc aca ctg gag gac        2400
Thr Leu Gly Ile Gln Leu Ser Pro Tyr Asn Leu Ser Thr Leu Glu Asp
785                 790                 795                 800 ctg aat acc agg tgg aag ctg ctg cag gtg gct gtg gaa gac cgg gtg        2448
Leu Asn Thr Arg Trp Lys Leu Leu Gln Val Ala Val Glu Asp Arg Val
                805                 810                 815 cgg cag ctg cat gag gcc cat cgc gac ttc gga cca gcc agc cag cac        2496
Arg Gln Leu His Glu Ala His Arg Asp Phe Gly Pro Ala Ser Gln His
            820                 825                 830 ttt ctg agc aca tcc gtg cag ggg ccc tgg gag agg gcc att tct ccc        2544
Phe Leu Ser Thr Ser Val Gln Gly Pro Trp Glu Arg Ala Ile Ser Pro
        835                 840                 845 aac aag gtg ccc tac tat att aat cac gag acc cag acc act tgt tgg        2592
Asn Lys Val Pro Tyr Tyr Ile Asn His Glu Thr Gln Thr Thr Cys Trp
850                 855                 860 gac cat ccc aag atg aca gaa ctg tac cag tcc ctg gcc gat ctg aac        2640
Asp His Pro Lys Met Thr Glu Leu Tyr Gln Ser Leu Ala Asp Leu Asn
865                 870                 875                 880 aac gtg agg ttt agc gct tac aga acc gct atg aag ctg aga cgg ctg        2688
Asn Val Arg Phe Ser Ala Tyr Arg Thr Ala Met Lys Leu Arg Arg Leu
                885                 890                 895 cag aag gcc ctg tgc ctg gat ctg ctg tcc ctg tcc gcc gcc tgc gat        2736
Gln Lys Ala Leu Cys Leu Asp Leu Leu Ser Leu Ser Ala Ala Cys Asp
            900                 905                 910 gcc ctg gat cag cat aat ctg aag cag aac gat cag cca atg gat atc        2784
Ala Leu Asp Gln His Asn Leu Lys Gln Asn Asp Gln Pro Met Asp Ile
        915                 920                 925 ctg cag atc atc aac tgc ctg acc act atc tac gac agg ctg gag cag        2832
Leu Gln Ile Ile Asn Cys Leu Thr Thr Ile Tyr Asp Arg Leu Glu Gln
930                 935                 940 gag cac aac aac ctg gtg aac gtg cct ctg tgc gtg gat atg tgc ctg        2880
Glu His Asn Asn Leu Val Asn Val Pro Leu Cys Val Asp Met Cys Leu
945                 950                 955                 960 aac tgg ctg ctg aac gtg tat gac act ggg cgc acc ggc cgg atc aga        2928
Asn Trp Leu Leu Asn Val Tyr Asp Thr Gly Arg Thr Gly Arg Ile Arg
                965                 970                 975 gtg ctg agt ttt aaa act ggg att atc tcc ctg tgt aag gcc cac ctg        2976
```

```
Val Leu Ser Phe Lys Thr Gly Ile Ile Ser Leu Cys Lys Ala His Leu
            980                 985                 990 gag gac aag tac agg tac ctg ttc aag cag gtg gct agt agc act gga    3024
Glu Asp Lys Tyr Arg Tyr Leu Phe Lys Gln Val Ala Ser Ser Thr Gly
            995                 1000                1005 ttt tgt gac cag cgc cgc ctg gga ctg ctg ctg cat gat agt atc        3069
Phe Cys Asp Gln Arg Arg Leu Gly Leu Leu Leu His Asp Ser Ile
        1010                1015                1020 cag att cct aga cag ctg gga gag gtg gct agt ttc gga gga tct        3114
Gln Ile Pro Arg Gln Leu Gly Glu Val Ala Ser Phe Gly Gly Ser
        1025                1030                1035 aac atc gaa ccc agc gtg cgc agc tgt ttc cag ttt gcc aat aac        3159
Asn Ile Glu Pro Ser Val Arg Ser Cys Phe Gln Phe Ala Asn Asn
        1040                1045                1050 aaa cct gaa atc gag gct gct ctg ttc ctg gat tgg atg cgc ctg        3204
Lys Pro Glu Ile Glu Ala Ala Leu Phe Leu Asp Trp Met Arg Leu
        1055                1060                1065 gaa cca cag agc atg gtg tgg ctg cct gtg ctg cac aga gtg gct        3249
Glu Pro Gln Ser Met Val Trp Leu Pro Val Leu His Arg Val Ala
        1070                1075                1080 gcc gcc gaa act gcc aag cac cag gct aaa tgc aac atc tgc aag        3294
Ala Ala Glu Thr Ala Lys His Gln Ala Lys Cys Asn Ile Cys Lys
        1085                1090                1095 gaa tgt ccc att atc ggc ttt cgc tac agg agt ctg aaa cat ttt        3339
Glu Cys Pro Ile Ile Gly Phe Arg Tyr Arg Ser Leu Lys His Phe
        1100                1105                1110 aac tac gat att tgc cag agc tgc ttc ttt tcc gga aga gtg gcc        3384
Asn Tyr Asp Ile Cys Gln Ser Cys Phe Phe Ser Gly Arg Val Ala
        1115                1120                1125 aaa gga cac aag atg cac tac cct atg gtg gaa tat tgc acc cca        3429
Lys Gly His Lys Met His Tyr Pro Met Val Glu Tyr Cys Thr Pro
        1130                1135                1140 act aca tct ggc gaa gat gtg cgc gat ttt gcc aag gtg ctg aag        3474
Thr Thr Ser Gly Glu Asp Val Arg Asp Phe Ala Lys Val Leu Lys
        1145                1150                1155 aat aag ttt cgg act aag agg tac ttc gcc aag cac ccc cgc atg        3519
Asn Lys Phe Arg Thr Lys Arg Tyr Phe Ala Lys His Pro Arg Met
        1160                1165                1170 ggg tat ctg cca gtg cag aca gtg ctg gaa gga gac aat atg gag        3564
Gly Tyr Leu Pro Val Gln Thr Val Leu Glu Gly Asp Asn Met Glu
        1175                1180                1185 acc gat aca atg tga gc                                              3581
Thr Asp Thr Met
        1190

<210> SEQ ID NO 8
<211> LENGTH: 1192
<212> TYPE: PRT
<213> ORGANISM: Homo sapiens

<400> SEQUENCE: 8

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60
```

-continued

Glu Lys Gly Ser Thr Arg Val His Ala Leu Asn Asn Val Asn Lys Ala
65                  70                  75                  80

Leu Arg Val Leu Gln Asn Asn Val Asp Leu Val Asn Ile Gly Ser
            85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
            115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
            165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
    195                 200                 205

Ile Glu Lys Leu Leu Asp Pro Glu Asp Val Asp Thr Thr Tyr Pro Asp
210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Val Glu Met Leu Pro Arg
            245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
    275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
            325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
    355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
            405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
            435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Pro Leu Gly
465                 470                 475                 480

Pro Asp Leu Glu Asp Leu Lys Arg Gln Val Gln Gln His Lys Val Leu

```
                485                 490                 495
Gln Glu Asp Leu Glu Gln Glu Gln Val Arg Val Asn Ser Leu Thr His
            500                 505                 510
Met Val Val Val Asp Glu Ser Ser Gly Asp His Ala Thr Ala Ala
            515                 520                 525
Leu Glu Glu Gln Leu Lys Val Leu Gly Asp Arg Trp Ala Asn Ile Cys
            530                 535                 540
Arg Trp Thr Glu Asp Arg Trp Val Leu Leu Gln Asp Ile Leu Leu Lys
545                 550                 555                 560
Trp Gln Arg Leu Thr Glu Glu Gln Cys Leu Phe Ser Ala Trp Leu Ser
                565                 570                 575
Glu Lys Glu Asp Ala Val Asn Lys Ile His Thr Thr Gly Phe Lys Asp
            580                 585                 590
Gln Asn Glu Met Leu Ser Ser Leu Gln Lys Leu Ala Val Leu Lys Ala
            595                 600                 605
Asp Leu Glu Lys Lys Lys Gln Ser Met Gly Lys Leu Tyr Ser Leu Lys
            610                 615                 620
Gln Asp Leu Leu Ser Thr Leu Lys Asn Lys Ser Val Thr Gln Lys Thr
625                 630                 635                 640
Glu Ala Trp Leu Asp Asn Phe Ala Arg Cys Trp Asp Asn Leu Val Gln
                645                 650                 655
Lys Leu Glu Lys Ser Thr Ala Gln Ile Ser Gln Ala Val Thr Thr Thr
            660                 665                 670
Gln Pro Ser Leu Thr Gln Thr Thr Val Met Glu Thr Val Thr Thr Val
            675                 680                 685
Thr Thr Arg Glu Gln Ile Leu Val Lys His Ala Gln Glu Glu Leu Pro
690                 695                 700
Pro Pro Pro Pro Gln Lys Lys Arg Thr Leu Glu Arg Leu Gln Glu Leu
705                 710                 715                 720
Gln Glu Ala Thr Asp Glu Leu Asp Leu Lys Leu Arg Gln Ala Glu Val
                725                 730                 735
Ile Lys Gly Ser Trp Gln Pro Val Gly Asp Leu Leu Ile Asp Ser Leu
            740                 745                 750
Gln Asp His Leu Glu Lys Val Lys Ala Leu Arg Gly Glu Ile Ala Pro
            755                 760                 765
Leu Lys Glu Asn Val Ser His Val Asn Asp Leu Ala Arg Gln Leu Thr
            770                 775                 780
Thr Leu Gly Ile Gln Leu Ser Pro Tyr Asn Leu Ser Thr Leu Glu Asp
785                 790                 795                 800
Leu Asn Thr Arg Trp Lys Leu Leu Gln Val Ala Val Glu Asp Arg Val
                805                 810                 815
Arg Gln Leu His Glu Ala His Arg Asp Phe Gly Pro Ala Ser Gln His
            820                 825                 830
Phe Leu Ser Thr Ser Val Gln Gly Pro Trp Glu Arg Ala Ile Ser Pro
            835                 840                 845
Asn Lys Val Pro Tyr Tyr Ile Asn His Glu Thr Gln Thr Thr Cys Trp
            850                 855                 860
Asp His Pro Lys Met Thr Glu Leu Tyr Gln Ser Leu Ala Asp Leu Asn
865                 870                 875                 880
Asn Val Arg Phe Ser Ala Tyr Arg Thr Ala Met Lys Leu Arg Arg Leu
                885                 890                 895
Gln Lys Ala Leu Cys Leu Asp Leu Leu Ser Leu Ser Ala Ala Cys Asp
            900                 905                 910
```

```
Ala Leu Asp Gln His Asn Leu Lys Gln Asn Asp Gln Pro Met Asp Ile
        915                 920                 925

Leu Gln Ile Ile Asn Cys Leu Thr Thr Ile Tyr Asp Arg Leu Glu Gln
    930                 935                 940

Glu His Asn Asn Leu Val Asn Val Pro Leu Cys Val Asp Met Cys Leu
945                 950                 955                 960

Asn Trp Leu Leu Asn Val Tyr Asp Thr Gly Arg Thr Gly Arg Ile Arg
            965                 970                 975

Val Leu Ser Phe Lys Thr Gly Ile Ile Ser Leu Cys Lys Ala His Leu
            980                 985                 990

Glu Asp Lys Tyr Arg Tyr Leu Phe Lys Gln Val Ala Ser  Ser Thr Gly
            995                 1000                 1005

Phe Cys Asp Gln Arg Arg Leu  Gly Leu Leu His  Asp Ser Ile
    1010                1015                1020

Gln Ile Pro Arg Gln Leu Gly  Glu Val Ala Ser  Phe Gly Gly Ser
    1025                1030                1035

Asn Ile Glu Pro Ser Val Arg  Ser Cys Phe Gln  Phe Ala Asn Asn
    1040                1045                1050

Lys Pro Glu Ile Glu Ala Ala  Leu Phe Leu Asp  Trp Met Arg Leu
    1055                1060                1065

Glu Pro Gln Ser Met Val Trp  Leu Pro Val Leu  His Arg Val Ala
    1070                1075                1080

Ala Ala Glu Thr Ala Lys His  Gln Ala Lys Cys  Asn Ile Cys Lys
    1085                1090                1095

Glu Cys Pro Ile Ile Gly Phe  Arg Tyr Arg Ser  Leu Lys His Phe
    1100                1105                1110

Asn Tyr Asp Ile Cys Gln Ser  Cys Phe Phe Ser  Gly Arg Val Ala
    1115                1120                1125

Lys Gly His Lys Met His Tyr  Pro Met Val Glu  Tyr Cys Thr Pro
    1130                1135                1140

Thr Thr Ser Gly Glu Asp Val  Arg Asp Phe Ala Lys  Val Leu Lys
    1145                1150                1155

Asn Lys Phe Arg Thr Lys Arg  Tyr Phe Ala Lys  His Pro Arg Met
    1160                1165                1170

Gly Tyr Leu Pro Val Gln Thr  Val Leu Glu Gly  Asp Asn Met Glu
    1175                1180                1185

Thr Asp Thr Met
    1190

<210> SEQ ID NO 9
<211> LENGTH: 8409
<212> TYPE: DNA
<213> ORGANISM: Adeno-associated virus
<220> FEATURE:
<221> NAME/KEY: promoter
<222> LOCATION: (236)..(799)
<223> OTHER INFORMATION: MCK promotor
<220> FEATURE:
<221> NAME/KEY: Intron
<222> LOCATION: (844)..(993)
<223> OTHER INFORMATION: Chimeric intron sequence
<220> FEATURE:
<221> NAME/KEY: misc_feature
<222> LOCATION: (1004)..(4584)
<223> OTHER INFORMATION: Human Dystrophin sequence
<220> FEATURE:
<221> NAME/KEY: misc_feature
<222> LOCATION: (4585)..(4640)
<223> OTHER INFORMATION: Poly A tail
```

```
<220> FEATURE:
<221> NAME/KEY: misc_feature
<222> LOCATION: (6606)..(7466)
<223> OTHER INFORMATION: Ampicillin resistance
<220> FEATURE:
<221> NAME/KEY: misc_feature
<222> LOCATION: (7621)..(8240)
<223> OTHER INFORMATION: pGEX plasmid backbone with pBR322 origin or
      replication

<400> SEQUENCE: 9
gcccaatacg caaaccgcct ctccccgcgc gttggccgat tcattaatgc agctggcgcg    60
ctcgctcgct cactgaggcc gcccgggcaa agcccgggcg tcgggcgacc tttggtcgcc   120
cggcctcagt gagcgagcga gcgcgcagag agggagtggc caactccatc actagggtt   180 ccttgtagtt aatgattaac ccgccatgct aattatctac gtagccatgt ctagacagcc   240
actatgggtc taggctgccc atgtaaggag gcaaggcctg ggacacccg agatgcctgg    300 ttataattaa cccagacatg tggctgctcc ccccccccaa cacctgctgc ctgagcctca   360
cccccacccc ggtgcctggg tcttaggctc tgtacaccat ggaggagaag ctcgctctaa   420
aaataaccct gtccctggtg ggctgtgggg gactgagggc aggctgtaac aggcttgggg   480
gccagggctt atacgtgcct gggactccca agtattact gttccatgtt cccggcgaag    540
ggccagctgt cccccgccag ctagactcag cacttagttt aggaaccagt gagcaagtca   600
gcccttgggg cagcccatac aaggccatgg ggctgggcaa gctgcacgcc tgggtccggg   660
gtgggcacgg tgcccgggca acgagctgaa agctcatctg ctctcagggg cccctccctg   720
gggacagccc ctcctggcta gtcacaccct gtaggctcct ctatataacc caggggcaca   780
ggggctgccc ccgggtcacc accacctcca cagcacagac agacactcag gagccagcca   840
gccaggtaag tttagtcttt ttgtctttta tttcaggtcc cggatccggt ggtggtgcaa   900
atcaaagaac tgctcctcag tggatgttgc ctttacttct aggcctgtac ggaagtgtta   960
cttctgctct aaaagctgcg gaattgtacc cgcggccgcc accatgctgt ggtgggagga  1020
ggtggaggat tgttatgaaa gggaggacgt gcagaagaag acttttacca agtgggtgaa  1080
cgctcagttc agcaaatttg gaagcagca catcgagaat ctgttttccg acctgcagga   1140
tgggagacgg ctgctggatc tgctggaagg actgactggc cagaagctgc ccaaagagaa  1200
ggggagcact agggtgcacg ccctgaacaa cgtgaacaaa gctctgagag tgctgcagaa  1260
caacaacgtg gatctggtga atattggcag tactgatatc gtggacggga accacaaact  1320
gacactgggc ctgatctgga acattattct gcactggcag gtgaaaaatg tgatgaagaa  1380
catcatggcc gggctgcagc agaccaattc cgagaagatc ctgctgtctt gggtgcggca  1440
gagcacccgc aactatcccc aggtgaacgt gattaacttc actacatcct ggagcgacgg  1500
gctggccctg aatgctctga ttcacagcca caggcctgat ctgttcgact ggaatagcgt  1560
ggtgtgccag cagtctgcca cacagcgcct ggaacatgcc ttcaatatcg ctcggtacca  1620 gctgggatc gaaaaactgc tggacccaga ggatgtggac actacatacc cagataaaaa    1680
gtctattctg atgtacatta ctagcctgtt ccaggtgctg ccacagcagg tgtctattga  1740
agccattcag gaggtggaaa tgctgccccg cccccccaaa gtgactaaag aggagcattt  1800
tcagctgcat catcagatgc attacagcca gcagattacc gtgagcctgg ctcagggata  1860
tgagcgcacc agtagtccaa aaccacggtt caagtcctac gcttatacccc aggctgccta  1920 cgtgacaact agcgacccta ctagatcccc ctttccatcc cagcacctgg aggccccaga  1980
ggacaagagc tttgggtcca gcctgatgga aagcgaggtg aatctggatc ggtaccagac  2040
```

```
agccctggag gaggtgctga gctggctgct gagtgctgaa gacacactgc aggcccaggg    2100
cgaaatttcc aatgacgtgg aagtggtgaa ggatcagttc cacacacacg agggctatat    2160
gatggacctg acagctcacc aggggcgcgt gggcaatatc ctgcagctgg gctctaaact    2220
gatcggcacc gggaaactga gtgaggacga ggaaacagaa gtgcaggagc agatgaacct    2280
gctgaacagc cgctgggagt gtctgagagt ggctagtatg gagaagcagt ccaacctgca    2340
ccgggtgctg atggacctgc agaaccagaa actgaaagag ctgaacgact ggctgacaaa    2400
gactgaggaa cgcacaagga agatggagga ggagccactg ggacccgacc tggaggatct    2460
gaagagacag gtgcagcagc ataaggtgct gcaggaggat ctggaacagg agcaggtgcg    2520
ggtgaactcc ctgacacata tggtggtggt ggtggacgaa tctagtggag atcacgccac    2580
cgccgccctg gaggaacagc tgaaggtgct ggggaccgg tgggccaaca tttgccggtg    2640
gaccgaggac aggtgggtgc tgctgcagga catcctgctg aaatggcaga ggctgaccga    2700
ggagcagtgt ctgtttagtg cttggctgag cgagaaagag gacgccgtga acaagatcca    2760
cacaaccggc tttaaggatc agaacgaaat gctgtctagc ctgcagaaac tggctgtgct    2820
gaaggccgat ctggagaaaa agaagcagag catgggcaaa ctgtatagcc tgaaacagga    2880
cctgctgagc accctgaaga caagagcgt gacccagaag acagaagcct ggctggataa    2940 cttttgcccgc tgctgggaca acctggtgca gaaactggag aaaagtacag ctcagatctc    3000
tcaggctgtg accacaaccc agcctagcct gacccagaca accgtgatgg aaaccgtgac    3060
caccgtgaca acccgcgaac agatcctggt gaaacatgcc caggaagagc tgccacctcc    3120
acctccccag aagaagagaa ccctggagcg gctgcaggag ctgcaggaag ccactgacga    3180
actggacctg aagctgaggc aggccgaagt gattaagggg tcttggcagc tgtgggcga    3240 tctgctgatt gattccctgc aggaccacct ggaaaaggtg aaggctctga gaggcgaaat    3300
tgctccactg aaggagaacg tgagtcatgt gaacgatctg ctagacagc tgacaacact    3360 gggcatccag ctgagcccat acaatctgag cacactggag gacctgaata ccaggtggaa    3420
gctgctgcag gtggctgtgg aagacccggg gcggcagctg catgaggccc atcgcgactt    3480
cggaccagcc agccagcact ttctgagcac atccgtgcag gggccctggg agagggccat    3540
ttctcccaac aaggtgccct actatattaa tcacgagacc cagaccactt gttgggacca    3600
tcccaagatg acagaactgt accagtccct ggccgatctg aacaacgtga ggtttagcgc    3660
ttacagaacc gctatgaagc tgagacggct gcagaaggcc ctgtgcctgg atctgctgtc    3720
cctgtccgcc gcctgcgatg ccctggatca gcataatctg aagcagaacg atcagccaat    3780
ggatatcctg cagatcatca actgcctgac cactatctac gacaggctgg agcaggagca    3840
caacaacctg gtgaacgtgc ctctgtgcgt ggatatgtgc ctgaactggc tgctgaacgt    3900
gtatgacact gggcgcaccg gccggatcag agtgctgagt tttaaaactg ggattatctc    3960
cctgtgtaag gccacctgg aggacaagta caggtacctg ttcaagcagg tggctagtag    4020
cactggattt tgtgaccagc gccgcctggg actgctgctg catgatagta ccagattcc    4080 tagacagctg ggagaggtgg ctagtttcgg aggatctaac atcgaaccca gcgtgcgcag    4140
ctgtttccag tttgccaata acaaacctga aatcgaggct gctctgttcc tggattggat    4200
gcgcctggaa ccacagagca tggtgtggct gcctgtgctg cacagagtgg ctgccgccga    4260
aactgccaag caccaggcta aatgcaacat ctgcaaggaa tgtcccatta tcggcttcg    4320 ctacaggagt ctgaaacatt ttaactacga tatttgccag agctgcttct tttccggaag    4380
```

```
agtggccaaa ggacacaaga tgcactaccc tatggtggaa tattgcaccc caactacatc   4440
tggcgaagat gtgcgcgatt ttgccaaggt gctgaagaat aagtttcgga ctaagaggta   4500
cttcgccaag cacccccgca tggggtatct gccagtgcag acagtgctgg aaggagacaa   4560
tatggagacc gatacaatgt gagcggccgc aataaaagat ctttattttc attagatctg   4620
tgtgttggtt ttttgtgtgt ctagagcatg ctacgtaga taagtagcat ggcgggttaa    4680
tcattaacta caaggaaccc ctagtgatgg agttggccac tccctctctg cgcgctcgct   4740
cgctcactga ggccgggcga ccaaaggtcg cccgacgccc gggctttgcc cgggcggcct   4800
cagtgagcga gcgagcgcgc cagctggcgt aatagcgaag aggcccgcac cgatcgccct   4860
tcccaacagt tgcgcagcct gaatggcgaa tggaagttcc agacgattga gcgtcaaaat   4920
gtaggtattt ccatgagcgt ttttcctgtt gcaatggctg cggtaatat tgttctggat     4980 attaccagca aggccgatag tttgagttct tctactcagg caagtgatgt tattactaat   5040
caaagaagta ttgcgacaac ggttaatttg cgtgatggac agactctttt actcggtggc   5100
ctcactgatt ataaaaacac ttctcaggat tctggcgtac cgttcctgtc taaaatccct   5160
ttaatcggcc tcctgtttag ctcccgctct gattctaacg aggaaagcac gttatacgtg   5220
ctcgtcaaag caaccatagt acgcgccctg tagcggcgca ttaagcgcgg cgggtgtggt   5280
ggttacgcgc agcgtgaccg ctacacttgc cagcgcccta gcgcccgctc ctttcgcttt   5340
cttcccttcc tttctcgcca cgttcgccgg ctttccccgt caagctctaa atcgggggct   5400 cccttaggg ttccgattta gtgatttacg gcacctcgac cccaaaaaac ttgattaggg    5460
tgatggttca cgtagtgggc catcgccctg atagacggtt tttcgccctt tgacgttgga   5520
gtccacgttc tttaatagtg gactcttgtt ccaaactgga acaacactca accctatctc   5580
ggtctattct tttgatttat aagggatttt gccgatttcg gcctattggt taaaaaatga   5640
gctgatttaa caaaaattta acgcgaattt taacaaaata ttaacgttta caatttaaat   5700
atttgcttat acaatcttcc tgttttgggg cttttctga ttatcaaccg ggtacatat    5760 gattgacatg ctagttttac gattaccgtt catcgattct cttgtttgct ccagactctc   5820
aggcaatgac ctgatagcct ttgtagagac ctctcaaaaa tagctaccct ctccggcatg   5880
aatttatcag ctagaacggt tgaatatcat attgatggtg atttgactgt ctccggcctt   5940
tctcacccgt ttgaatcttt acctacacat tactcaggca ttgcatttaa aatatatgag   6000
ggttctaaaa attttatcc ttgcgttgaa ataaaggctt ctcccgcaaa agtattacag    6060
ggtcataatg ttttggtac aaccgattta gctttatgct ctgaggcttt attgcttaat   6120
tttgctaatt ctttgccttg cctgtatgat ttattggatg ttggaagttc ctgatgcggt   6180
attttctcct tacgcatctg tgcggtattt cacaccgcat atggtgcact ctcagtacaa   6240
tctgctctga tgccgcatag ttaagccagc cccgacaccc gccaacaccc gctgacgcgc   6300
cctgacgggc ttgtctgctc ccggcatccg cttacagaca agctgtgacc gtctccggga   6360
gctgcatgtg tcagaggttt tcaccgtcat caccgaaacg cgcgagacga aagggcctcg   6420
tgatacgcct atttttatag gttaatgtca tgataataat ggtttcttag acgtcaggtg   6480
gcacttttcg gggaaatgtg cgcggaaccc ctatttgttt attttctaa atacattcaa     6540 atatgtatcc gctcatgaga caataaccct gataaatgct tcaataatat tgaaaaagga   6600
agagtatgag tattcaacat ttccgtgtcg cccttattcc cttttttgcg gcattttgcc   6660
ttcctgtttt tgctcaccca gaaacgctgg tgaaagtaaa agatgctgaa gatcagttgg   6720
gtgcacgagt gggttacatc gaactggatc tcaacagcgg taagatcctt gagagttttc   6780
```

```
gccccgaaga acgttttcca atgatgagca cttttaaagt tctgctatgt ggcgcggtat    6840
tatcccgtat tgacgccggg caagagcaac tcggtcgccg catacactat tctcagaatg    6900
acttggttga gtactcacca gtcacagaaa agcatcttac ggatggcatg acagtaagag    6960
aattatgcag tgctgccata accatgagtg ataacactgc ggccaactta cttctgacaa    7020
cgatcggagg accgaaggag ctaaccgctt ttttgcacaa catgggggat catgtaactc    7080
gccttgatcg ttgggaaccg gagctgaatg aagccatacc aaacgacgag cgtgacacca    7140
cgatgcctgt agcaatggca acaacgttgc gcaaactatt aactggcgaa ctacttactc    7200
tagcttcccg gcaacaatta atagactgga tggaggcgga taaagttgca ggaccacttc    7260
tgcgctcggc ccttccggct ggctggttta ttgctgataa atctggagcc ggtgagcgtg    7320
ggtctcgcgg tatcattgca gcactggggc cagatggtaa gccctcccgt atcgtagtta    7380
tctacacgac ggggagtcag gcaactatgg atgaacgaaa tagacagatc gctgagatag    7440
gtgcctcact gattaagcat tggtaactgt cagaccaagt ttactcatat atactttaga    7500
ttgatttaaa acttcatttt taatttaaaa ggatctaggt gaagatcctt tttgataatc    7560
tcatgaccaa aatcccttaa cgtgagtttt cgttccactg agcgtcagac cccgtagaaa    7620
agatcaaagg atcttcttga tccttttttt tctgcgcgt aatctgctgc ttgcaaacaa    7680
aaaaaccacc gctaccagcg gtggtttgtt tgccggatca agagctacca actctttttc    7740
cgaaggtaac tggcttcagc agagcgcaga taccaaatac tgtccttcta gtgtagccgt    7800
agttaggcca ccacttcaag aactctgtag caccgcgtac atacctcgct ctgctaatcc    7860
tgttaccagt ggctgctgcc agtggcgata agtcgtgtct taccgggttg gactcaagac    7920
gatagttacc ggataaggcg cagcggtcgg gctgaacggg gggttcgtgc acacagccca    7980
gcttggagcg aacgacctac accgaactga gatacctaca gcgtgagcta tgagaaagcg    8040
ccacgcttcc cgaagggaga aaggcggaca ggtatccggt aagcggcagg gtcggaacag    8100
gagagcgcac gagggagctt ccagggggaa acgcctggta tctttatagt cctgtcgggt    8160
ttcgccacct ctgacttgag cgtcgatttt tgtgatgctc gtcaggggg cggagcctat    8220 ggaaaaacgc cagcaacgcg gcctttttac ggttcctggc cttttgctgg ccttttgctc    8280
acatgttctt tcctgcgtta tcccctgatt ctgtggataa ccgtattacc gggtttgagt    8340
gagctgatac cgctcgccgc agccgaacga ccgagcgcag cgagtcagtg agcgaccaag    8400
cggaagagc                                                          8409
```

<210> SEQ ID NO 10
<211> LENGTH: 206
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: enhancer
<222> LOCATION: (1)..(206)
<223> OTHER INFORMATION: MCK enhancer

<400> SEQUENCE: 10

```
cagccactat gggtctaggc tgcccatgta aggaggcaag gcctgggac acccgagatg     60 cctggttata attaacccag acatgtggct gctcccccc cccaacacct gctgcctgag    120
cctcaccccc accccggtgc ctgggtctta ggctctgtac accatggagg agaagctcgc    180
tctaaaaata accctgtccc tggtgg                                        206
```

<210> SEQ ID NO 11
<211> LENGTH: 358
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: promoter
<222> LOCATION: (1)..(358)
<223> OTHER INFORMATION: MCK promoter

<400> SEQUENCE: 11

```
gctgtggggg actgagggca ggctgtaaca ggcttggggg ccagggctta tacgtgcctg      60
ggactcccaa agtattactg ttccatgttc ccggcgaagg gccagctgtc ccccgccagc     120
tagactcagc acttagttta ggaaccagtg agcaagtcag cccttggggc agcccataca     180
aggccatggg gctgggcaag ctgcacgcct gggtccgggg tgggcacggt gcccgggcaa     240
cgagctgaaa gctcatctgc tctcaggggc ccctccctgg gacagcccc  tcctggctag     300 tcacaccctg taggctcctc tatataaccc agggggcacag gggctgcccc cgggtcac      358
```

<210> SEQ ID NO 12
<211> LENGTH: 5920
<212> TYPE: DNA
<213> ORGANISM: Adeno-associated virus
<220> FEATURE:
<221> NAME/KEY: misc_feature
<223> OTHER INFORMATION: pAAV.MCK.miR26C Sequence
<220> FEATURE:
<221> NAME/KEY: misc_feature
<222> LOCATION: (4)..(9)
<223> OTHER INFORMATION: n is a, c, g, t or u
<220> FEATURE:
<221> NAME/KEY: enhancer
<222> LOCATION: (190)..(395)
<223> OTHER INFORMATION: MCK enhancer
<220> FEATURE:
<221> NAME/KEY: promoter
<222> LOCATION: (396)..(753)
<223> OTHER INFORMATION: MCK promoter
<220> FEATURE:
<221> NAME/KEY: misc_feature
<222> LOCATION: (1316)..(1608)
<223> OTHER INFORMATION: shRNA-miR29-c with primary seed sequence
<220> FEATURE:
<221> NAME/KEY: misc_feature
<222> LOCATION: (1487)..(1512)
<223> OTHER INFORMATION: miR-29c
<220> FEATURE:
<221> NAME/KEY: misc_feature
<222> LOCATION: (2094)..(2146)
<223> OTHER INFORMATION: SV40 PolyA
<220> FEATURE:
<221> NAME/KEY: misc_feature
<222> LOCATION: (2326)..(2331)
<223> OTHER INFORMATION: n is a, c, g, t or u

<400> SEQUENCE: 12

```
ctgnnnnnng cgcgctcgct cgctcactga ggccgcccgg gcaaagcccg ggcgtcgggc      60
gacctttggt cgcccggcct cagtgagcga gcgagcgcgc agagagggag tggccaactc     120
catcactagg ggttccttgt agttaatgat taacccgcca tgctaattat ctacgtagcc     180
atgtctagac agccactatg ggtctaggct gcccatgtaa ggaggcaagg cctggggaca     240
cccgagatgc ctggttataa ttaacccaga catgtggctg ctccccccccc ccaacacctg     300 ctgcctgagc ctcaccccca ccccggtgcc tgggtcttag gctctgtaca ccatggagga     360
gaagctcgct ctaaaaataa ccctgtccct ggtgggctgt ggggggactga gggcaggctg     420
```

```
taacaggctt gggggccagg gcttatacgt gcctgggact cccaaagtat tactgttcca    480
tgttcccggc gaagggccag ctgtcccccg ccagctagac tcagcactta gtttaggaac    540
cagtgagcaa gtcagccctt ggggcagccc atacaaggcc atggggctgg gcaagctgca    600
cgcctgggtc cggggtgggc acggtgcccg ggcaacgagc tgaaagctca tctgctctca    660
ggggcccctc cctggggaca gcccctcctg gctagtcaca ccctgtaggc tcctctatat    720
aacccagggg cacaggggct gccccgggt caccaccacc tccacagcac agacagacac     780
tcaggagcca gccagccagg taagtttagt ctttttgtct tttatttcag gtcccggatc    840
cggtggtggt gcaaatcaaa gaactgctcc tcagtggatg ttgcctttac ttctaggcct    900
gtacggaagt gttacttctg ctctaaaagc tgcggaattg tacccgccta gaggatccgg    960
tactcgagga actgaaaaac cagaaagtta actggtaagt ttagtctttt tgtcttttat   1020
ttcaggtccc ggatccggtg gtggtgcaaa tcaaagaact gctcctcagt ggatgttgcc   1080
tttacttcta ggcctgtacg gaagtgttac ttctgctcta aaagctgcgg aattgtaccc   1140
ggggccgatc caccggtctt tttcgcaacg ggtttgccgc cagaacacag gtaagtgccg   1200
tgtgtggttc ccgcgggcgg cgacggggcc cgtgcgtccc agcgcacatg ttcggcgagg   1260
cggggcctgc gagcgcggcc accgagaatc ggacgggggt agtctcaagc tggccggcct   1320
gtttgaatga ggcttcagta ctttacgaaa tcgttgcctg cacatcttgg aaacacttgc   1380
tgggattact tcttcaggtt aacccaacag aaggctcgag aaggtatatt gctgttgaca   1440
gtgagcgcaa ccgatttcaa atggtgctag agtgaagcca cagatgtcta gcaccatttg   1500
aaatcggtta tgcctactgc ctcggaattc aaggggctac tttaggagca attatcttgt   1560
ttactaaaac tgaataccct gctatctctt tgatacattg gccggcctgc tctggtgcct   1620
ggcctcgcgc cgccgtgtat cgccccgccc tgggcggcaa ggctggcccg gtcggcacca   1680
gttgcgtgag cggaaagatg gccgcttccc ggccctgctg cagggagctc aaaatggagg   1740
acgcggcgct cgggagagcg ggcgggtgag tcacccacac aaaggaaaag gcctttccg    1800 tcctcagccg tcgcttcatg tgactccacg gagtaccggg cgccgtccag gcacctcgat   1860
tagttctcga gcttttggag tacgtcgtct ttaggtgggg ggagggtt ttatgcgatg     1920 gagtttcccc acactgagtg ggtggagact gaagttaggc cagcttggca cttgatgtaa   1980
ttctccttgg aatttgccct ttttgagttt ggatcttggt tcattctcaa gcctcagaca   2040
gtggttcaaa gttttttttct tccatttcag gtgtcgtgaa aagctagtgc ggccgcaata   2100
aaagatcttt attttcatta gatctgtgtg ttggttttt gtgtgtctag acatggctac    2160
gtagataatt agcatggcgg gttaatcatt aactacaagg aacccctagt gatggagttg   2220
gccactccct ctctgcgcgc tcgctcgctc actgaggccg ggcgaccaaa ggtcgcccga   2280
cgcccgggct ttgcccgggc ggcctcagtg agcgagcgag cgcgcnnnnn ncagctggcg   2340
taatagcgaa gaggcccgca ccgatcgccc ttcccaacag ttgcgcagcc tgaatggcga   2400
atggaagttc cagacgattg agcgtcaaaa tgtaggtatt tccatgagcg ttttttcctgt  2460 tgcaatggct ggcggtaata ttgttctgga tattaccagc aaggccgata gtttgagttc   2520
ttctactcag gcaagtgatg ttattactaa tcaaagaagt attgcgacaa cggttaattt   2580
gcgtgatgga cagactcttt tactcggtgg cctcactgat tataaaaaca cttctcagga   2640
ttctggcgta ccgttcctgt ctaaaatccc tttaatcggc ctcctgttta gctcccgctc   2700
tgattctaac gaggaaagca cgttatacgt gctcgtcaaa gcaaccatag tacgcgccct   2760
gtagcggcgc attaagcgcg gcgggtgtgg tggttacgcg cagcgtgacc gctacacttg   2820
```

```
ccagcgccct agcgcccgct cctttcgctt tcttcccttc ctttctcgcc acgttcgccg      2880
gctttccccg tcaagctcta aatcgggggc tcccttttagg gttccgattt agtgatttac     2940
ggcacctcga ccccaaaaaa cttgattagg gtgatggttc acgtagtggg ccatcgccct      3000
gatagacggt ttttcgccct ttgacgttgg agtccacgtt ctttaatagt ggactcttgt      3060
tccaaactgg aacaacactc aaccctatct cggtctattc ttttgattta taagggattt      3120
tgccgatttc ggcctattgg ttaaaaaatg agctgattta caaaaattt aacgcgaatt       3180 ttaacaaaat attaacgttt acaatttaaa tatttgctta tacaatcttc ctgttttttgg    3240 ggcttttctg attatcaacc ggggtacata tgattgacat gctagtttta cgattaccgt     3300
tcatcgattc tcttgtttgc tccagactct caggcaatga cctgatagcc tttgtagaga     3360
cctctcaaaa atagctaccc tctccggcat gaatttatca gctagaacgg ttgaatatca     3420
tattgatggt gatttgactg tctccggcct ttctcacccg tttgaatctt tacctacaca     3480
ttactcaggc attgcattta aaatatatga gggttctaaa aattttttatc cttgcgttga    3540 aataaaggct tctcccgcaa aagtattaca gggtcataat gtttttggta caaccgattt     3600
agctttatgc tctgaggctt tattgcttaa ttttgctaat tctttgcctt gcctgtatga     3660
tttattggat gttggaagtt cctgatgcgg tattttctcc ttacgcatct gtgcggtatt     3720
tcacaccgca tatggtgcac tctcagtaca atctgctctg atgccgcata gttaagccag     3780
ccccgacacc cgccaacacc cgctgacgcg ccctgacggg cttgtctgct cccggcatcc     3840
gcttacagac aagctgtgac cgtctccggg agctgcatgt gtcagaggtt ttcaccgtca     3900
tcaccgaaac gcgcgagacg aaagggcctc gtgatacgcc tatttttata ggttaatgtc     3960
atgataataa tggtttctta gacgtcaggt ggcactttc gggggaaatgt gcgcggaacc     4020 cctatttgtt tatttttcta aatacattca aatatgtatc cgctcatgag acaataaccc     4080
tgataaatgc ttcaataata ttgaaaaagg aagagtatga gtattcaaca tttccgtgtc     4140
gcccttattc ccttttttgc ggcatttttgc cttcctgttt ttgctcaccc agaaacgctg    4200
gtgaaagtaa aagatgctga agatcagttg ggtgcacgag tgggttacat cgaactggat     4260
ctcaacagcg gtaagatcct tgagagtttt cgccccgaag aacgttttcc aatgatgagc     4320
acttttaaag ttctgctatg tggcgcggta ttatcccgta ttgacgccgg gcaagagcaa     4380
ctcggtcgcc gcatacacta ttctcagaat gacttggttg agtactcacc agtcacagaa     4440
aagcatctta cggatggcat gacagtaaga gaattatgca gtgctgccat aaccatgagt     4500
gataacactg cggccaactt acttctgaca acgatcggag gaccgaagga ctaaccgct     4560 tttttgcaca acatgggga tcatgtaact cgccttgatc gttgggaacc ggagctgaat     4620
gaagccatac caaacgacga gcgtgacacc acgatgcctg tagcaatggc aacaacgttg    4680
cgcaaactat taactggcga actacttact ctagcttccc ggcaacaatt aatagactgg    4740
atggaggcgg ataaagttgc aggaccactt ctgcgctcgg cccttccggc tggctggttt    4800
attgctgata atctggagc cggtgagcgt gggtctcgcg gtatcattgc agcactgggg     4860
ccagatggta agccctcccg tatcgtagtt atctacacga cggggagtca ggcaactatg    4920
gatgaacgaa atagacagat cgctgagata ggtgcctcac tgattaagca ttggtaactg    4980
tcagaccaag tttactcata tatactttag attgatttaa aacttcattt ttaatttaaa    5040
aggatctagg tgaagatcct ttttgataat ctcatgacca aaatccctta acgtgagttt    5100
tcgttccact gagcgtcaga cccgtagaa aagatcaaag gatcttcttg agatcctttt      5160
```

```
tttctgcgcg taatctgctg cttgcaaaca aaaaaaccac cgctaccagc ggtggtttgt    5220
ttgccggatc aagagctacc aactcttttt ccgaaggtaa ctggcttcag cagagcgcag    5280
ataccaaata ctgtccttct agtgtagccg tagttaggcc accacttcaa gaactctgta    5340
gcaccgcgta catacctcgc tctgctaatc ctgttaccag tggctgctgc cagtggcgat    5400
aagtcgtgtc ttaccgggtt ggactcaaga cgatagttac cggataaggc gcagcggtcg    5460
ggctgaacgg ggggttcgtg cacacagccc agcttggagc gaacgaccta cacgaactg    5520 agatacctac agcgtgagct atgagaaagc gccacgcttc ccgaagggag aaaggcggac    5580
aggtatccgg taagcggcag ggtcggaaca ggagagcgca cgagggagct tccaggggga    5640
aacgcctggt atctttatag tcctgtcggg tttcgccacc tctgacttga gcgtcgattt    5700
ttgtgatgct cgtcagggg gcggagccta tggaaaaacg ccagcaacgc ggccttttta    5760
cggttcctgg ccttttgctg gccttttgct cacatgttct ttcctgcgtt atcccctgat    5820
tctgtggata accgtattac cgggtttgag tgagctgata ccgctcgccg cagccgaacg    5880
accgagcgca gcgagtcagt gagcgaccaa gcggaagagc                         5920
```

<210> SEQ ID NO 13
<211> LENGTH: 810
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: MHCK7 sequence

<400> SEQUENCE: 13

```
gtttaaacaa gcttgcatgt ctaagctaga cccttcagat taaaaataac tgaggtaagg      60
gcctgggtag gggaggtggt gtgagacgct cctgtctctc ctctatctgc ccatcggccc     120
tttggggagg aggaatgtgc ccaaggacta aaaaaaggcc atggagccag aggggcgagg     180
gcaacagacc tttcatgggc aaaccttggg gccctgctgt ctagcatgcc ccactacggg     240
tctaggctgc ccatgtaagg aggcaaggcc tggggacacc cgagatgcct ggttataatt     300
aacccagaca tgtggctgcc cccccccccc caacacctgc tgcctctaaa aataaccctg     360
tccctggtgg atcccctgca tgcgaagatc ttcgaacaag gctgtggggg actgagggca     420
ggctgtaaca ggcttggggg ccagggctta tacgtgcctg ggactccaa agtattactg     480 ttccatgttc ccggcgaagg gccagctgtc ccccgccagc tagactcagc acttagttta     540
ggaaccagtg agcaagtcag cccttggggc agcccataca aggccatggg gctgggcaag    600
ctgcacgcct gggtccgggg tgggcacggt gcccgggcaa cgagctgaaa gctcatctgc    660
tctcaggggc ccctccctgg ggacagcccc tcctggctag tcacaccctg taggctcctc    720
tatataaccc aggggcacag gggctgccct cattctacca ccacctccac agcacagaca    780
gacactcagg agccagccag cggcgcgccc                                      810
```

ADENO-ASSOCIATED VIRUS VECTOR DELIVERY OF MICRORNA-29 AND MICRO-DYSTROPHIN TO TREAT MUSCULAR DYSTROPHY

This application is a National Stage Application of International Patent Application No. PCT/US2017/027635, filed Apr. 14, 2017, which claims priority benefit of U.S. Provisional Application No. 62/323,163, filed Apr. 15, 2016 and U.S. Provisional Application No. 62/473,253, filed Mar. 17, 2017, both of which are incorporated by reference herein in their entirety.

FIELD OF INVENTION

The invention provides gene therapy vectors, such as adeno-associated virus (AAV) vectors, expressing the microRNA miR-29 and method of using these vectors to reduce and prevent fibrosis in subjects suffering from dystrophinopathy or muscular dystrophy. The invention also provides for combination gene therapy methods expressing both miR-29 and a miniaturized human micro-dystrophin gene to reduce and prevent fibrosis in patients suffering from dystrophinopathy or muscular dystrophy and to protect muscle fibers from injury, increase muscle strength.

BACKGROUND

The importance of muscle mass and strength for daily activities, such as locomotion and breathing, and for whole body metabolism is unequivocal. Deficits in muscle function produce muscular dystrophies (MDs) that are characterized by muscle weakness and wasting and have serious impacts on quality of life. The most well-characterized MDs result from mutations in genes encoding members of the dystrophin-associated protein complex (DAPC). These MDs result from membrane fragility associated with the loss of sarcolemmal-cytoskeleton tethering by the DAPC. Duchenne Muscular Dystrophy (DMD) is one of the most devastating muscle diseases affecting 1 in 5000 newborn males.

This application includes two translational approaches to develop treatment for DMD. Fibrotic infiltration is profound in DMD and is a significant impediment to any potential therapy. It is also important to consider that gene replacement alone is hampered by the severity of fibrosis, already present in very young children with DMD. In fact, muscle biopsies at the usual age of diagnosis, between 4-5 years old, show very significant levels of fibrosis.

DMD is caused by mutations in the DMD gene leading to reductions in mRNA and the absence of dystrophin, a 427 kD sarcolemmal protein associated with the dystrophin-associated protein complex (DAPC) (Hoffman et al., Cell 51(6):919-28, 1987). The DAPC is composed of multiple proteins at the muscle sarcolemma that form a structural link between the extra-cellular matrix (ECM) and the cytoskeleton via dystrophin, an actin binding protein, and alpha-dystroglycan, a laminin-binding protein. These structural links act to stabilize the muscle cell membrane during contraction and protect against contraction-induced damage. With dystrophin loss, membrane fragility results in sarcolemmal tears and an influx of calcium, triggering calcium-activated proteases and segmental fiber necrosis (Straub et al., Curr Opin. Neurol. 10(2): 168-75, 1997). This uncontrolled cycle of muscle degeneration and regeneration ultimately exhausts the muscle stem cell population (Sacco et al., Cell, 2010. 143(7): p. 1059-71; Wallace et al., Annu Rev Physiol, 2009. 71: p. 37-57), resulting in progressive muscle weakness, endomysial inflammation, and fibrotic scarring.

Without membrane stabilization from dystrophin or a micro-dystrophin, DMD will manifest uncontrolled cycles of tissue injury and repair and ultimately replace lost muscle fibers with fibrotic scar tissue through connective tissue proliferation. Fibrosis is characterized by the excessive deposits of ECM matrix proteins, including collagen and elastin. ECM proteins are primarily produced from cytokines such as TGFβ that is released by activated fibroblasts responding to stress and inflammation. Although the primary pathological feature of DMD is myofiber degeneration and necrosis, fibrosis as a pathological consequence has equal repercussions. The over-production of fibrotic tissue restricts muscle regeneration and contributes to progressive muscle weakness in the DMD patient. In one study, the presence of fibrosis on initial DMD muscle biopsies was highly correlated with poor motor outcome at a 10-year follow-up (Desguerre et al., J Neuropathol Exp Neurol, 2009. 68(7): p. 762-7). These results point to fibrosis as a major contributor to DMD muscle dysfunction and highlight the need to develop therapies that reduce fibrotic tissue. Most anti-fibrotic therapies that have been tested in mdx mice act to block fibrotic cytokine signaling through inhibition of the TGFβ pathway. MicroRNAs (miRNAs) are single-stranded RNAs of 22 nucleotides that mediate gene silencing at the post-transcriptional level by pairing with bases within the 3' UTR of mRNA, inhibiting translation or promoting mRNA degradation. A seed sequence of 7 bp at the 5' end of the miRNA targets the miRNA; additional recognition is provided by the remainder of the targeted sequence, as well as its secondary structure. MiRNAs play an important role in muscle disease pathology and exhibit expression profiles that are uniquely dependent on the type of muscular dystrophy in question (Eisenberg et al. Proc Natl Acad Sci USA, 2007. 104(43): p. 17016-21). A growing body of evidence suggests that miRNAs are involved in the fibrotic process in many organs including heart, liver, kidney, and lung (Jiang et al., Proc Natl Acad Sci USA, 2007. 104(43): p. 17016-21). Recently, the down-regulation of miR-29 was shown to contribute to cardiac fibrosis (Cacchiarelli et al., Cell Metab, 2010. 12(4): p. 341-51) and reduced expression of miR-29 was genetically linked with human DMD patient muscles (Eisenberg et al. Proc Natl Acad Sci USA, 2007. 104(43): p. 17016-2). The miR-29 family consists of three family members expressed from two bicistronic miRNA clusters. MiR-29a is coexpressed with miR-29b (miR-29b-1); miR-29c is coexpressed with a second copy of miR-29b (miR-29b-2). The miR-29 family shares a conserved seed sequence and miR-29a and miR-29b each differ by only one base from miR-29c. Furthermore, electroporation of miR-29 plasmid (a cluster of miR-29a and miR-29b-1) into mdx mouse muscle reduced the expression levels of ECM components, collagen and elastin, and strongly decreased collagen deposition in muscle sections within 25 days post-treatment (Cacchiarelli et al., Cell Metab, 2010. 12(4): p. 341-51).

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the nucleotide sequence of the AAV serotype 2 (AAV2) genome is presented in Srivastava et al., J Virol, 45: 555-564 (1983) as corrected by Ruffing et al., J Gen Virol, 75: 3385-3392 (1994). As other examples, the complete genome of AAV-1 is provided in GenBank Accession No. NC_002077; the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_001862; at least portions of AAV-7 and AAV-8 genomes are provided in GenBank Accession Nos. AX753246 and AX753249, respectively (see also U.S. Pat. Nos. 7,282,199 and 7,790,449 relating to AAV-8); the AAV-9 genome is provided in Gao et al., *J. Virol.*, 78: 6381-6388 (2004); the AAV-10 genome is provided in *Mol. Ther.*, 13(1): 67-76 (2006); and the AAV-11 genome is provided in *Virology*, 330(2): 375-383 (2004). The AAVrh74 serotype is described in Rodino-Klapac et al. *J. Trans. Med.* 5: 45 (2007). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (e.g., at AAV2 nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., *Hum Gene Ther*, 8: 659-669 (1997); Kessler et al., *Proc Nat. Acad Sc. USA*, 93: 14082-14087 (1996); and Xiao et al., *J Virol*, 70: 8098-8108 (1996). See also, Chao et al., *Mol Ther*, 2:619-623 (2000) and Chao et al., *Mol Ther*, 4:217-222 (2001). Moreover, because muscle is highly vascularized, recombinant AAV transduction has resulted in the appearance of transgene products in the systemic circulation following intramuscular injection as described in Herzog et al., *Proc Natl Acad Sci USA*, 94: 5804-5809 (1997) and Murphy et al., *Proc Natl Acad Sci USA*, 94: 13921-13926 (1997). Moreover, Lewis et al., *J Virol*, 76: 8769-8775 (2002) demonstrated that skeletal myofibers possess the necessary cellular factors for correct antibody glycosylation, folding, and secretion, indicating that muscle is capable of stable expression of secreted protein therapeutics.

Functional improvement in patients suffering from DMD and other muscular dystrophies require both gene restoration and reduction of fibrosis. There is a need for methods of reducing fibrosis that may be paired with gene restoration methods for more effective treatments of DMD and other muscular dystrophies. miR29 is a potential gene regulator and an ideal candidate for reducing muscle fibrosis.

SUMMARY OF INVENTION

The present invention is directed to gene therapy methods that directly reduce the three primary components of connective tissue (collagen 1, collagen 3 and fibronectin) by delivering the microRNA miR29. In this system, the miR29 binds to the 3' UTR of the collagen and fibronectin gene to down regulate expression. The invention is directed to gene therapy vectors, e.g. AAV, expressing the guide strand of the microRNA miR29 and method of delivering miR29 to the muscle to reduce and/or prevent fibrosis.

In addition, the invention provides for combination therapies and approaches for reducing and preventing fibrosis using gene therapy vectors deliver miR-29 to suppress fibrosis along with micro-dystrophin to address the gene defect observed in DMD. As shown in Examples 5-7, the combination treatment resulted in a greater reduction in fibrosis, increased muscle size and increased muscle force.

In one embodiment, the invention provides for a rAAV vector expressing miR-29. For example, the rAAV vector comprises a polynucleotide sequence expressing miR29c such as a nucleotide sequence comprising the miR-29c target guide strand of SEQ ID NO: 3, the miR-29c guide strand of SEQ ID NO: 4 and the natural miR-30 back bone and stem loop (SEQ ID NO: 5). An exemplary polynucleotide sequence comprising the miR-29c cDNA in a miR-30 backbone is set out as SEQ ID NO: 2 (FIG. 1).

An exemplary rAAV of the invention is the pAAV.CMV.Mir29C which comprises the nucleotide sequence of SEQ ID NO: 1; wherein the CMV promoter spans nucleotides 120-526, an EF1a intron spans nucleotides 927-1087 and nucleotides 1380-1854, the guide stand of miR-29c spans nucleotide 1257-1284 and the shRNA-miR29-c with primary seed sequence spans nucleotides 1088-1375, and the poly A sequence spans nucleotides 1896-2091. In one aspect, the rAAV vectors of the invention are AAV1, AAV2, AAV4, AAV5, AAV6, AAV7, AAVrh.74, AAV8, AAV9, AAV10, AAV11, AAV12 or AAV13.

Another exemplary rAAV of the invention is the pAAV.MHC.Mir29C which comprises the nucleotide sequence of SEQ ID NO: 12; wherein the MCK enhancer spans nucleotides 190-395, the MHC promoter spans nucleotides 396-753, an EF1a intron spans nucleotides 1155-1315 and nucleotides 1609-2083, the guide stand of miR-29c spans nucleotide 1487-1512 and the shRNA-miR29-c with primary seed sequence spans nucleotides 1316-1608, and the poly A sequence spans nucleotides 2094-2146. In one aspect, the rAAV vectors of the invention are AAV1, AAV2, AAV4, AAV5, AAV6, AAV7, AAVrh.74, AAV8, AAV9, AAV10, AAV11, AAV12 or AAV13.

In another aspect, the rAAV vectors expressing miR29 of the invention may be operably linked to a muscle-specific control element or an ubiquitous promoter, such as the cytomegalovirus (CMV) promoter. For example the muscle-specific control element is human skeletal actin gene element, cardiac actin gene element, myocyte-specific enhancer binding factor MEF, muscle creatine kinase (MCK), tMCK (truncated MCK), myosin heavy chain (MHC), MHCK7 (a hybrid version of MHC and MCK), C5-12 (synthetic promoter), murine creatine kinase enhancer element, skeletal fast-twitch troponin C gene element, slow-twitch cardiac troponin C gene element, the slow-twitch troponin I gene element, hypozia-inducible nuclear factors, steroid-inducible element or glucocorticoid response element (GRE).

For example, any of the rAAV vectors expressing miR-29 of the invention are operably linked to the muscle-specific control element comprising the MCK enhancer nucleotide sequence of SEQ ID NO: 10 and/or the MCK promoter sequence of SEQ ID NO: 11. In addition, any of the rAAV vectors of the invention are operably linked to the muscle specific control element comprising the MHCK7 enhancer nucleotide sequence of SEQ ID NO: 13.

The invention also provides for pharmaceutical compositions (or sometimes referred to herein as simply "compositions") comprising any of the rAAV vectors of the invention.

In another embodiment, the invention provides for methods of producing a rAAV vector particle comprising culturing a cell that has been transfected with any rAAV vector of the invention and recovering rAAV particles from the supernatant of the transfected cells. The invention also provides for viral particles comprising any of the recombinant AAV vectors of the invention.

In another embodiment, the invention provides for methods of reducing fibrosis in a subject in need comprising administering a therapeutically effective amount of any rAAV vector of the invention expressing miR-29. For example, any of the rAAV of the invention are administered to subjects suffering from dystrophinopathy or muscular dystrophy, such as DMD or Becker muscular dystrophy, to reduce fibrosis, and in particular reduces fibrosis in skeletal muscle or in cardiac muscle of the subject. These methods may further comprise the step of administering a rAAV expressing micro-dystrophin.

"Fibrosis" refers to the excessive or unregulated deposition of extracellular matrix (ECM) components and abnormal repair processes in tissues upon injury including skeletal muscle, cardiac muscle, liver, lung, kidney, and pancreas. The ECM components that are deposited include fibronectin and collagen, e.g. collagen 1, collagen 2 or collagen 3.

In another embodiment, the invention provides for methods of preventing fibrosis in a subject in need comprising administering a therapeutically effective amount of the any recombinant AAV vector of the invention expressing miR-29. For example, any of the rAAV of the invention are administered to subjects suffering from dystrophinopathy or muscular dystrophy, such as DMD or Becker muscular dystrophy, to prevent fibrosis, e.g. the rAAV of the invention expressing miR-29 are administered before fibrosis is observed in the subject. In addition, the rAAV of the invention expressing miR-29 are administered to a subject at risk of developing fibrosis, such as those suffering or diagnosed with dystrophinopathy or muscular dystrophy, e.g. DMD or Becker muscular dystrophy. The rAAV of the invention are administered to the subject suffering from dystrophinopathy or muscular dystrophy, such as DMD or Becker muscular dystrophy, in order to prevent new fibrosis in these subjects. These methods may further comprise the step of administering a rAAV expressing micro-dystrophin.

The invention also provides for methods of increasing muscular force and/or muscle mass in a subject suffering from dystrophinopathy or muscular dystrophy, such as DMD or Becker muscular dystrophy, comprising administering a therapeutically effective amount of any of the rAAV vector of the invention expressing miR-29. These methods may further comprise the step of administering a rAAV expressing micro-dystrophin.

The terms "combination therapy" and "combination treatment" refer to administration of a rAAV vector of the invention expressing miR-29 and an rAAV vector expressing micro-dystrophin.

In any of the methods of the invention, the subject may be suffering from dystrophinopathy or muscular dystrophy such as DMD, Becker muscular dystrophy or any other dystrophin-associated muscular dystrophy.

Any of the foregoing methods of the invention may comprise a further step of administering a rAAV expressing micro-dystrophin. The micro-dystrophin protein comprises the amino acid sequence of SEQ ID NO: 8. The methods may comprises the step of administering a rAAV comprising the coding sequence for the micro-dystrophin gene (SEQ ID NO: 7) or comprising a nucleotide sequence that is at least 85% identical to the nucleotide sequence of SEQ ID NO: 7.

An exemplary rAAV expressing micro-dystrophin of the invention is the pAAV.mck.micro-dystrophin which comprises the nucleotide sequence of SEQ ID NO: 9 and shown in FIGS. 10 and 11. This rAAV vector comprises the MCK promoter, a chimeric intron sequence, the coding sequence for the micro-dystrophin gene, polyA, ampicillin resistance and the pGEX plasmid backbone with pBR322 origin or replication. In one aspect, the recombinant AAV vectors of the invention are AAV1, AAV2, AAV4, AAV5, AAV6, AAV7, AAVrh74, AAV8, AAV9, AAV10, AAV11, AAV12 or AAV13.

The methods of the invention are carried out with rAAV vectors encoding the micro-dystrophin protein that is, e.g., at least at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to SEQ ID NO: 8, wherein the protein retains micro-dystrophin activity. The micro-dystrophin protein provides stability to the muscle membrane during muscle contraction, e.g. micro-dystrophin acts as a shock absorber during muscle contraction.

The methods of the invention are carried out with rAAV vectors expressing the micro-dystrophin comprising a nucleotide sequence that has at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to SEQ ID NO: 7, and encodes a functional micro-dystrophin protein.

The methods of the invention are carried out with rAAV vectors expressing micro-dystrophin comprising a nucleotide sequence that hybridizes under stringent conditions to the nucleic acid sequence of SEQ ID NOS: 7, or compliments thereof, and encodes a functional micro-dystrophin protein.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., Molecular Cloning: A Laboratory Manual, 2nd Ed., Cold Spring Harbor Laboratory, (Cold Spring Harbor, N.Y. 1989). More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO4, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., *Nucleic Acid Hybridisation: A Practical Approach*, Ch. 4, IRL Press Limited (Oxford, England). Hybridization conditions can be adjusted by one skilled in the art in order to accommodate these variables and allow DNAs of different sequence relatedness to form hybrids.

In another aspect, the rAAV vectors expressing micro-dystrophin comprises the coding sequence of the micro-dystrophin gene operably linked to a muscle-specific control element. For example, the muscle-specific control element is human skeletal actin gene element, cardiac actin gene element, myocyte-specific enhancer binding factor MEF, muscle creatine kinase (MCK), tMCK (truncated MCK), myosin heavy chain (MHC), C5-12 (synthetic promoter), murine creatine kinase enhancer element, skeletal fast-twitch troponin C gene element, slow-twitch cardiac troponin C gene element, the slow-twitch troponin I gene element, hypozia-inducible nuclear factors, steroid-inducible element or glucocorticoid response element (GRE).

In the methods of administering an rAAV vector expressing miR-29 and an rAAV vector expressing micro-dystrophin, these rAAV vectors may be administered concurrently, or administered consecutively with the rAAV vector expressing miR29 administered immediately before the rAAV expressing micro-dystrophin, or administered consecutively with the rAAV vector expressing miR29 is administered immediately after the rAAV expressing micro-dystrophin. Alternatively, the methods of the invention are carried out wherein the AAV vector expressing micro-dystrophin is administered within about 1-5 hours or 5-12 hours or 12 to 15 hours or 15 to 24 hours after administering the rAAV expressing miR-29 or the methods of the invention are carried out wherein the AAV vector expressing micro-dystrophin is administered within about 1-5 hours or 5-12 hours or 12 to 15 hours or 15 to 24 hours before administering the rAAV expressing miR-29. Alternatively, the methods of the invention are carried out wherein the AAV vector expressing micro-dystrophin is administered within about 1 or 6 or 12 or 24 hours after administering the rAAV expressing miR-29 or the methods of the invention are carried out wherein the AAV vector expressing micro-dystrophin is administered within about 1 or 6 or 12 or 24 hours before administering the rAAV expressing miR-29.

The invention contemplates administering any of the AAV vectors of the invention to patients diagnosed with dystrophinopathy or muscular dystrophy, such as DMD or Becker muscular dystrophy before fibrosis is observed in the subject or before the muscle force has been reduced in the subject or before the muscle mass has been reduced in the subject.

The invention also contemplates administering any of the rAAV of the invention to a subject suffering from dystrophinopathy or muscular dystrophy, such as DMD or Becker muscular dystrophy, who already has developed fibrosis, in order to prevent new fibrosis in these subjects. The invention also provides for administering any of the rAAV of the invention to the patient suffering from dystrophinopathy or muscular dystrophy, such as DMD or Becker muscular dystrophy, who already has reduced muscle force or has reduced muscle mass in order to protect the muscle from further injury.

In any of the methods of the invention, the rAAV vector are administered by intramuscular injection or intravenous injection.

In addition, in any of the methods of the invention, the rAAV vector or composition is administered systemically. For examples, the rAAV vector or composition is parentally administration by injection, infusion or implantation.

In another embodiment, the invention provides for composition comprising any of the rAAV vectors expressing miR29 for reducing fibrosis in a subject in need. In some embodiments, this composition also comprises a rAAV vector expressing micro-dystrophin. For example, this composition comprises a rAAV comprising the coding sequence for the micro-dystrophin gene (SEQ ID NO: 7) or comprises a nucleotide sequence that is at least 85% identical to the nucleotide sequence of SEQ ID NO: 7.

In addition, the invention provides for compositions comprising any of the recombinant AAV vectors expressing miR29 for preventing fibrosis in a patient suffering from dystrophinopathy or muscular dystrophy, such as DMD or Becker muscular dystrophy. In some embodiments, this composition also comprises a rAAV vector expressing micro-dystrophin. For example, this composition comprises a rAAV comprising the coding sequence for the micro-dystrophin gene (SEQ ID NO: 7) or may comprising a nucleotide sequence that is at least 85% identical to the nucleotide sequence of SEQ ID NO: 7.

The invention also provides for compositions comprising any of the rAAV vectors of the invention expressing miR29 for increasing muscular force and/or muscle mass in a subject suffering from dystrophinopathy or muscular dystrophy, such as DMD or Becker muscular dystrophy. In some embodiments, this composition also comprises a rAAV vector expressing micro-dystrophin. For example, this composition comprises a rAAV vector comprising the coding sequence for the micro-dystrophin gene (SEQ ID NO: 7) or comprises a nucleotide sequence that is at least 85% identical to the nucleotide sequence of SEQ ID NO: 7.

In a further embodiment, the invention provides for compositions comprising any of the rAAV vectors of the invention expressing miR29 for treatment of dystrophinopathy or muscular dystrophy, such as DMD or Becker muscular dystrophy. In some embodiments, this composition also comprises a rAAV vector expressing micro-dystrophin. For example, this composition comprises a rAAV vector comprising the coding sequence for the micro-dystrophin gene (SEQ ID NO: 7) or comprises a nucleotide sequence that is at least 85% identical to the nucleotide sequence of SEQ ID NO: 7.

The compositions of the invention are formulated for intramuscular injection or intravenous injection. The composition of the invention is also formulated for systemic administration, such as parentally administration by injection, infusion or implantation. In addition, any of the compositions are formulated for administration to a subject suffering from dystrophinopathy or muscular dystrophy such as DMD, Becker muscular dystrophy or any other dystrophin associated muscular dystrophy.

In a further embodiment, the invention provides for use of any of the rAAV vectors of the invention expressing miR29 for preparation of a medicament for reducing fibrosis in a subject in need. For example, the subject is in need suffering from dystrophinopathy or muscular dystrophy, such as DMD, Becker muscular dystrophy or any other dystrophin associated muscular dystrophy. In some embodiments, the medicament further comprises a rAAV vector expressing micro-dystrophin. For example, this medicament comprises a rAAV comprising the coding sequence for the micro-dystrophin gene (SEQ ID NO: 7) or comprises a nucleotide sequence that is at least 85% identical to the nucleotide sequence of SEQ ID NO: 7.

In another embodiment, the invention provides for provides for use of any of the rAAV vectors of the invention expressing miR29 for the preparation of a medicament for preventing fibrosis in a subject suffering from dystrophinopathy or muscular dystrophy, such as DMD or Becker muscular dystrophy. In some embodiments, the medicament further comprises a rAAV vector expressing micro-dystrophin. For example, this medicament comprises a rAAV vector comprising the coding sequence for the micro-dystrophin gene (SEQ ID NO: 7) or comprising a nucleotide sequence that is at least 85% identical to the nucleotide sequence of SEQ ID NO: 7.

In addition, the invention provides for use of the recombinant AAV vectors of the invention expressing miR29 for the preparation of a medicament for the increasing muscular strength and/or muscle mass in a subject suffering from dystrophinopathy or muscular dystrophy, such as DMD or Becker muscular dystrophy. In some embodiments, the medicament further comprises a rAAV vector expressing micro-dystrophin. For example, this medicament comprises a rAAV comprising the coding sequence for the micro-dystrophin gene (SEQ ID NO: 7) or comprises a nucleotide sequence that is at least 85% identical to the nucleotide sequence of SEQ ID NO: 7.

The invention contemplates use of the any of the AAV vectors of the invention for the preparation of a medicament for administration to a patient diagnosed with dystrophinopathy or muscular dystrophy, such as DMD or Becker muscular dystrophy, before fibrosis is observed in the subject or before the muscle force has been reduced in the subject or before the muscle mass has been reduced in the subject.

The invention also contemplates use of any of the AAV vectors of the invention for the preparation of a medicament for administration to administering any of the rAAV of the invention to a subject suffering from dystrophinopathy or muscular dystrophy, such as DMD or Becker muscular dystrophy, who already has developed fibrosis, in order to prevent new fibrosis in these subjects. The invention also provides for administering any of the rAAV of the invention to the patient suffering from dystrophinopathy or muscular dystrophy, such as DMD or Becker muscular dystrophy who already has reduced muscle force or has reduced muscle mass in order to protect the muscle from further injury.

The invention also provides for use of the rAAV vectors of the invention expressing miR296 for the preparation of a medicament for treatment of dystrophinopathy or muscular dystrophy, such as DMD or Becker muscular dystrophy. In some embodiments, the medicament further comprises a rAAV vector expressing micro-dystrophin. For example, this medicament comprises a rAAV comprising the coding sequence for the micro-dystrophin gene (SEQ ID NO: 7) or comprises a nucleotide sequence that is at least 85% identical to the nucleotide sequence of SEQ ID NO: 7.

In any of the uses of the invention, the medicament is formulated for intramuscular injection. In addition, any of the medicaments may be prepared for administration to a subject suffering from muscular dystrophy such as DMD or any other dystrophin associated muscular dystrophy.

In addition, any of the medicaments of the invention may be a combination therapy in which the rAAV vectors expressing miR-29 and rAAV vectors expressing micro-dystrophin are administered concurrently, or administered consecutively with the rAAV vector expressing miR29 administered immediately before the rAAV expressing micro-dystrophin, or administered consecutively with the rAAV vector expressing miR29 administered immediately after the rAAV expressing micro-dystrophin. Alternatively, the medicament comprises administration of the AAV vector expressing micro-dystrophin administered within about 1-5 hours after administering the rAAV expressing miR-29 or the medicament comprises the AAV vector expressing micro-dystrophin administered within about 1-5 hours before administering the rAAV expressing miR-29.

BRIEF DESCRIPTION OF DRAWING

FIG. 1 provide a schematic of rAAV vector scAAVCrh.74.CMV.miR29c and the nucleotide sequence of the miR-29c in a natural miR-30 backbone and the nucleotide sequence of the predicted hairpin structure.

FIG. 5A-5C demonstrates that co-delivery of miR-29c with micro-dystrophin reduces collagen expression (panel A) and fibrosis-induced dystrophin expression.

Sections of treated and untreated mdx/utrn$^{+/-}$ gastrocnemius muscles stained with picrosirius Red to stain for collagen are shown. Fibrotic areas are pink and intact muscle is in green. On the macroscopic level, miR-29c/µ-dys combination decreases fibrosis and increases total cross sectional area.

FIG. 9A-F demonstrates that treatment with miR-29c co-delivered with micro-dystrophin increased muscle hypertrophy and hyperplasia as shown by an increase in the overall weight of the injected gastroc compared to either one injected alone (panel A), an increase in the an increase in average fiber size (panel B), an increase in cross-sectional area of the muscle (panel D; uninjected: 24.6 vs. miR-29c: 26.3 vs. micro-dys: 26.6 vs. micro-dys/miR-29c: 33.1) and an increase in the number of muscle fibers (panel E) but the number of muscle fibers per unit area was not affected (panel F). Panel C compares mdx/utrn$^{+/-}$ controls with miR-29c/µ-dys treated mdx/utrn$^{+/-}$, the average diameter increased from 25.96 to 30.97 µm FIG. 10A-G demonstrates that early treatment of AAV.miR-29c/micro-dystrophin combination therapy is more effective at reducing fibrosis and ECM expression. Panel A shows picrosirius red staining of wild-type, uninjected, AAV.miR-29c, AAV.micro-dystrophin, and AAV.miR-29c/AAV.micro-dystrophin of mice injected at 4-5 wks of age taken out twelve weeks post-injection. Panel B provides quantification of picrosirius red staining showing co-treated muscle had a 51.1% reduction in collagen compared to uninjected GAS muscle. Panel C demonstrates that qRT-PCR confirms an increase in miR-29c transcript levels in the treated cohorts. Semi-quantitative qRT-PCR shows a significant reduction in collagen I and III (panels d, e), fbn (panel f) and TGF-β1 (panel g) levels in the AAV.miR-29c/AAV.micro-dystrophin treated muscle compared to the contralateral limb and each of the single therapies Error bars, SEM for n=5 (scAAVrh.74.CMV.miR-29c), n=5 (scAAVrh.74.CMV.miR-29c/ssAAVrh.74.MCK.micro-dystrophin), n=6 (ssAAVrh.74.MCK.micro-dystrophin), n=9 (mdx/utrn$^{+/-}$ mice). 1-way ANOVA ($*p<0.05$, $p<0.01$, $*p<0.001$)

Figure 11:
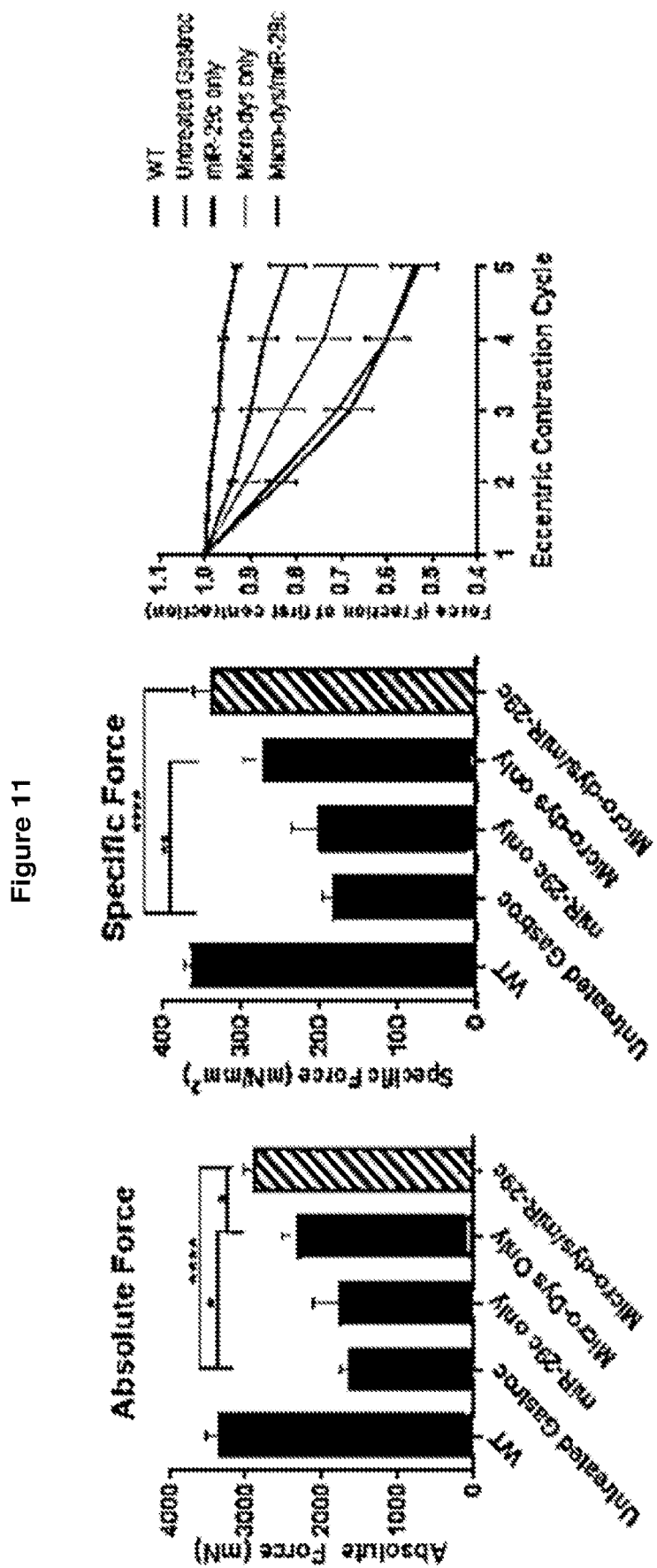

FIG. 11 demonstrates early combination therapy restores force and protects against contraction-induced damage. Measurement of absolute (panel A) and normalized specific force (panel b) following tetanic contraction in all three treatment injected GAS muscles were significantly increased compared to untreated mdx/utrn$^{+/-}$ muscle (panel C). Muscles were then assessed for loss of force following repetitive eccentric contractions. Only mice co-treated with miR-29c/micro-dystrophin and micro-dystrophin alone showed a protection from loss of force compared with untreated mdx/utrn$^{+/-}$ muscles (blue). Two-way analysis of variance demonstrates significance in decay curves Error bars, SEM for n=5 (rAAVrh.74.CMV.miR-29c), n=6 (rAAVrh.74.CMV.miR-29c/rAAVrh.74.MCK.micro-dystrophin), n=5 (rAAVrh.74.MCK.micro-dystrophin), n=15 (mdx/utrn+/− mice). 1-way ANOVA ($*p<0.05, p<0.01, *p<0.001, ****p<0.0001$).

Figure 12:
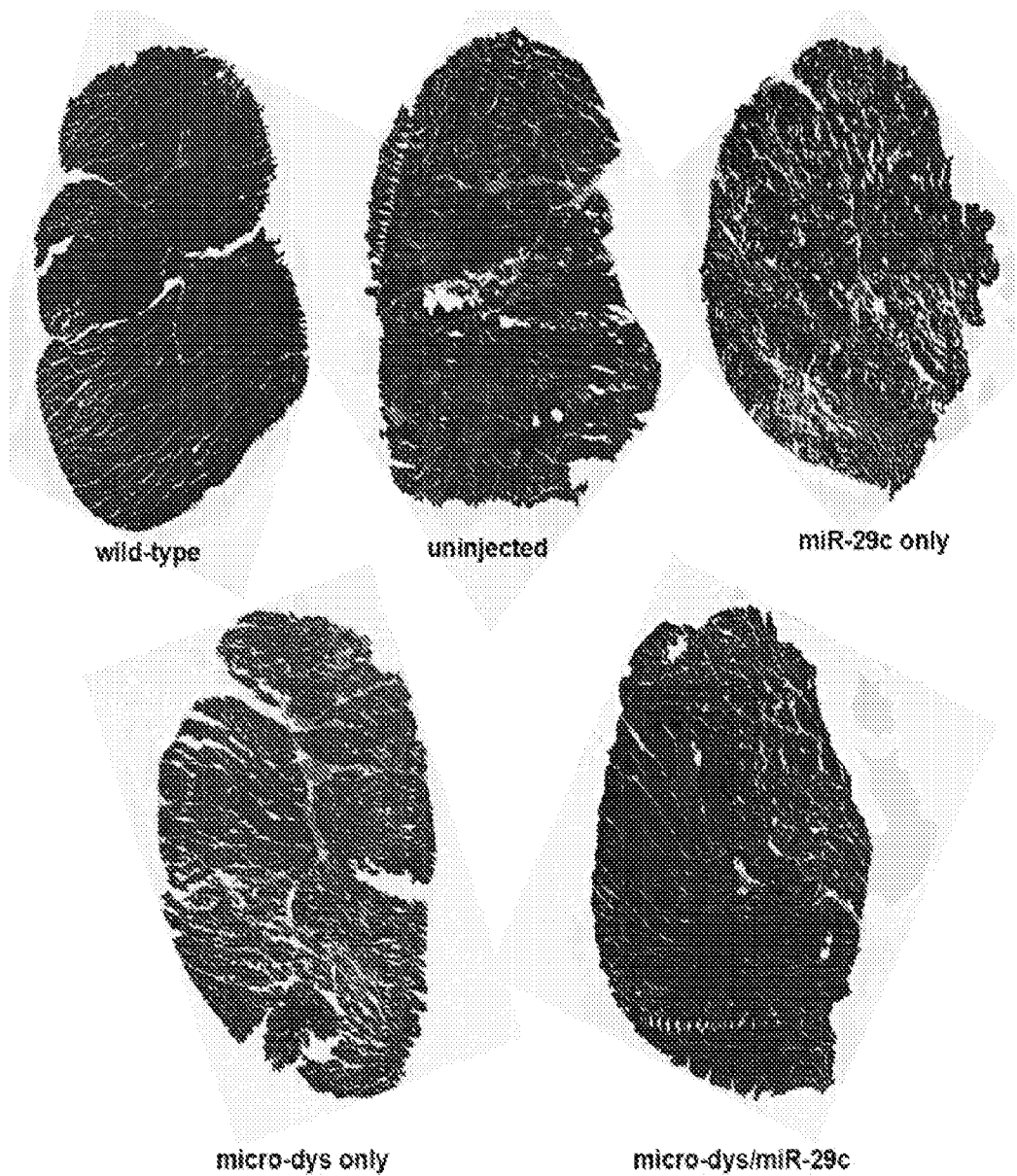

FIG. 12 illustrates miR-29c/micro-dystrophin combination treatment increases muscle size in mice treated at 1 month of age. Treated and untreated mdx/utrn$^{+/-}$ GAS muscles were sectioned and staining with picrosirius Red to stain for collagen. Fibrotic areas are pink and intact muscle is in green. On the macroscopic level, miR-29c/micro-dystrophin combination decreases fibrosis and increases total cross sectional area.

FIG. 13A-13G demonstrates that early treatment (at 4-5 weeks) of AAV.MCK.miR-29c/micro-dystrophin combination therapy is more effective at reducing fibrosis and ECM expression. Panel A provide picrosirius red staining of uninjected and AAV.MCK.miR-29c/AAV.MCK.micro-dystrophin of mice injected at 4-5 wks of age taken out twelve weeks post-injection. Original magnification, ×20 Panel B provides quantification of picrosirius red staining demonstrating co-treated muscle had a 50.9% reduction in collagen compared to untreated GAS muscle Panel C provides qRT-PCR confirming an increase in miR-29c transcript levels in the treated cohort. Semi-quantitative qRT-PCR shows a significant reduction in Collagen 1A (Col1A; panel D) and Collagen 3A (Col3A; panel E), Fibronectin (Fbn; panel F) and Tgfβ1 (panel G) levels in the AAV.MCK.miR-29c/AAV.micro-dystrophin treated muscle compared to the contralateral limb therapies. ($*p<0.05,****p<0.0001$).

FIG. 14A-14G demonstrates that late treatment (treatment at 12 weeks) with AAV.MCK.miR-29c/micro-dystrophin combination therapy is effective at reducing fibrosis and ECM expression. Panel A provides picrosirius red staining of untreated, AAV.MCK.miR-29c and AAV.MCK.miR-29c/AAV.micro-dystrophin twelve weeks post-injection. Original magnification, ×20. Panel B provides quantification of picrosirius red staining which demonstrates that co-treated muscle had a 30.3% reduction in collagen compared to untreated GAS muscle. Panel C provides qRT-PCR confirming an increase in miR-29c transcript levels in the treated cohorts. Semi-quantitative qRT-PCR demonstrated a significant reduction in Collagen 1A (Col1A; panel D), Collagen 3A (Col3A; panel E), Fibronectin (Fbn; Panel F) and Tgfβ1 (panel G) levels in the AAV.miR-29c/AAV.micro-dystrophin treated muscle compared to the contralateral limb. One-way ANOVA. All data represent mean±SEM. ($p<0.01$, $**p<0.0001$).

Figure 15A:
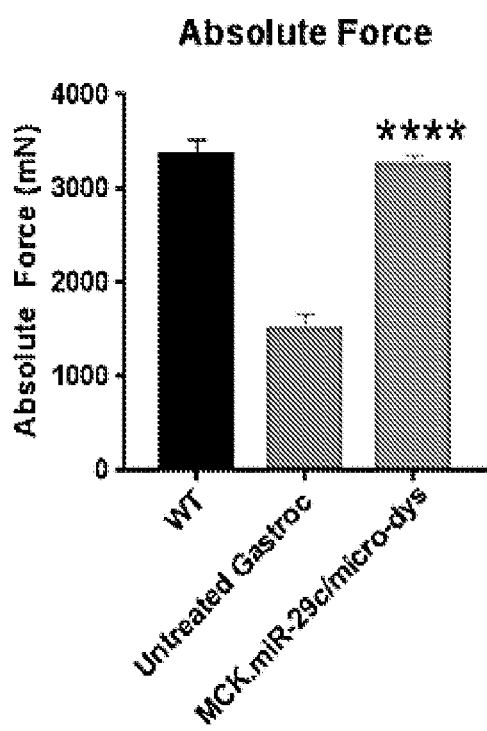
Figure 15B:
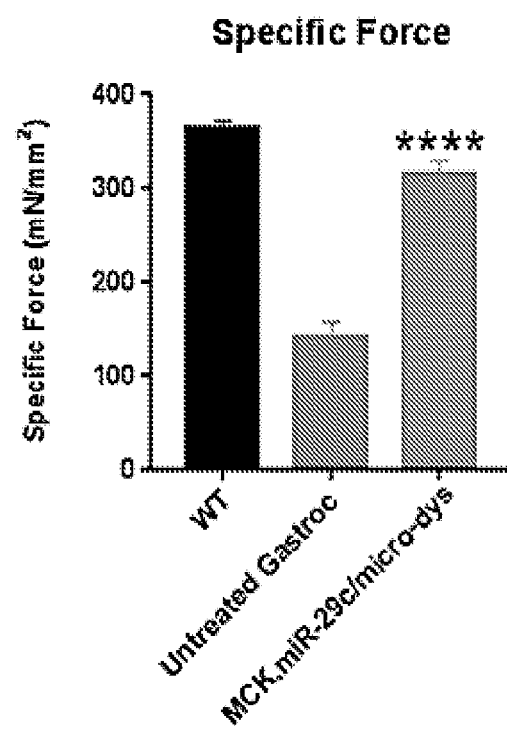
Figure 15C:
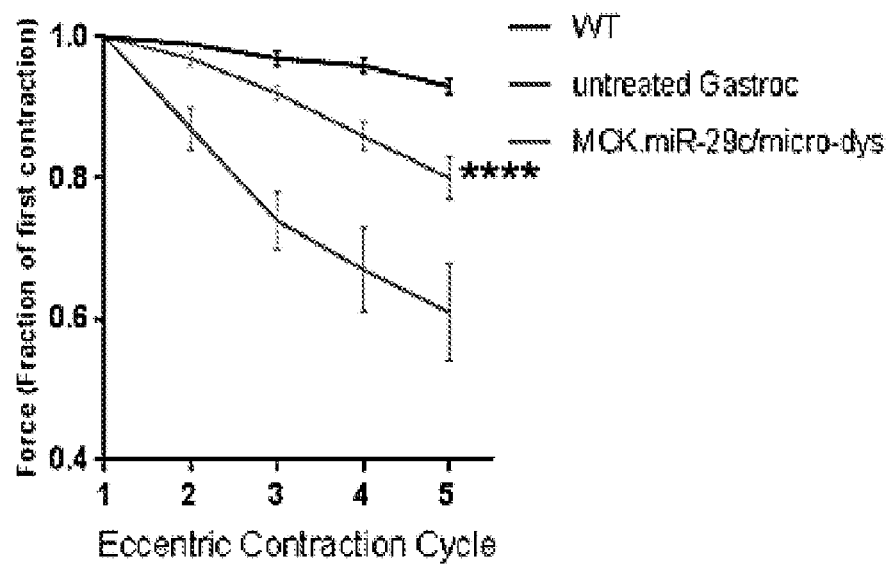

FIG. 15A-15C demonstrates that early combination therapy (treatment at 4-5 weeks) restored force and protected against contraction-induced damage. Measurement of absolute (panel A) and normalized specific force (panel B) following tetanic contraction MCK.miR-29c/micro-dystrophin injected GAS muscles were significantly increased compared to untreated mdx/utrn$^{+/-}$ muscle. (C) Muscles were then assessed for loss of force following repetitive eccentric contractions. Mice co-treated with miR-29c/micro-dystrophin and micro-dystrophin alone showed protection from loss of force compared with untreated mdx/utrn$^{+/-}$ muscles (red). Two-way ANOVA. All data represent mean±SEM ($****p<0.0001$).

Figure 16A:
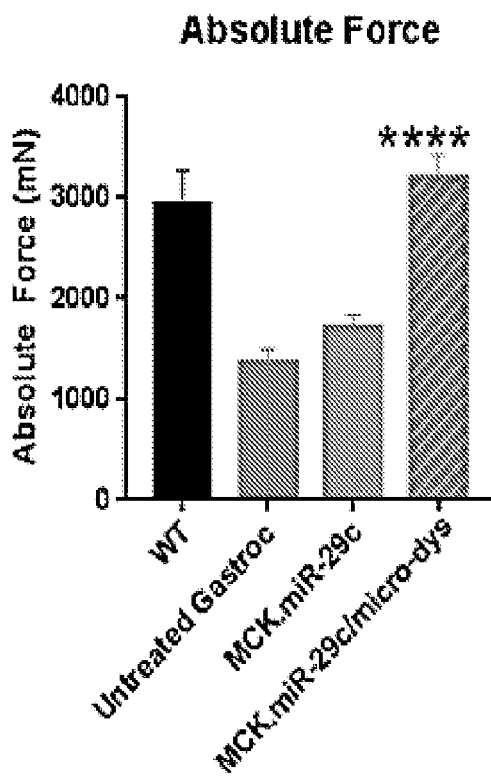
Figure 16B:
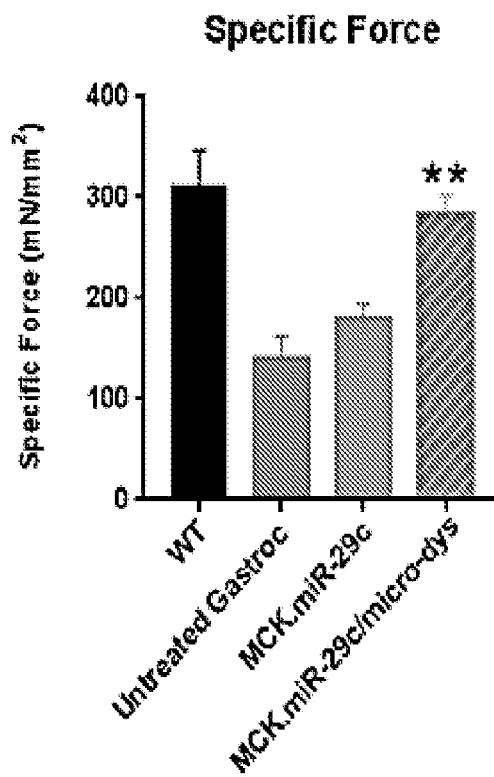
Figure 16C:
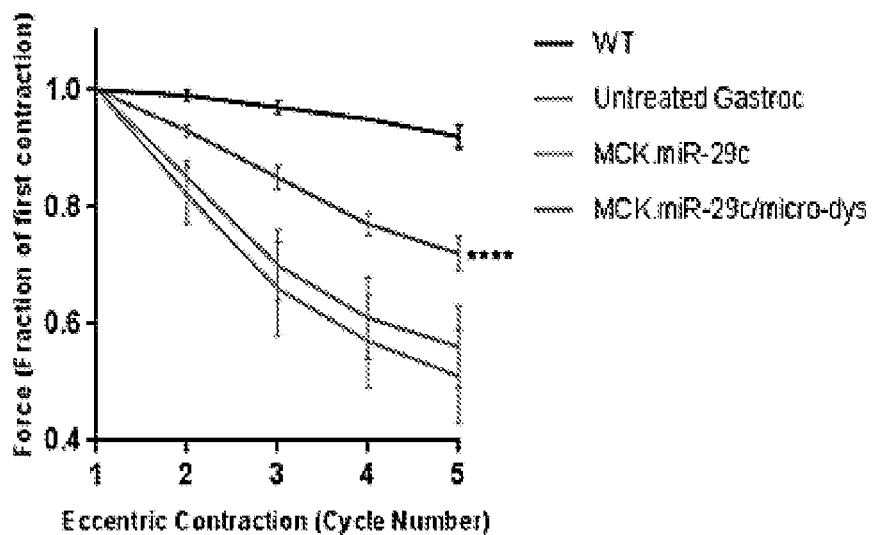

FIG. 16A-16C demonstrates that late combination therapy restored force and protected against contraction-induced damage. Measurement of absolute (panel A) and normalized specific force (panel B) following tetanic contraction rAAV.MCK.miR-29c and rAAV expressing micro-dystrophin injected GAS muscles were significantly increased compared to untreated mdx/utrn$^{+/-}$ muscle. In Panel C, muscles were then assessed for loss of force following repetitive eccentric contractions. Mice co-treated with rAAV.MCK.miR-29c/rAAV expressing micro-dystrophin showed a protection from loss of force compared with untreated mdx/utrn$^{+/-}$ muscles (red). Two-way ANOVA. All data represent mean±SEM ($p<0.01$, $**p<0.0001$).

FIG. 17A-17D demonstrates that combination treatment increases muscle hypertrophy 3 months post injection. Panel A demonstrates that rAAV. MCK.miR-29c co-delivered with rAAV expressing micro-dystrophin failed to increase the overall weight of the injected GAS. Panel B demonstrates that rAAV.MCK.miR-29c/rAAV expressing micro-dystrophin combination treatment induced an increase in average fiber size. Comparing mdx/utrn$^{+/-}$ controls with miR-29c/micro-dystrophin treated mdx/utrn$^{+/-}$, the average diameter increased from 28.96 to 36.03 µm. Panel C shows that co-delivery produced a shift towards wild-type fiber size distribution. Panel D provided the number of muscle fibers per mm² in the miR-29c/micro-dystrophin combination treatment was significantly less than untreated mice and wild-type (*p<0.01, **p<0.0001).

FIG. 18A-18B provides the nucleic acid sequence (SEQ ID NO: 1 pAAV.CMV.Mir29C) of an exemplary rAAV vector comprising the mature guide strand of miR-29c (nucleotides 1257-1284) and the natural mi-30 backbone (nucleotides 1088-1375). The construct also comprises the CMV promoter (nucleotides 120-526), two EF1a introns at nucleotides 927-1087 and 1380-1854 and a polA at nucleotides 1896-2091.

Figure 19:
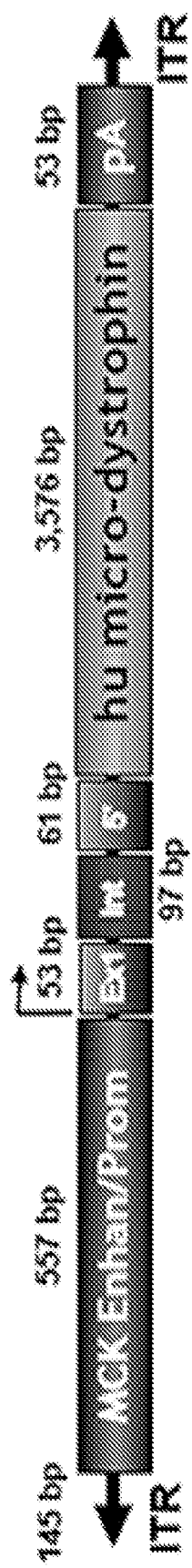

FIG. 19 provides a schematic of the rAAV vector pAAV.MCK.micro-dystrophin.

FIG. 20A-D provides the nucleic acid sequence (SEQ ID NO: 9; pAAV.MCK.micro-dystrophin) of an exemplary rAAV vector expressing micro-dystrophin.

FIG. 21A-21C provides the nucleotide sequence of the human micro-dystrophin nucleotide sequence (SEQ ID NO: 7)

FIG. 22 provides the nucleotide sequence (SEQ ID NO: 12 pAAV.MCK.Mir29C) of an exemplary rAAV vector comprising the mature guide strand of miR-29c (nucleotides 1487-1512) and the natural mi-30 backbone (nucleotides 1088-1375). The construct also comprises the MCK enhancer (nucleotides 190-395), MCK promoter (nucleotides 396-753), two EF1a introns at nucleotides 1155-1315 and 1609-2083 and a polA at nucleotides 2094-2148.

DETAILED DESCRIPTION

The present invention provides for gene therapy vectors, e.g. rAAV vectors, overexpressing miR-29 microRNA and methods of reducing and preventing fibrosis in muscular dystrophy patients. The present invention also provides for combination gene therapy methods which comprise administering a gene therapy vector expressing miR-29 in combination with a gene therapy vector expressing micro-dystrophin that is deleted in DMD patients.

Muscle biopsies taken at the earliest age of diagnosis of DMD reveal prominent connective tissue proliferation. Muscle fibrosis is deleterious in multiple ways. It reduces normal transit of endomysial nutrients through connective tissue barriers, reduces the blood flow and deprives muscle of vascular-derived nutritional constituents, and functionally contributes to early loss of ambulation through limb contractures. Over time, treatment challenges multiply as a result of marked fibrosis in muscle. This can be observed in muscle biopsies comparing connective tissue proliferation at successive time points. The process continues to exacerbate leading to loss of ambulation and accelerating out of control, especially in wheelchair-dependent patients.

Without a parallel approach to reduce fibrosis it is unlikely that the benefits of exon skipping, stop-codon read-through, or gene replacement therapies can ever be fully achieved. Even small molecules or protein replacement strategies are likely to fail without an approach to reduce muscle fibrosis. Previous work in aged mdx mice with existing fibrosis treated with AAV.micro-dystrophin demonstrated that we could not achieve full functional restoration (*Human molecular genetics* 22, 4929-4937 (2013)). It is also known that progression of DMD cardiomyopathy is accompanied by scarring and fibrosis in the ventricular wall. Micro-RNA delivery is particularly innovative because of lack of immune barriers and relative ease of delivery. MicroRNAs are small (~200 bp) and can therefore be packaged in AAV along with a therapeutic cassette to correct or bypass the genetic defect.

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized. General information and reviews of AAV can be found in, for example, Carter, 1989, Handbook of Parvoviruses, Vol. 1, pp. 169-228, and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

AAV

Recombinant AAV genomes of the invention comprise nucleic acid molecule of the invention and one or more AAV ITRs flanking a nucleic acid molecule. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11, AAV-12 and AAV-13. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014). As noted in the Background section above, the nucleotide sequences of the genomes of various AAV serotypes are known in the art. To promote skeletal muscle specific expression, AAV1, AAV6, AAV8 or AAVrh.74 may be used.

DNA plasmids of the invention comprise rAAV genomes of the invention. The DNA plasmids are transferred to cells permissible for infection with a helper virus of AAV (e.g., adenovirus, E1-deleted adenovirus or herpes virus) for assembly of the rAAV genome into infectious viral particles. Techniques to produce rAAV particles, in which an AAV genome to be packaged, rep and cap genes, and helper virus functions are provided to a cell, are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAVrh.74, AAV-8, AAV-9, AAV-10, AAV-11, AAV-12 and AAV-13. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV (i.e., infectious encapsidated rAAV particles) of the invention comprise a rAAV genome. In exemplary embodiments, the genomes of both rAAV lack AAV rep and cap DNA, that is, there is no AAV rep or cap DNA between the ITRs of the genomes. Examples of rAAV that may be constructed to comprise the nucleic acid molecules of the invention are set out in International Patent Application No. PCT/US2012/047999 (WO 2013/016352) incorporated by reference herein in its entirety.

The rAAV may be purified by methods standard in the art such as by column chromatography or cesium chloride gradients. Methods for purifying rAAV vectors from helper virus are known in the art and include methods disclosed in, for example, Clark et al., Hum. Gene Ther., 10(6): 1031-1039 (1999); Schenpp and Clark, Methods Mol. Med., 69 427-443 (2002); U.S. Pat. No. 6,566,118 and WO 98/09657.

In another embodiment, the invention contemplates compositions comprising rAAV of the present invention. Compositions of the invention comprise rAAV and a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counter ions such as sodium; and/or nonionic surfactants such as Tween, pluronics or polyethylene glycol (PEG).

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg).

Methods of transducing a target cell with rAAV, in vivo or in vitro, are contemplated by the invention. The in vivo methods comprise the step of administering an effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the invention is FSHD.

Combination therapies are also contemplated by the invention. Combination as used herein includes both simultaneous treatment and sequential treatments. Combinations of methods of the invention with standard medical treatments (e.g., corticosteroids) are specifically contemplated, as are combinations with novel therapies.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the invention may be chosen and/or matched by those skilled in the art taking into account the infection and/or disease state being treated and the target cells/tissue(s) that are to express the miR-29 miRNA and/or micro-dystrophin.

The invention provides for local administration and systemic administration of an effective dose of rAAV and compositions of the invention including combination therapy of the invention. For example, systemic administration is administration into the circulatory system so that the entire body is affected. Systemic administration includes enteral administration such as absorption through the gastrointestinal tract and parental administration through injection, infusion or implantation.

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling.

The dose of rAAV to be administered in methods disclosed herein will vary depending, for example, on the particular rAAV, the mode of administration, the treatment goal, the individual, and the cell type(s) being targeted, and may be determined by methods standard in the art. Titers of each rAAV administered may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$, about $1\times10^{14}$, or to about $1\times10^{15}$ or more DNase resistant particles (DRP) per ml. Dosages may also be expressed in units of viral genomes (vg) (i.e., $1\times10^7$ vg, $1\times10^8$ vg, $1\times10^9$ vg, $1\times10^{10}$ vg, $1\times1011$ vg, $1\times1012$ vg, $1\times1013$ vg, $1\times1014$ vg, $1\times1015$ respectively). Dosages may also be expressed in units of viral genomes (vg) per kilogram (kg) of bodyweight (i.e., $1\times10^{10}$ vg/kg, $1\times10^{11}$ vg/kg, $1\times10^{12}$ vg/kg, $1\times10^{13}$ vg/kg, $1\times10^{14}$ vg/kg, $1\times10^{15}$ vg/kg respectively). Methods for titering AAV are described in Clark et al., Hum. Gene Ther., 10: 1031-1039 (1999).

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxypropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical carriers, diluents or excipients suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the invention results in sustained expression of miR-29 or micro-dystrophin. The present invention thus provides methods of administering/delivering rAAV which express of miR-29 and or micro-dystrophin to an animal, preferably a human being. These methods include transducing tissues (including, but not limited to, tissues such as muscle, organs such as liver and brain, and glands such as salivary glands) with one or more rAAV of the present invention. Transduction may be carried out with gene cassettes comprising tissue specific control elements. For example, one embodiment of the invention provides methods of transducing muscle cells and muscle tissues directed by muscle specific control elements, including, but not limited to, those derived from the actin and myosin gene families, such as from the myoD gene family [See Weintraub et al., Science, 251: 761-766 (1990], the myocyte-specific enhancer binding factor MEF-2 [Cserjesi and Olson, Mol Cell Biol 11: 4854-4862 (1990], control elements derived from the human skeletal actin gene [Muscat et al., Mol Cell Biol, 7: 4089-4099 (1987)], the cardiac actin gene, muscle creatine kinase sequence elements [See Johnson et al., Mol Cell Biol, 9:3393-3399 (1989)] and the murine creatine kinase enhancer (mCK) element, control elements derived from the skeletal fast-twitch troponin C gene, the slow-twitch cardiac troponin C gene and the slow-twitch troponin I gene: hypoxia-inducible nuclear factors (Semenza et al., Proc Natl Acad Sci USA, 88: 5680-5684 (1991)), steroid-inducible elements and promoters including the glucocorticoid response element (GRE) (See Mader and White, Proc. Natl. Acad. Sci. USA 90: 5603-5607 (1993)), and other control elements.

Muscle tissue is an attractive target for in vivo DNA delivery, because it is not a vital organ and is easy to access. The invention contemplates sustained expression of miR-NAs from transduced myofibers.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts.

The term "transduction" is used to refer to the administration/delivery of the miiR29 guide strand or the coding region of the micro-dystrophin to a recipient cell either in vivo or in vitro, via a replication-deficient rAAV of the invention resulting in expression of a miR29 or micro-dystrophin by the recipient cell.

Thus, the invention provides methods of administering an effective dose (or doses, administered essentially simultaneously or doses given at intervals) of rAAV that encode miR29 and/or micro-dystrophin to a patient in need thereof.

EXAMPLES

Example 1

Confirmation of Duchenne Muscular Dystrophy Models

The mdx mouse provides a convenient, yet incomplete, animal model to study DMD pathogenesis. This model is a cross of the mdx mouse with a heterozygous knockout of the utrophin gene (mdx:utrn+/−), which presents with increased fibrosis and more faithfully recapitulates the pathology of human DMD. Mdx mice have a nonsense mutation in exon 23 of DMD that results in a relatively mild phenotype and a near-normal life span. By 3 weeks of age, the diaphragm and limb muscle of mdx mice develop signs of endomysial inflammation. These symptoms subside in the limb muscle after the mice reach adulthood while the inflammation in the diaphragm muscle continues to progressively worsen. In mdx mice lacking telomerase, muscular dystrophy progressively worsens with age; mdx mice lacking utrophin (DKO) have a phenotype more characteristic of human DMD with early onset muscle weakness, severe fibrosis, and premature death. Utrophin, an autosomal paralog of the dystrophin, shares a high degree of sequence homology that may compensate for the lack of dystrophin in the mdx mouse in the double KO (dystrophin plus utrophin); a severe phenotype with early death is observed. The premature death in the DKO mouse precludes progression of inflammation and fibrosis, but the mdx:utrn$^{+/-}$ mouse presents a model with similarities to the human disease exhibiting a striking degree of fibrosis, and a longer survival than the DKO, providing a better model for our proposed translational studies. A recent report confirms the use of the mdx:utrn$^{+/-}$ mouse as an ideal model to study fibrosis in the context of DMD. In the present study, increased fibrosis as measured by Sirius red staining was accompanied by increased collagen transcript levels and decreased mir29c levels.

Example 2

Delivery of miR29 to DMD Mice Reduces Fibrosis

Preliminary studies have demonstrated that there is a significant increase in Sirius Red staining for collagen and a decrease in miR-29c levels in human DMD patients and the mdx/utrn$^{+/-}$ mouse. Gene delivery of miR-29 using muscle specific AAV vectors is potentially safe and efficient. To generate the rAAV vector, referred to herein as rAAVrh.74.CMV.miR29c, the 22 nucleotide miR29c sequence (target strand SEQ ID NO: 3 and guide strand SEQ ID NO: 4) was cloned into a miR-30 scaffold driven by a CMV promoter. The expression cassette (SEQ ID NO: 2) was cloned into a self-complementary AAV plasmid and packaged using AAVrh.74, a serotype known to express well in muscle. The miR-29c cDNA was synthesized using a custom primer containing the miR-29c target (sense) strand, miR-30 stem loop and miR-29c guide (antisense) strand in the miR-30 backbone. Three bases of the miR-29c sequence were modified. This sequence was then cloned into a self-complementary AAV ITR containing plasmid driven by the CMV promoter and polyA sequence.

As shown in FIG. 1, the pAAV.CMV.miR29C plasmid contains the mir29c cDNA in a miR-30 stem loop backbone flanked by AAV2 inverted terminal repeat sequences (ITR). It is this sequence that was encapsidated into AAVrh.74 virions. In addition, a few nucleotides with in the miR-29c target sequence were changed to mimic Watson-crick pairing at this site as in shRNA-miR(luc). According to ShRNA-luc design, the hairpin should be perfectly complementary throughout its length. Plus, the more changes to the passenger strand, the more likely the elimination of any endogenous mechanism that regulates miR-29 processing that could recognize the miRNA via the stem. The $19^{th}$ base of the guide strand was modified to a cytosine to mimic the nucleotide that precedes the cleavage site in natural mi-29c sequence and the corresponding base on the other strand was changed to preserve pairing.

The gene therapy vector scrAAVrh.74.CMV.miR29c ($1\times10^{11}$ vgs) was injected into the quadriceps muscle of 3 month old mdx/utrn$^{+/-}$ mice. Quadriceps muscle was analyzed 3 months post-injection by Sirius Red staining and analyzed by NIH ImageJ software as described in Nevo et al. (PloS One, 6: e18049 (2011). MiR29c, collagen and elastin levels were quantified by RT-PCR. Delivery of miR-29c to young mdx/utrn$^{+7}$ mice significantly increases mir-29c levels and a significant reduction in Sirius red staining in the quadriceps muscle of 6 month old mdx/utrn$^{+/-}$ mice (3 months post injection). There was a reduction in collagen and elastin levels in the treated muscles when evaluated by RT-PCR.

Demonstration of increased fibrosis and decreased miR29 expression in the mdx/utrn$^{+/-}$ mice and dystrophin-deficient patients validates the mouse model as being representative of the human disease. Initial results using AAV-delivered miR29 as an anti-fibrotic therapy suggest that there is significant beneficial effect with reduction in Sirius Red staining and collagen and elastin levels, which are key contributors in fibrosis.

Example 3

Injection of MiR-29c Reduces Collagen and Restores miR-29c

Figure 2A:
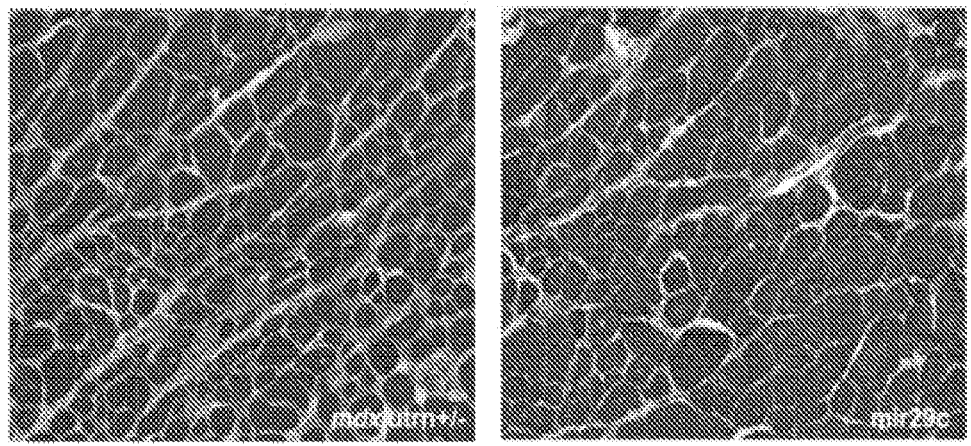
FIG. 2A-2C illustrates that injection of miR-29c into muscle reduces collagen throughout the muscle and restores miR-29c expression.
Figure 2B:
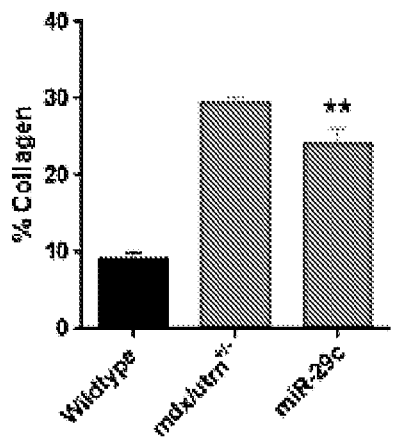
Figure 2C:
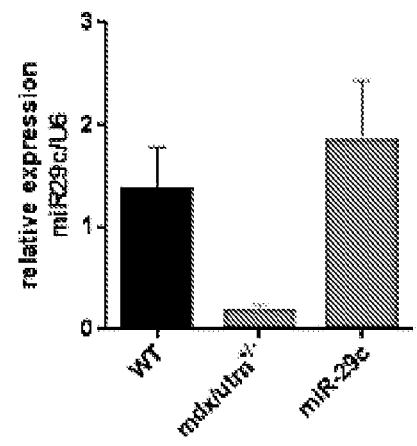

To determine whether rAAVrh.74.CMV.MiR-29c could reduce fibrosis, 12-week-old mdx/utrn$^{+/-}$ mice received an intramuscular injection of rAAVrh.74.CMV.MiR-29c at $5\times10^{11}$ vgs to the left gastrocnemius (GAS) muscle. The mice were analyzed at 12 weeks post injection. Picrosirius red staining revealed a significant decrease in collagen staining throughout the GAS muscles (FIG. 2a) compared to the untreated contralateral mdx/utrn+/− GAS muscle. Quantification of the picrosirius red staining shows that treated muscle had a 18.3% reduction in collagen compared to the untreated muscle (treated—23.3%±1.3 vs. untreated—29.5%±0.7)(FIG. 2b). To confirm overexpression of miR-29c in treated muscle, total RNA was extracted from the GAS muscle from 24 week old WT, miR-29c treated and mdx/utrn$^{+/-}$ mice and subjected to quantitative reverse-transcription PCR (qRT-PCR) analysis for miR-29c expression. The results showed that miR-29c was significantly increased in the GAS muscle of the treated mice compared to untreated mice (FIG. 2d).

Example 4

MiR-29c Improves Absolute and Specific Muscle Force but does not Protect Against Contraction-Induced Damage Knowing that fibrosis can impact muscle function, we wanted to test whether reducing fibrosis by increasing expression of MiR-29c could protect mdx/utrn$^{+/-}$ muscle from contraction-induced injury and increase overall force. The functional properties of the gastrocnemius muscle from mdx/utrn$^{+/-}$ mice treated with rAAVrh.74.CMV.MiR-29c were assessed. Twelve weeks post injection, the GAS was isolated to perform in vivo force measurements.

The GAS procedure follows the protocol listed in Hakim et al., (Methods Mol Biol. 709: 75-89, 2011) for analyzing transverse abdominal muscle physiology but adapted for the GAS. Briefly, mice were anesthetized using ketamine/xylazine mixture. The hind limb skin was removed to expose the GAS muscle and the Achilles tendon. The distal tendon was dissected out and a double square knot was tied around the tendon with 4-0 suture as close to the muscle as possible, another second double square knot is tied right next to the first knot and then tendon is cut. The exposed muscle was constantly dampened with saline. Mice were then transferred to a thermal controlled platform and maintained at 37°. The knee was secured to the platform with a needle through the patella tendon, the tendon suture to the level arm of the force transducer (Aurora Scientific, Aurora, ON, Canada), and the foot was secured with tape. The GAS muscle contractions were elicited by stimulating the sciatic nerve via bipolar platinum electrodes. Once the muscle was stabilized, the optimal length was determined by incremental stretching the muscle until the maximum twitch force was achieved. After a 3-minute rest period, the GAS was stimulated at 50,100,150, and 200 Hz, allowing a 1-minute rest period between each stimulus to determine maximum tetanic force. Muscle length was measured. Following a 5-minute rest, the susceptibility of the GAS muscle to contraction-induced damage was assessed. After 500 ms of stimulation, the muscle was lengthened by 10% of the optimal length. This consisted of stimulating the muscle at 150 Hz for 700 ms. After the stimulation, the muscle was returned to the optimal length. The cycle was repeated every minute for a total of 5 cycles. Specific force was calculated by dividing the maximum tetanic force by the GAS muscle cross sectional area. After the eccentric contractions, the mice were then euthanized and the GAS muscle was dissected out, weighed and frozen for analysis.

Figure 3A:
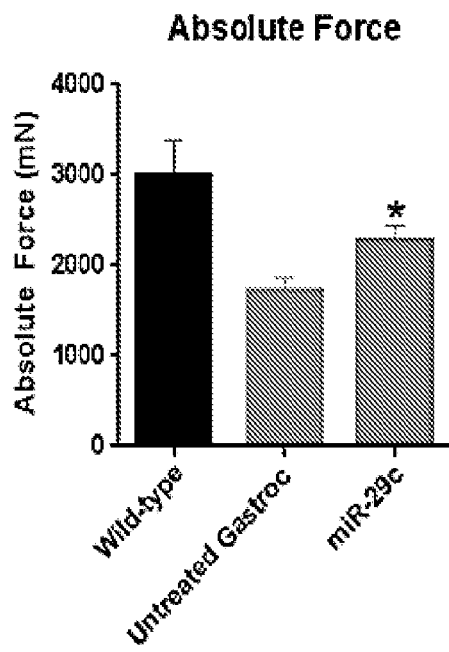
FIG. 3A-3C demonstrates that injection of miR-29c improves absolute muscle force (panel A) and specific muscle force (panel B) but does not protect against contraction-induced damage (panel C).
Figure 3B:
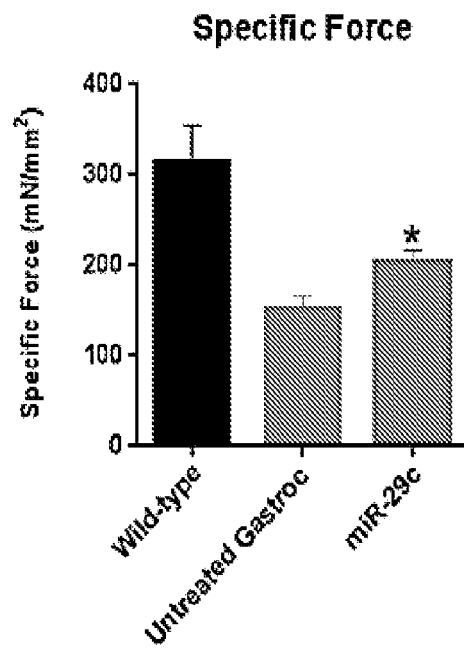
Figure 3C:
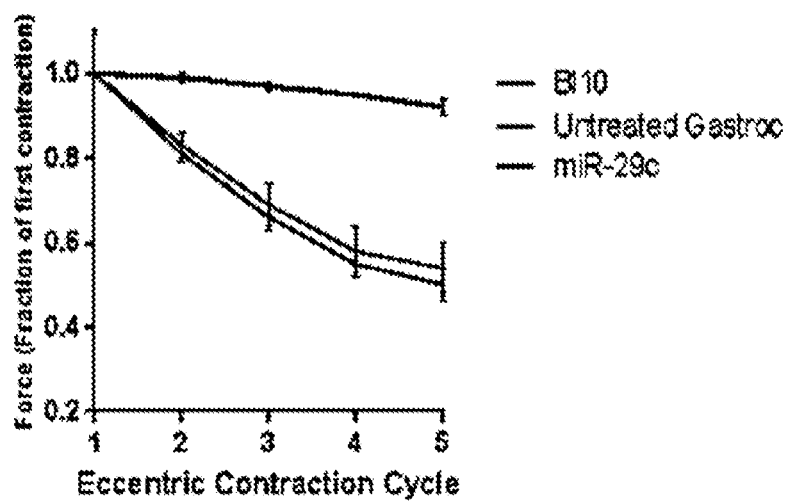

Each GAS was subjected to a series of repeated eccentric contraction. By comparing the force ratio of each contraction versus the first contraction revealed that after the fifth contraction untreated muscle decayed to 0.56±0.05 versus treated 0.50±0.04 (p≤0.0001). The injected group showed a slight decrease in the degree of protection compared to WT controls, that decayed to 0.92±0.02 (FIG. 3c). This data shows that reducing fibrosis by increasing expression of miR-29c leads to increase in both absolute and specific force but does not significantly protect muscle from contraction-induced injury.

rAAVrh.74.MiR-29c treated GAS muscle showed significant improvement in absolute force when compared to untreated mdx/utrn$^{+/-}$ GAS muscle (rAAV.miR-29c—2277±161.7 vs. mdx/utrn$^{+/-}$ untreated—1722±145.7; FIG. 3a), and also normalized specific force in rAAVrh.74.miR-29c treated GAS muscle specific improvement when compared to untreated GAS muscle (rAAV.miR-29c—204.7±11.7 vs. mdx/utrn$^{+/-}$ untreated—151.6±14.5; FIG. 3b). Force was still significantly reduced when compared to wild-type controls (rAAV.miR-29c—204.7±11.7 vs. wild-type—312.0±34.1).

Example 5

Co-Delivery with Micro-Dystrophin Further Reduces Fibrosis

To determine whether miR-29c/micro-dystrophin combined gene therapy approach would be more beneficial at reducing fibrosis, 12-week-old mdx/utrn$^{+/-}$ mice received an intramuscular injection of rAAVrh.74.CMV.MiR-29c at $5 \times 10^{11}$ vgs to the left gastrocnemius muscle. The following gene therapy vectors were administered by intramuscular injection (IM) into the left gastrocnemius (GAS) muscle of 3 month old mdx/utrn$^{+/-}$ mice, a DMD mouse model: scAAVrh.74.CMV.miR-29c alone, co-delivered with rAAVrh.74.MCK.micro-dystrophin, and rAAVrh.74.MCK.micro-dystrophin alone.

The pAAV.MCK.micro-dystrophin plasmid contains the human micro-dystrophin cDNA expression cassette flanked by AAV2 inverted terminal repeat sequences (ITR) as shown in FIG. 10. It is this sequence that was encapsidated into AAV rh.74 virions. The pAAV.MCK.micro-dystrophin plasmid was constructed by inserting the MCK expression cassette driving a codon optimized human micro-dystrophin cDNA sequence into the AAV cloning vector as described in Rodino-Klapac et al. (Mol Ther. 2010 January; 18(1):109-17). A MCK promoter/enhancer sequence was used to drive muscle-specific gene expression and is composed of the mouse MCK core enhancer (206 bp) fused to the 351 bp MCK core promoter (proximal). After the core promoter, the 53 bp endogenous mouse MCK Exon1 (untranslated) is present for efficient transcription initiation, followed by the SV40 late 16S/19S splice signals (97 bp) and a small 5'UTR (61 bp). The intron and 5' UTR are derived from plasmid pCMVß (Clontech). The micro-dystrophin cassette has a consensus Kozak immediately in front of the ATG start and a small 53 bp synthetic polyA signal for mRNA termination. The human micro-dystrophin cassette contains the (R4-R23/Δ71-78) domains. The complementary DNA was codon optimized for human usage and synthesized by GenScript (Piscataway, N.J.).

Figure 4C:
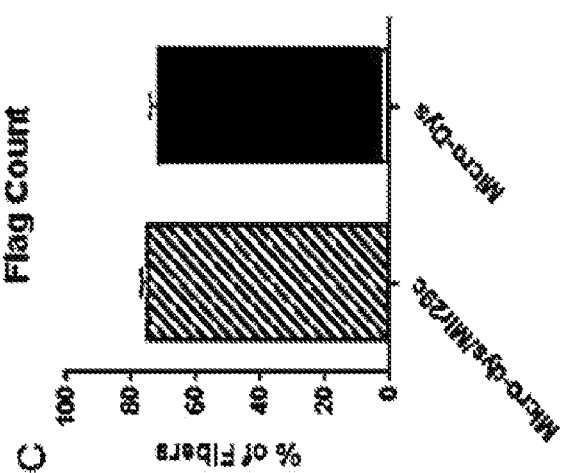
FIG. 4A-4C displays the number of muscle fibers expression micro-dystrophin to measure of efficacy of transgene delivery.
Figure 4B:
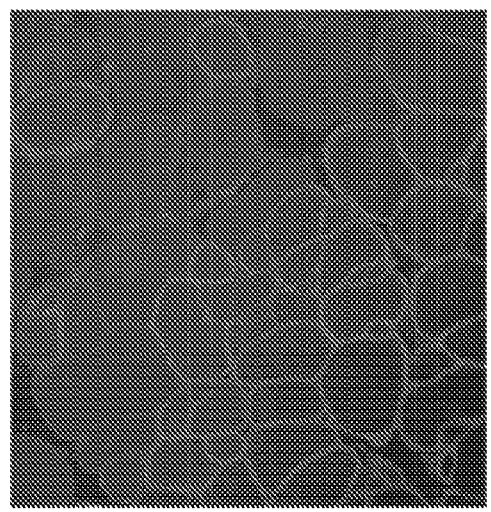
Figure 4A:
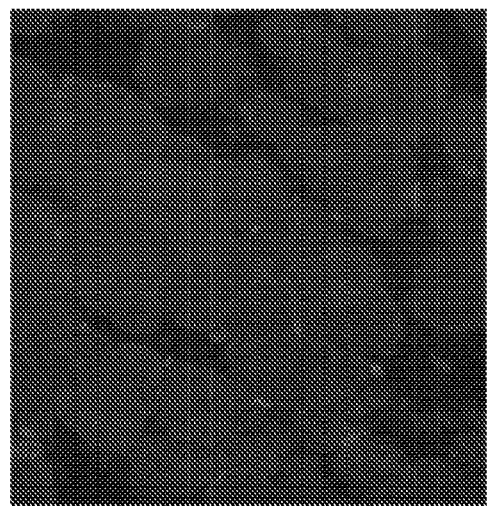

The mice were analyzed at 12 and 24 weeks post injection. First, the number of muscle fibers expressing micro-dystrophin was used to assess the efficacy of transgene delivery and to make sure we had similar levels of micro-dystrophin expressed in each group. We found that micro-dystrophin was not different between cohorts treated with micro-dystrophin alone (71.85±2.25%) compared with miR-29c/micro-dystrophin combination therapy (75.03±1.91%) (FIG. 4).

GAS muscle was analyzed 12 months post-injection to assess collagen accumulation by Sirius Red staining and subsequent quantification with ImageJ. Additional outcomes included miR-29c and collagen transcript levels, force measurements in the GAS muscle, fiber diameter measurements and western blot analysis for proteins involved in muscle regeneration (MyoD, Myogenin). The amount of fibrosis was analyzed by picrosirius red staining, which revealed a significant decrease in collagen staining throughout the GAS muscles in all treated groups (FIG. 5a) compared to the untreated contralateral mdx/utrn+/− GAS muscle or micro-dystrophin alone. Quantification of the picrosirius red staining shows that co-treated muscle had a 40.8% reduction in collagen compared to the untreated muscle (treated—17.47%±0.75 vs. untreated-29.5%±0.7) (FIG. 5b). To confirm expression of miR-29c, qRT-PCR was performed on the GAS muscle and all treatment groups had an increase in miR-29c compared to untreated muscle (FIG. 5c).

Analogous to DMD tissue, a significant reduction in miR-29c levels in mdx/utrn$^{+/-}$ muscle was observed which correlated with increased fibrosis measured by picrosirius red staining. Following 3 months of treatment with scAAV.miR-29c alone, there was a significant reduction in fibrosis (treated-23.5%±1.3 vs. untreated-27.8%±0.6) in the GAS muscle. When co-delivered with micro-dystrophin, further reduction in collagen (41%) was observed by picrosirius red staining (combination treatment: 17.47%±0.75 vs. untreated: 29.5%±0.7) (p<0.0001) (FIG. 5b). To confirm expression of miR-29c, qRT-PCR was performed on the GAS muscle and all treatment groups had an increase in miR-29c compared to untreated muscle (FIG. 5b).

At 24 weeks post-injection, the results were similar to those observed 12 weeks post injection. There was a 47% reduction in collagen by picrosirius red staining compared to the untreated muscle (combination treatment: 16.5±1.23 vs. untreated: 31.07±0.93; p<0.0001) and a coincident increase in miR-29c transcript level.

Figure 6A:
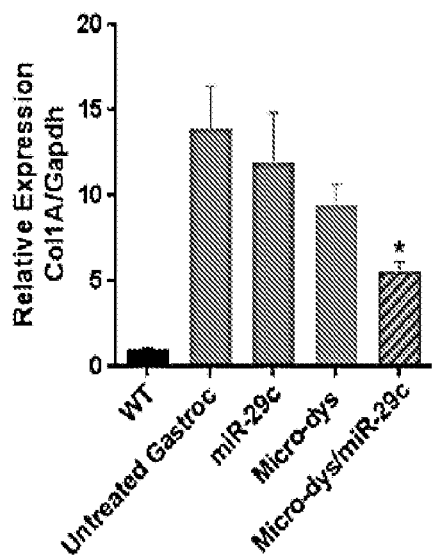
FIG. 6A-6D illustrates that intramuscular injection of miR-29c/micro-dystrophin inhibits extracellular matrix (ECM) in mdx/utrn$^{+/-}$ mice as measured by collagen 1 alpha (panel A), collagen 3 alpha (panel B), fibronectin (panel C) and TGF-$\beta$ (panel D).
Figure 6B:
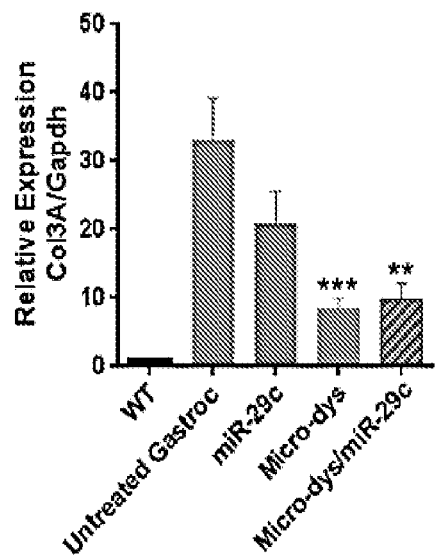
Figure 6C:
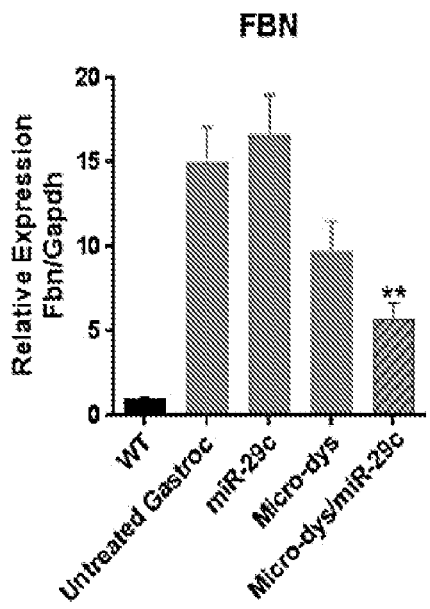

To further validate reduction of collagen observed by picrosirius red staining, qRT-PCR was performed on the muscle to quantify transcript levels of Col1A, Col3A and also another ECM component, fibronectin (Fbn). qRT-PCR analysis detected a decrease in Col1A and Col3A following each treatment, however only the cohort treated with both micro-dystrophin and miR-29c showed significant reduction (FIGS. 6a and 6b). The analysis revealed that Fbn was significantly reduced only in the co-treated cohort (FIG. 6c).

Figure 6D:
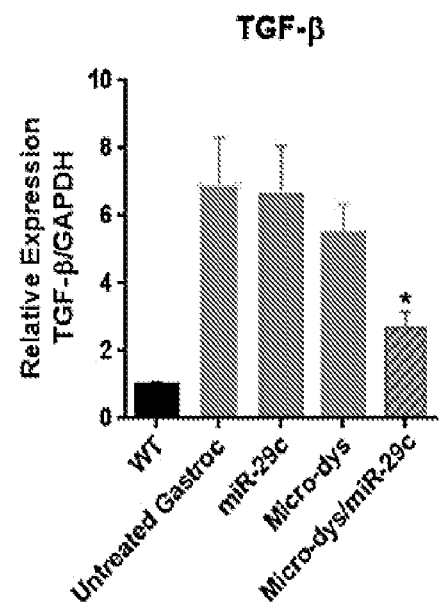

TGF-β1 has been previously shown to be up regulated in dystrophic muscle, likely playing a role in the initiation of the fibrotic cascade. TGF-β1 is a known pro-fibrotic cytokine that down regulates miR-29c and is responsible for conversion of myoblasts to myofibroblasts with an increase in collagen and muscle fibrogenesis. qRT-PCR analysis shows that co-treated muscle had significantly lower levels of TGF-β1 compared to uninjected muscle and either treatment alone (FIG. 6d). At 6 months post injection, co-treated muscle continued to show reduced Col1A, Col3A, Fbn and TGF-β1 levels, whereas only slight reductions in Col1A mRNA levels in the miR-29 and the micro-dystrophin only groups were observed An increase in specific and absolute force was observed in the muscle treated with miR-29c alone compared to the untreated limb, which when combined with micro-dystrophin led to absolute and specific force that were not significantly different than wild-type. We also observed a significant increase in gastroc weight in those muscles that were co-treated.

Initial results using rAAV.miR-29c as an anti-fibrotic therapy suggest that there is beneficial effect with reduction in collagen levels, a key contributor in fibrosis. Moreover, when combined with micro-dystrophin to improve membrane stability, miR29 up regulation normalized muscle force.

Example 6

Figure 7A:
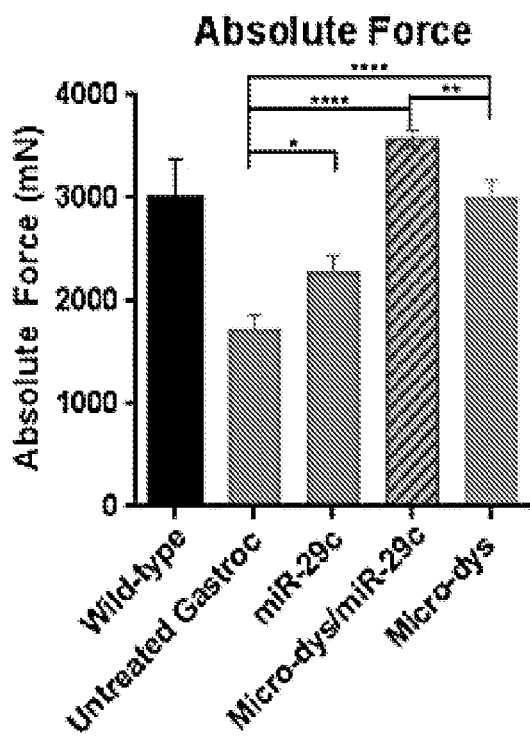
FIG. 7A-7C demonstrates the intramuscular injection of miR-29c increased absolute force (panel A), normalized specific force (panel B) and added protection from contraction-induce damage (panel C) in the muscle.
Figure 7B:
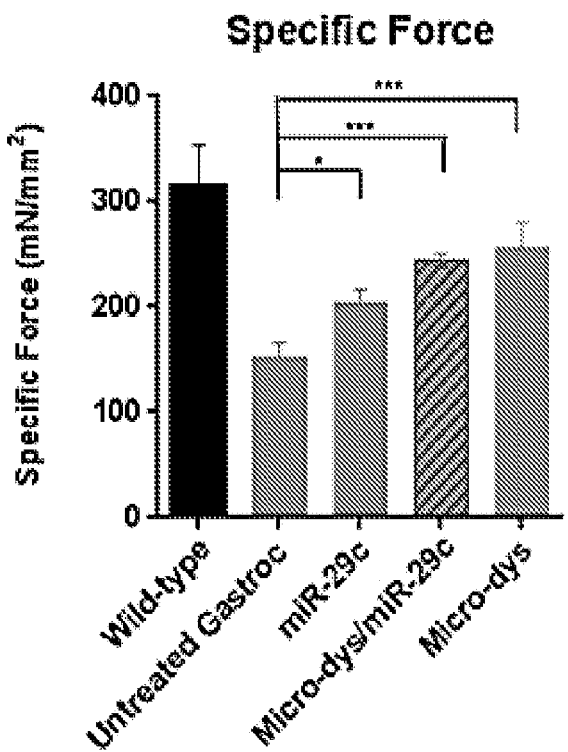

Further Increase in Absolute Force and Added Protection from Contraction-Induced Damage Knowing that miR-29-treated muscle had a modest but significant increase in absolute and specific force, the combination therapy of miR-29c overexpression and micro-dystrophin gene replacement impact on muscle function was investigated. Twelve weeks post injection, we isolated the GAS for which we performed in vivo force measurements. The rAAVrh.74.MiR-29c vector described above in Example 2 and a rAAV Co-treated rAAVrh.74.MiR-29c and rAAV expressing Micro-Dys treated GAS muscle showed significant improvement in absolute force when compared to untreated mdx/utrn$^{+/-}$ GAS muscle (co-treated—3582.4±79.4 nM vs. mdx/utrn$^{+/-}$ untreated—1722±145.7 nM vs. wild-type—3005±167.3 nM) (FIG. 7), and also normalized specific force in rAAVrh.74.miR-29c/micro-dys treated GAS muscle specific improvement when compared to untreated GAS muscle (co-treated mice-244.2±6.6 nM/mm$^2$ vs. mdx/utrn$^{+/-}$ untreated—151.6±14.5 nM/mm$^2$ vs. 312.0±34.1 nM/mm$^2$) (FIG. 7). Both absolute and specific force was not significantly different from wild-type controls.

Figure 7C:
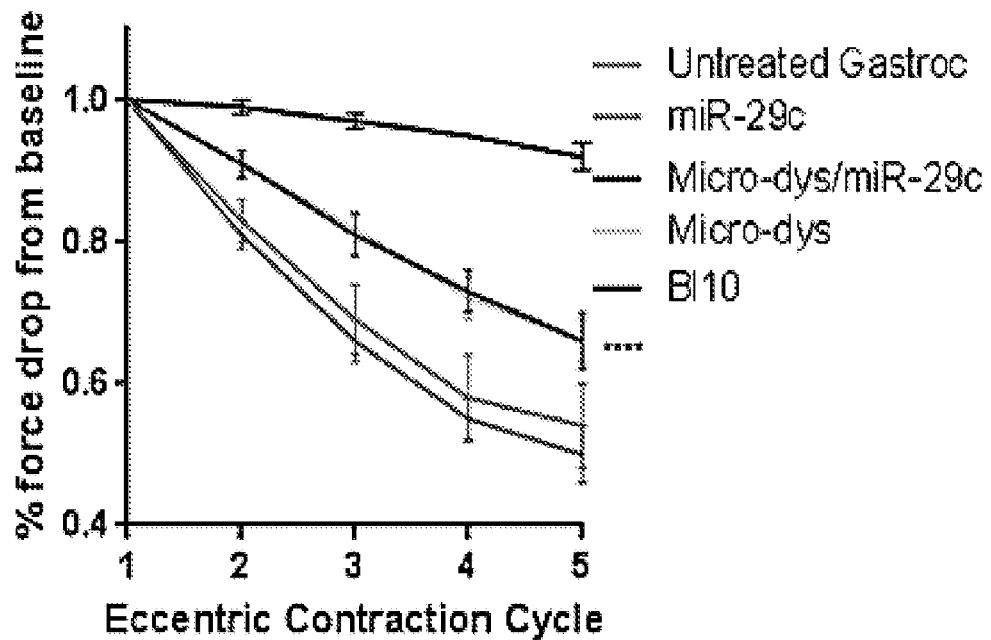

Each GAS was subjected to a series of repeated eccentric contraction. By comparing the force ratio of each contraction versus the first contraction revealed that after the fifth contraction untreated muscle decayed to 0.54±0.06 versus co-treated 0.66±0.04 (p<0.0001), which can be contributed to the micro-dystrophin since the micro-dystrophin alone also decayed to 0.66±0.04. The treated group was still significantly lower than wild-type that decayed to 0.92±0.02 (FIG. 7c). Similar findings were seen at 24 weeks post injection This data shows that reducing fibrosis and gene replacement leads to increase in both absolute and specific 5 force and significantly protects muscle from contraction-induced injury.

Example 7

Combination Treatment Increases Muscle Hypertrophy and Hyperplasia

Figure 8:
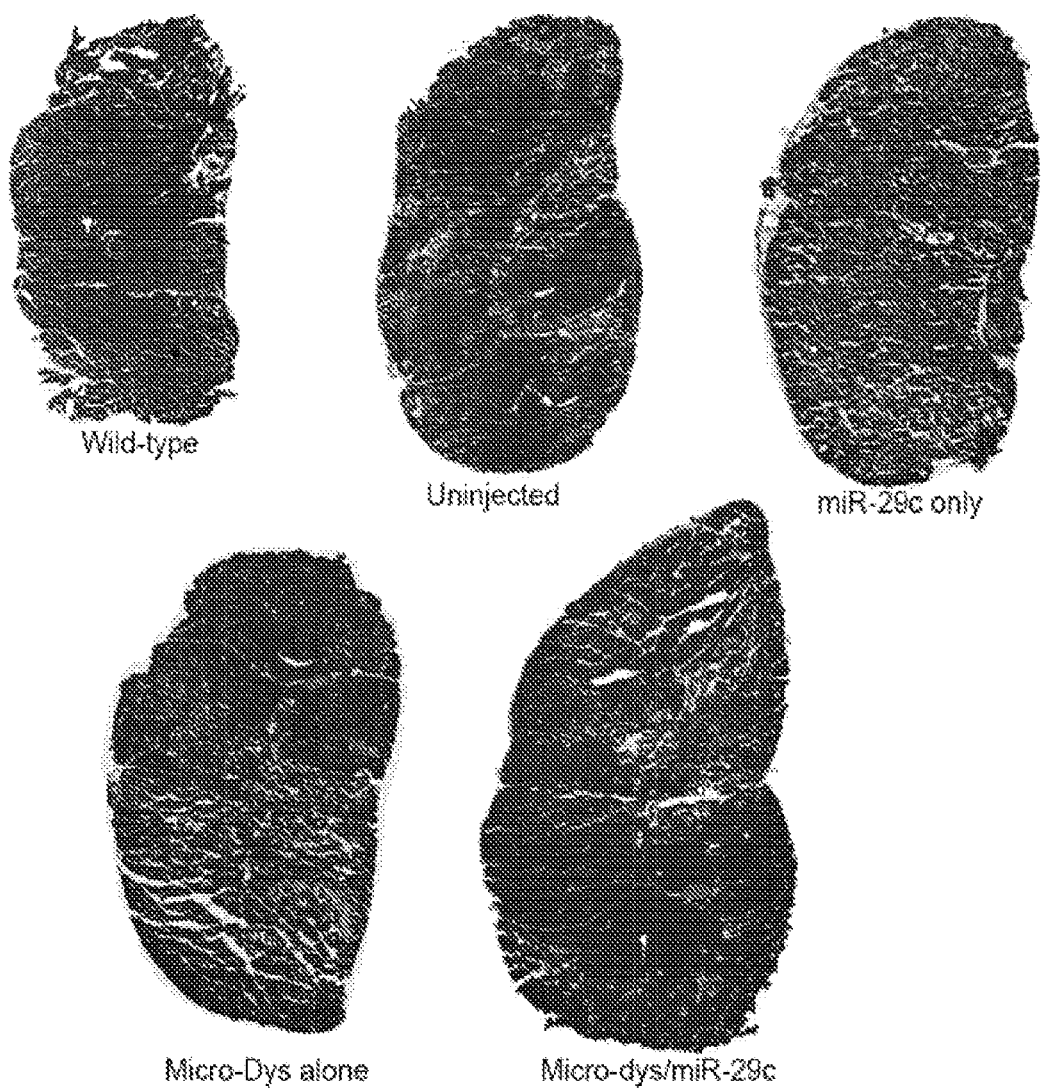
FIG. 8 illustrates that the miR-29c/$\mu$-dys combination increases muscle size in mice treated at 3 months of age.

MiR-29c co-delivered with micro-dystrophin increased the overall weight of the injected gastroc compared to either one injected alone at three months of age (FIG. 8, FIG. 9a). To investigate the source of increased muscle mass, myofiber diameters are measured. miR-29c/μ-dys combination treatment demonstrated an increase in average fiber size. Comparing mdx/utrn$^{+/-}$ controls with miR-29c/μ-dys treated mdx/utrn$^{+/-}$, the average diameter increased from 25.96 to 30.97 μm (FIG. 9b). The co-delivery produced a shift towards wild-type fiber size distribution (FIG. 9c). Although the average fiber size was increased does not explain the 30% increase in gross muscle weight. Total cross-sectional area of the muscle was also measured. Gastroc muscles from all groups were full slide scanned and the total area was measured. Muscles co-treated with micro-dys/miR-29c had a significant increase in cross sectional area compared to untreated and either treatment alone (uninjected: 24.6 vs. miR-29c: 26.3 vs. micro-dys: 26.6 vs. micro-dys/miR-29c: 33.1) (FIG. 8, FIG. 9d).

miR-29c has been reported it to play a role in the myoD/Pax7/myogenin pathway and it was hypothesized that miR-29c may be impacting regeneration and activation of satellite cells (muscle stem cells) to differentiate in myogenic lineage. To test this, the total number of muscle fibers from the full slide scanned images was counted. An increased number of muscle fibers following miR-29c/μ-dys combination treatment (FIG. 9e). Finally, given that muscle fiber diameters in mdx/utrn+/– mice are heterogeneous with many small fibers and some hypertrophic fibers, it was determined whether the number of fibers per unit area (cells/mm2) was affected with treatment. miR-29c/μ-dys combination treatment was not different than wild-type (FIG. 9f).

Example 8

Early Treatment with Combination Prevents Fibrosis

Figure 10A:
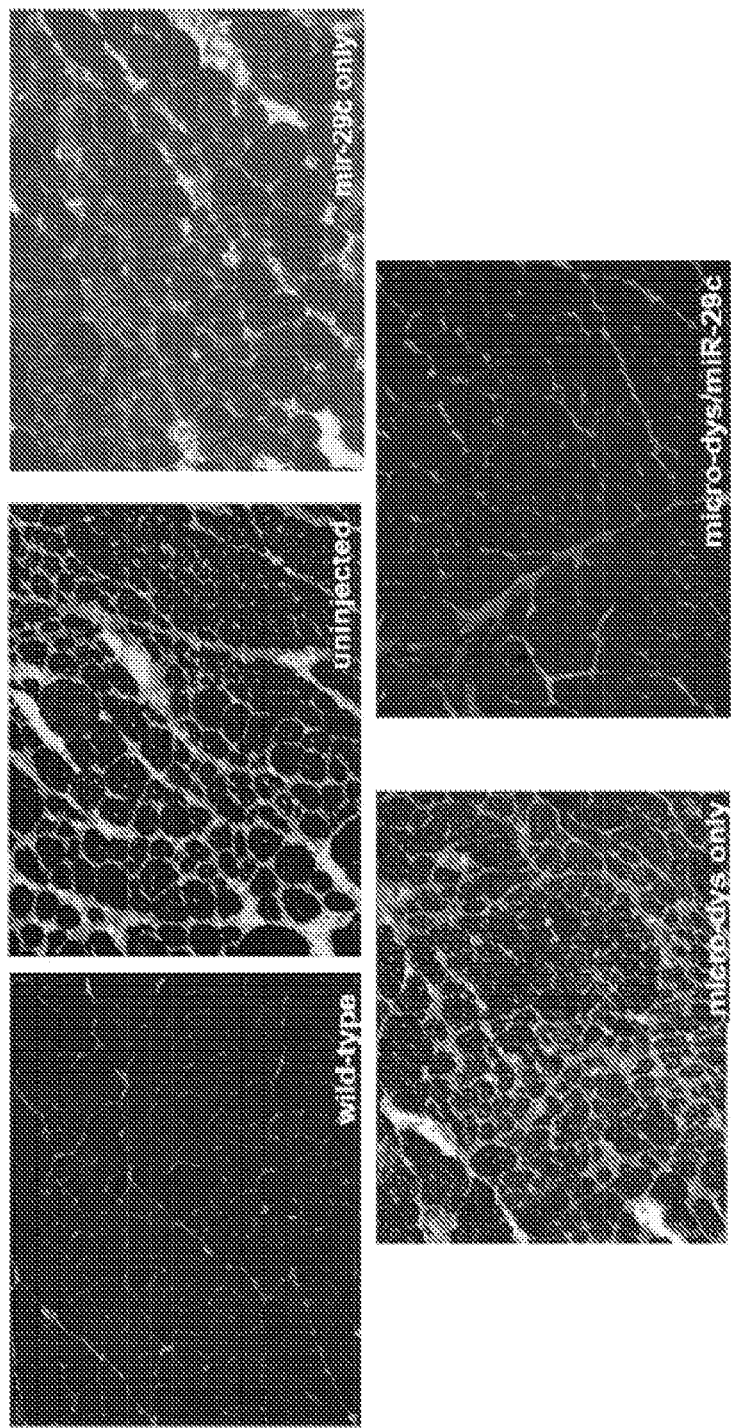
Figure 10D:
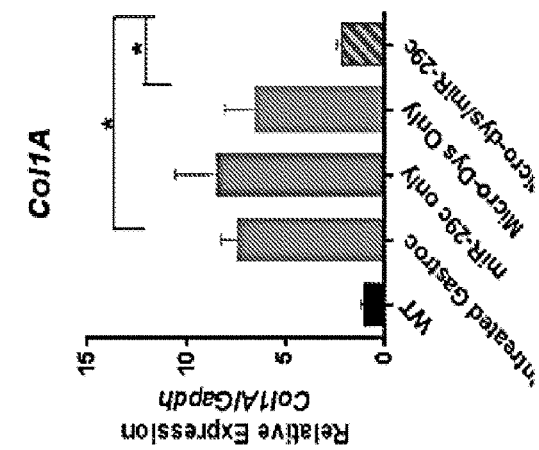
Figure 10G:
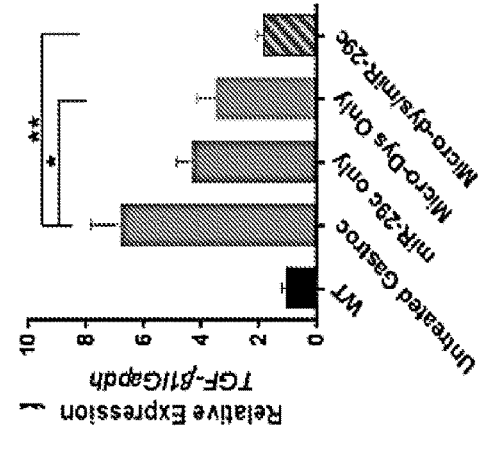
Figure 10C:
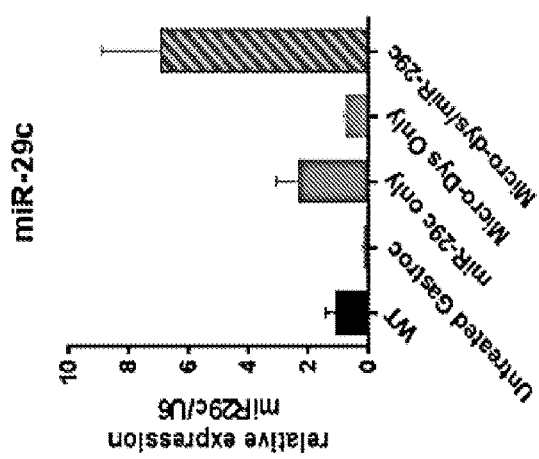
Figure 10F:
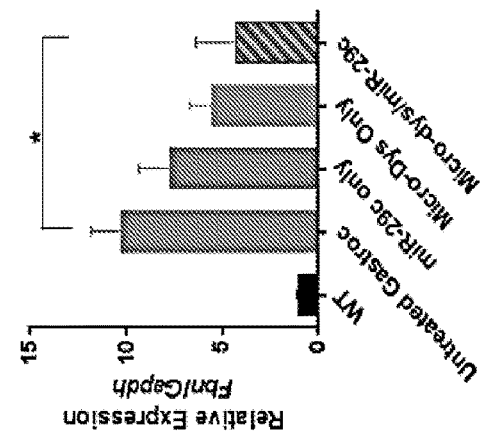
Figure 10B:
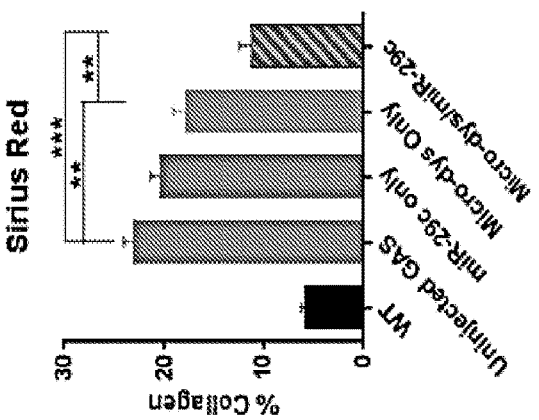
Figure 10E:
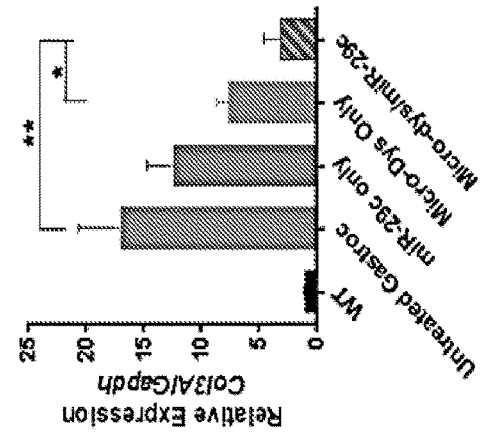

In view of the potential importance of combinatorial miR-29c and micro-dystrophin as a prophylactic therapy for DMD, a cohort of younger mdx/utrn$^{+/-}$ mice were treated at 4 weeks of age. Using the same paradigm as for other groups as described herein, the following treatments were compared for efficacy for prevention of fibrosis by intramuscular injection of GAS: scAAVrh.74.CMV.miR-29c alone, ssAAVrh74.MCK.micro-dystrophin+ scAAVrh.74.CMV.miR-29c combination therapy, or ssAAVrh74.MCK.micro-dystrophin alone at the same dose. The mice were necropsied 12 weeks post injection. A significant decrease in collagen staining throughout the GAS muscles in all treated groups compared to the untreated contralateral mdx/utrn$^{+/-}$ GAS muscle was observed (FIG. 10A). Quantification of the picrosirius red staining showed that muscle co-treated with micro-dystrophin/miR-29c had a 51% reduction in collagen compared to the untreated muscle (treated—11.32%±1.18 vs. untreated—23.15%±0.90) (p<0.0001) (FIG. 10) and qRT-PCR confirmed Col1A, Col3A, Fbn and TGF-β1 reduction following combinatorial therapy (FIGS. 10D and E).

Example 9

Early Combination Therapy Restores Force and Protects from Contraction-Induced Damage Better than Late Treatment In vivo force measurement was carried out on the GAS of the mice treated early with the combination therapy as described in Example 8. In 4-week-old mdx/utrn$^{+/-}$ mice, co-treatment using miR-29c/micro-dystrophin showed significant improvement in absolute force when compared to untreated mdx/utrn$^{+/-}$ mice and there was no difference from wild type (co-treated: 2908±129.5 mN vs. untreated: 1639.4±116.9 mN vs. wild-type: 3369.73±154.1 mN). Specific force was also normalized to wild type levels following combinatorial therapy (co-treated 338.9±22.34 mN/mm2 vs. untreated 184.3±13.42 mN/mm$^2$ vs. WT 364.3±7.79 mN/mm$^2$) (FIGS. 11A and B and 12).

Next, each GAS was subjected to a series of repeat eccentric contractions. By comparing the force ratio of each contraction by the fifth contraction, untreated muscle decayed to 0.53±0.04 versus co-treated 0.82±0.04 (p≤0.0001). The combinatorial treatment group was slightly lower than wild type but not significantly different, which decayed to 0.93±0.01 (FIG. 11C). These data show that reducing fibrosis and gene replacement lead to increase in both absolute and specific force and significantly protects muscle from contraction-induced injury.

These experiments suggest that gene replacement should be started in the newborn period. Efforts are clearly moving in the direction of identifying DMD and other muscular dystrophies in the newborn period. The Ohio Newborn Screening Study illustrates the potential for identification of DMD in newborns using CK 7 Neurol. as a biomarker (>2000 U/L) with DNA confirmation on the same dried blood spot (Mendell et al., Ann. Neurol. 71: 304-313, 2012). This methodology is now being extended to other states in the USA (PPMD May 16, 2016: Next Steps with Newborn Screening) and in other countries, particularly the UK (UK National Screening Committee) and China (Perkin Elmer™ launches screening in China).

miR-29 has also shown promise as a treatment modality for cardiac, pulmonary, and liver fibrosis. Myocardial infarction in mice and humans is associated with miR-29 down-regulation. Rooij et al. (Proc. Natl. Acad. Sci, USA 105: 13027-13032, 2008) demonstrated that exposing fibroblasts to a miR-29b mimic decreased collagen transcripts providing a path for clinical translation for cardiac fibrosis. Subsequent studies showed that in a bleomycin-induced pulmonary fibrosis mouse model, attenuation of fibrosis could be achieved using the Sleeping Beauty (SB) transposon system-based delivery of miR-29b.14. Currently, a miR-29b mimic is in a clinical Phase 1 Safety-Tolerability local intradermal trial in healthy volunteers (miRagen Therapeutics™ MRG-201). Compared to miR-29 oligonucleotide delivery that would require repeated administration related to the half-life of the oligonucleotides, AAV gene therapy could potentially provide a path for single-delivery gene transfer.

Example 10

Treatment with Muscle Specific Expression of miR-29 and Micro-Dystrophin Reduced Fibrosis and ECM Expression AAV vectors comprising the miR29c sequence and a muscle specific promoter MCK were also generated and tested as a combination therapy with AAV vectors expressing micro-dystrophin. To generate the rAAV vector, referred to herein as rAAV.MCK.miR29c, the 22 nucleotide miR29c sequence (target strand SEQ ID NO: 3 and guide strand SEQ ID NO: 4) was cloned into a miR-30 scaffold driven by a MCK promoter (SEQ ID NO: 11). The expression cassette (SEQ ID NO: 12) was cloned into a single stranded AAV plasmid and packaged using AAVrh74, a serotype known to express well in muscle. The miR-29c cDNA was synthesized using a custom primer containing the miR-29c target (sense) strand, miR-30 stem loop and miR-29c guide (antisense) strand in the miR-30 backbone. Three bases of the miR-29c sequence were modified. This sequence was then cloned into a single stranded AAV ITR containing plasmid driven by the MCK promoter and polyA sequence.

The pAAV.MCK.miR29C plasmid contains the mir29c cDNA in a miR-30 stem loop backbone flanked by AAV2 inverted terminal repeat sequences (ITR). It is this sequence that was encapsidated into AAVrh74 virions. In addition, a few nucleotides with in the miR-29c target sequence were changed to mimic Watson-crick pairing at this site as in shRNA-miR(luc). According to ShRNA-luc design, the hairpin should be perfectly complementary throughout its length. Plus, the more changes to the passenger strand, the more likely the elimination of any endogenous mechanism that regulates miR-29 processing that could recognize the miRNA via the stem. The $19^{th}$ base of the guide strand was modified to a cytosine to mimic the nucleotide that precedes the cleavage site in natural mi-29c sequence and the corresponding base on the other strand was changed to preserve pairing.

Figure 13A:
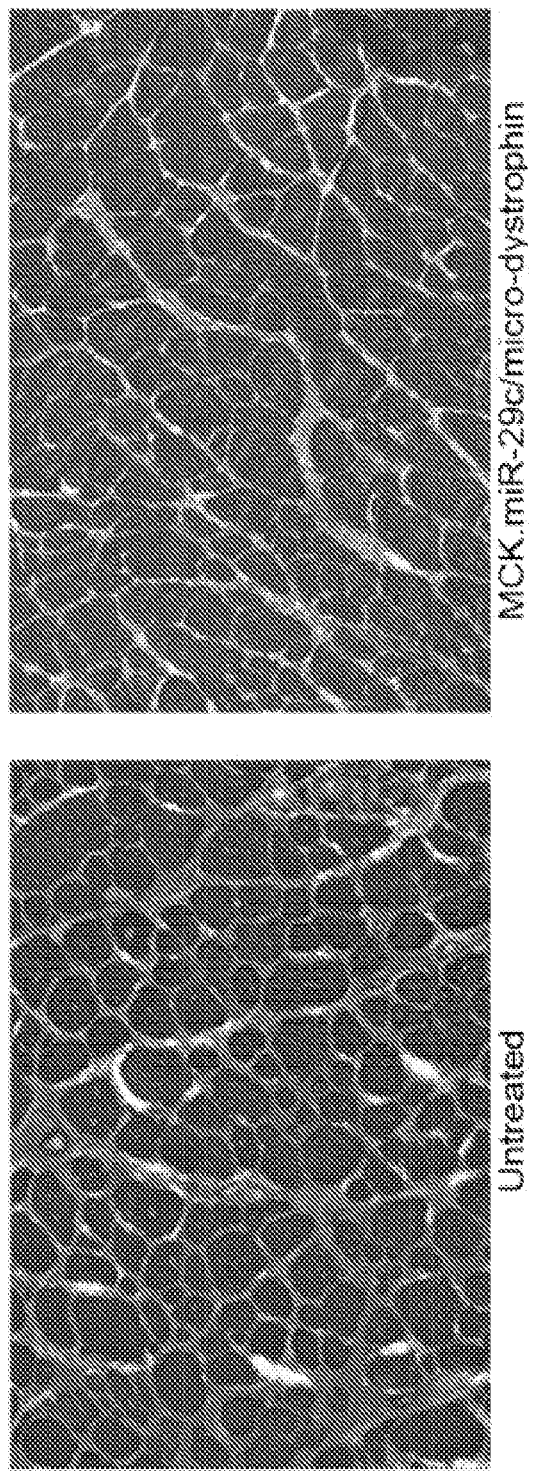
Figure 14A:
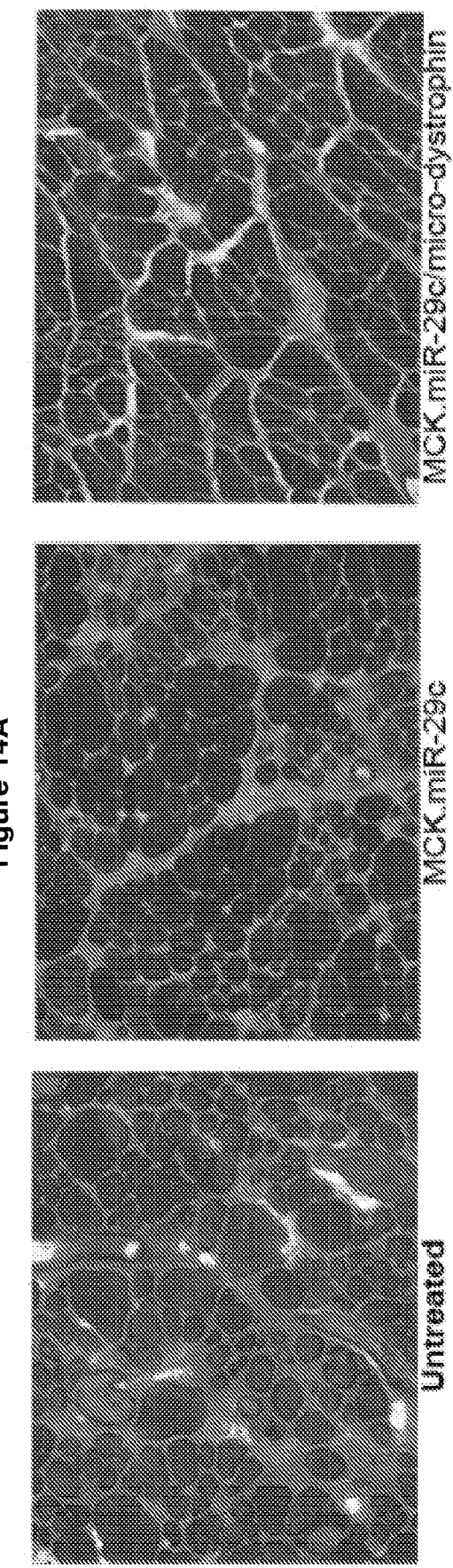

Early treatment of AAV.MCK.miR-29c/micro-dystrophin combination therapy was more effective at reducing fibrosis and ECM expression. 4-5-week-old mdx/utrn$^{+/-}$ mice received an intramuscular injection of rAAVrh.74.MCK.MiR-29c and rAAVrh74.MCK.micro-dystrophin at $5 \times 10^{11}$ vgs to the left gastrocnemius muscle as described in Example 5. The muscles were harvested twelve weeks post injection. Picrosirius red staining of muscle harvested from uninjected and mice injected with combination therapy of rAAV.MCK.miR-29c/rAAV.MCK.micro-dystrophin showed co-treated muscle had a 50.9% reduction in collagen compared to untreated GAS muscle (See FIGS. 13a and 13b). qRT-PCR confirmed an increase in miR-29c transcript levels in the treated cohort (FIG. 13c). Semi-quantitative qRT-PCR showed a significant reduction in Collagen A1 and Collagen 3A (FIG. 13d, e), Fibronectin (FIG. 13f) and Tgfβ1 (FIG. 13g) levels in the AAV.MCK.miR-29c/AAV.micro-dystrophin treated muscle compared to the contralateral limb therapies. (*p<0.05,**p<0.0001). Late treatment of AAV.MCK.miR-29c/micro-dystrophin combination therapy is effective at reducing fibrosis and ECM expression. Three month old mdx/utrn$^{+/-}$ mice received an intramuscular injection of rAAVrh.74.MCK.MiR-29c and rAAVrh.74.MCK.micro-dystrophin at $5 \times 10^{11}$ vgs to the left gastrocnemius muscle as described in Example 5. The muscles were harvested twelve weeks post injection. Picrosirius red staining of untreated, AAV.MCK.miR-29c and AAV.MCK.miR-29c/AAV.micro-dystrophin treated muscle showed co-treated muscle had a 30.3% reduction in collagen compared to untreated GAS muscle (See FIGS. 14a and 14b) qRT-PCR confirmed an increase in miR-29c transcript levels in the treated cohorts (FIG. 14c). Semi-quantitative qRT-PCR shows a significant reduction in Collagen 1A and Collagen 3A (FIG. 14d, e), Fibronectin (FIG. 14f) and Tgfβ1 (FIG. 14G) levels in the AAV.miR-29c/AAV.micro-dystrophin treated muscle compared to the contralateral limb. One-way ANOVA. All data represent mean±SEM. (p<0.01, ****p<0.0001).

Example 11

Early Combination Therapy Restores Force and Protects from Contraction-Induced Damage Better than Late Treatment In vivo force measurement was carried out on the GAS of the mice treated early with the muscle-specific expression of miR-29 and micro-dystrophin. as described in Examples 8 and 9. In 4-week-old mdx/utrn$^{+/-}$ mice, co-treatment using rAAV.MCK.miR-29c/and rAAV expressing micro-dystrophin showed significant improvement in absolute force when compared to untreated mdx/utrn$^{+/-}$ mice and there was no difference from wild type (FIG. 15a). Specific force was also normalized to wild type levels following combination therapy (FIG. 15b).

Muscles were then assessed for loss of force following repetitive eccentric contractions as described in Example 9. Mice co-treated with rAAV.MCK.miR-29c/rAAV.MCK.micro-dystrophin and rAAV.MCK.micro-dystrophin alone showed a protection from loss of force compared with untreated mdx/utrn$^{+/-}$ muscles (FIG. 15c).

In 12-week-old mdx/utrn$^{+/-}$ mice, co-treatment using rAAV.MCK.miR-29c/and rAAV expressing micro-dystrophin restored force and protected against contraction-induced damage. Measurement of absolute (FIG. 16a) and normalized specific force (FIG. 16b) following tetanic contraction rAAV.MCK.miR-29c and rAAV expressing micro-dystrophin injected GAS muscles were significantly increased compared to untreated mdx/utrn$^{+/-}$ muscle. Subsequently, muscles were assessed for loss of force following repetitive eccentric contractions as described in Example 9. Mice co-treated with MCK.miR-29c/micro-dystrophin showed a protection from loss of force compared with untreated mdx/utrn$^{+/-}$ muscles (FIG. 16c). These data show that reducing fibrosis and gene replacement lead to increase in both absolute and specific force and significantly protects muscle from contraction-induced injury.

Example 12

Early Combination Treatment Increases Muscle Hypertrophy and Hyperplasia

Figure 17A:
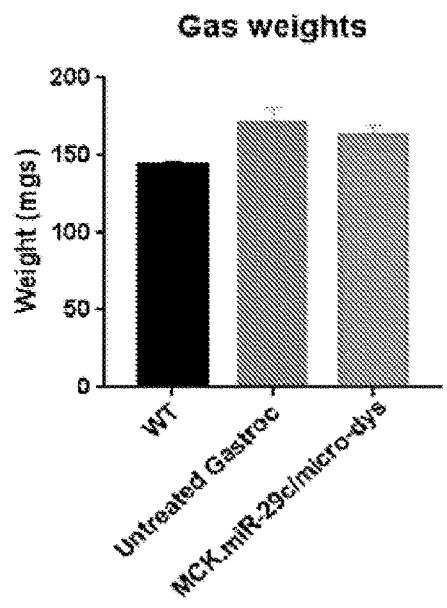
Figure 17B:
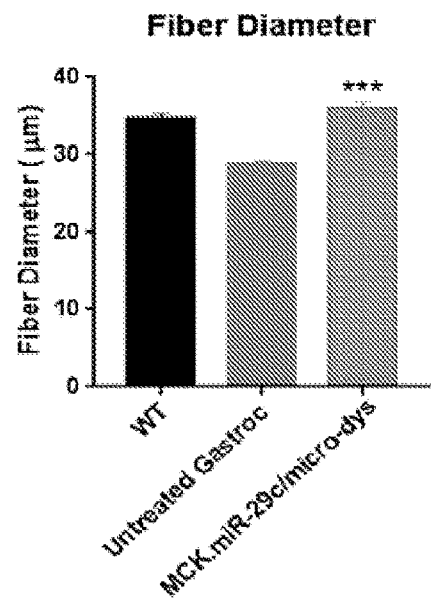
Figure 17C:
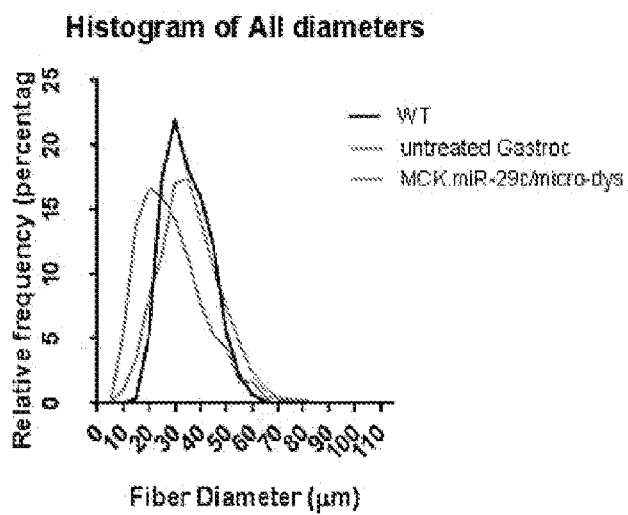
Figure 17D:
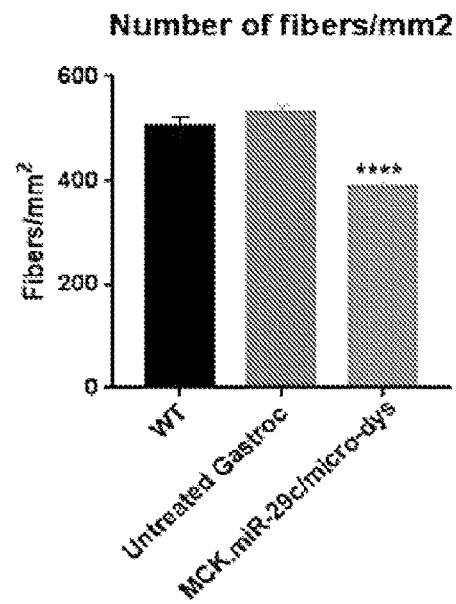

Co-delivery of rAAV.MCK.miR-29 with rAAV expressing micro-dystrophin did not increase overall weight of the injected gastroc compared to either one injected alone at three months post-injection (FIG. 17a). Myofiber diameters were also measured. miR-29c/micro-dystrophin combination treatment demonstrated an increase in average fiber size. Comparing mdx/utrn$^{+/-}$ controls with miR-29c/micro-dystrophin treated mdx/utrn$^{+/-}$, the average diameter increased from 28.96 to 36.03 μm (FIG. 17b). The co-delivery produced a shift towards wild-type fiber size distribution (FIG. 17c). The number of muscle fibers per mm$^2$ in the miR-29c/micro-dystrophin combination treatment was significantly less than untreated mice and wild-type (FIG. 17d; *p<0.01, **p<0.0001).

REFERENCES

1. Hoffman, E. P., Brown, R. H., Jr. & Kunkel, L. M. Dystrophin: the protein product of the Duchenne muscular dystrophy locus. *Cell* 51, 919-928 (1987).
2. Straub, V. & Campbell, K. P. Muscular dystrophies and the dystrophin-glycoprotein complex. *Curr Opin Neurol* 10, 168-175 (1997).
3. Sacco, A., et al. Short telomeres and stem cell exhaustion model Duchenne muscular dystrophy in mdx/mTR mice. *Cell* 143, 1059-1071 (2010).
4. Wallace, G. Q. & McNally, E. M. Mechanisms of muscle degeneration, regeneration, and repair in the muscular dystrophies. *Annu Rev Physiol* 71, 37-57 (2009).
5. Zhou, L. & Lu, H. Targeting fibrosis in Duchenne muscular dystrophy. *J Neuropathol Exp Neurol* 69, 771-776 (2010).
6. Desguerre, I., et al. Endomysial fibrosis in Duchenne muscular dystrophy: a marker of poor outcome associated with macrophage alternative activation. *J Neuropathol Exp Neurol* 68, 762-773 (2009).
7. Kim, J., et al. microRNA-directed cleavage of ATHB15 mRNA regulates vascular development in *Arabidopsis* inflorescence stems. *Plant J* 42, 84-94 (2005).
8. Ambros, V. MicroRNA pathways in flies and worms: growth, death, fat, stress, and timing. *Cell* 113, 673-676 (2003).
9. Eisenberg, I., et al. Distinctive patterns of microRNA expression in primary muscular disorders. *Proc Natl Acad Sci USA* 104, 17016-17021 (2007).
10. Jiang, X., Tsitsiou, E., Herrick, S. E. & Lindsay, M. A. MicroRNAs and the regulation of fibrosis. *FEBS J* 277, 2015-2021 (2010).
11. van Rooij, E., et al. Dysregulation of microRNAs after myocardial infarction reveals a role of miR-29 in cardiac fibrosis. *Proc Natl Acad Sci USA* 105, 13027-13032 (2008).
12. Cacchiarelli, D., et al. MicroRNAs involved in molecular circuitries relevant for the Duchenne muscular dystrophy pathogenesis are controlled by the dystrophin/nNOS pathway. *Cell Metab* 12, 341-351 (2010).
13. DiPrimio, N., McPhee, S. W. & Samulski, R. J. Adeno-associated virus for the treatment of muscle diseases: toward clinical trials. *Curr Opin Mol Ther* 12, 553-560 (2010).
14. Mendell, J. R., et al. Sustained alpha-sarcoglycan gene expression after gene transfer in limb-girdle muscular dystrophy, type 2D. *Ann Neurol* 68, 629-638 (2010).
15. Mendell, J. R., et al. Limb-girdle muscular dystrophy type 2D gene therapy restores alpha-sarcoglycan and associated proteins. *Ann Neurol* 66, 290-297 (2009).
16. Mendell, J. R., et al. A phase ½a follistatin gene therapy trial for becker muscular dystrophy. *Molecular therapy: the journal of the American Society of Gene Therapy* 23, 192-201 (2015).
17. Carnwath, J. W. & Shotton, D. M. Muscular dystrophy in the mdx mouse: histopathology of the soleus and extensor digitorum longus muscles. *J Neurol Sci* 80, 39-54 (1987).
18. Coulton, G. R., Morgan, J. E., Partridge, T. A. & Sloper, J. C. The mdx mouse skeletal muscle myopathy: I. A histological, morphometric and biochemical investigation. *Neuropathol Appl Neurobiol* 14, 53-70 (1988).
19. Cullen, M. J. & Jaros, E. Ultrastructure of the skeletal muscle in the X chromosome-linked dystrophic (mdx) mouse. Comparison with Duchenne muscular dystrophy. *Acta Neuropathol* 77, 69-81 (1988).
20. Dupont-Versteegden, E. E. & McCarter, R. J. Differential expression of muscular dystrophy in diaphragm versus hindlimb muscles of mdx mice. *Muscle Nerve* 15, 1105-1110 (1992).
21. Stedman, H. H., et al. The mdx mouse diaphragm reproduces the degenerative changes of Duchenne muscular dystrophy. *Nature* 352, 536-539 (1991).
22. Deconinck, A. E., et al. Utrophin-dystrophin-deficient mice as a model for Duchenne muscular dystrophy. *Cell* 90, 717-727 (1997).
23. Grady, R. M., et al. Skeletal and cardiac myopathies in mice lacking utrophin and dystrophin: a model for Duchenne muscular dystrophy. *Cell* 90, 729-738 (1997).
24. Love, D. R., et al. An autosomal transcript in skeletal muscle with homology to dystrophin. *Nature* 339, 55-58 (1989).
25. Tinsley, J. M., et al. Primary structure of dystrophin-related protein. *Nature* 360, 591-593 (1992).
26. Tinsley, J., et al. Expression of full-length utrophin prevents muscular dystrophy in mdx mice. *Nat Med* 4, 1441-1444 (1998).
27. Squire, S., et al. Prevention of pathology in mdx mice by expression of utrophin: analysis using an inducible transgenic expression system. *Hum Mol Genet* 11, 3333-3344 (2002).
28. Rafael, J. A., Tinsley, J. M., Potter, A. C., Deconinck, A. E. & Davies, K. E. Skeletal muscle-specific expression of a utrophin transgene rescues utrophin-dystrophin deficient mice. *Nat Genet* 19, 79-82 (1998).

29. Zhou, L., et al. Haploinsufficiency of utrophin gene worsens skeletal muscle inflammation and fibrosis in mdx mice. *J Neurol Sci* 264, 106-111 (2008).
30. Gutpell, K. M., Hrinivich, W. T. & Hoffman, L. M. Skeletal Muscle Fibrosis in the mdx/utrn+/− Mouse Validates Its Suitability as a Murine Model of Duchenne Muscular Dystrophy. *PloS one* 10, e0117306 (2015).
31. Rodino-Klapac, L. R., et al. Micro-dystrophin and follistatin co-delivery restores muscle function in aged DMD model. *Human molecular genetics* 22, 4929-4937 (2013).
32. Cushing, L., et al. MIR-29 is a Major Regulator of Genes Associated with Pulmonary Fibrosis. *Am J Respir Cell Mol Biol* (2010).
33. Roderburg, C., et al. Micro-RNA profiling reveals a role for miR-29 in human and murine liver fibrosis. *Hepatology* 53, 209-218 (2011).
34. Nevo, Y., et al. The Ras antagonist, farnesylthiosalicylic acid (FTS), decreases fibrosis and improves muscle strength in dy/dy mouse model of muscular dystrophy. *PloS one* 6, e18049 (2011).
35. Rodino-Klapac, L. R., et al. A translational approach for limb vascular delivery of the micro-dystrophin gene without high volume or high pressure for treatment of Duchenne muscular dystrophy. *J Transl Med* 5, 45 (2007).
36. Mulieri, L. A., Hasenfuss, G., Ittleman, F., Blanchard, E. M. & Alpert, N. R. Protection of human left ventricular myocardium from cutting injury with 2,3-butanedione monoxime. *Circ Res* 65, 1441-1449 (1989).
37. Rodino-Klapac, L. R., et al. Persistent expression of FLAG-tagged micro dystrophin in nonhuman primates following intramuscular and vascular delivery. *Molecular therapy: the journal of the American Society of Gene Therapy* 18, 109-117 (2010).
38. Grose, W. E., et al. Homologous recombination mediates functional recovery of dysferlin deficiency following AAV5 gene transfer. *PloS one* 7, e39233 (2012).
39. Liu, M., et al. Adeno-associated virus-mediated microdystrophin expression protects young mdx muscle from contraction-induced injury. *Mol Ther* 11, 245-256 (2005).

What is claimed:

1. A method of reducing or preventing fibrosis in a subject suffering from muscular dystrophy or dystrophinopathy comprising administering i) a therapeutically effective amount of recombinant AAVrh74 vector expressing miR-29c and ii) a therapeutically effective amount of recombinant AAVrh74 vector expressing micro-dystrophin.

2. A method of claim 1 wherein the muscular dystrophy is Duchenne muscular dystrophy or Becker muscular dystrophy.

3. The method of claim 1 wherein the recombinant AAV vector or the composition is administered by intramuscular administration, intravenous injection, parental administration or systemic administration.

4. The method of claim 1 the recombinant AAV vector expressing miR-29 is administered before fibrosis is observed in the subject or before muscle force is reduced in the subject or before muscle mass is reduced in the subject.

5. The method of claim 1 wherein the recombinant AAV vector expressing micro-dystrophin is administered before fibrosis is observed in the subject or before muscle force is reduced in the subject or before muscle mass is reduced in the subject.

6. The method of claim 1 wherein the recombinant AAV vector expressing miR-29c comprises
   a) the nucleotide sequences of SEQ ID NO: 3 and SEQ ID NO: 4,
   b) the nucleotide sequence of SEQ ID NO: 2,
   c) the nucleotide sequence of SEQ ID NO: 1 or
   d) the nucleotide sequence of SEQ ID NO: 12.

7. The method of claim 1 wherein the recombinant AAV vector expressing micro-dystrophin comprises
   a) a nucleotide sequence having at least 85% identity to the nucleotide sequence SEQ ID NO: 7 and encodes a functional micro-dystrophin protein,
   b) the nucleotide sequence of SEQ ID NO: 7, or
   c) the nucleotide sequence of SEQ ID NO: 9.

8. The method of claim 1 wherein the nucleotide sequence encoding the miR-29c or the nucleotide sequence encoding a functional micro-dystrophin is operably linked to a muscle-specific control element or an ubiquitous promoter.

9. The recombinant AAV vector of claim 8 wherein the muscle-specific control element comprises the nucleotides 236 to 799 of SEQ ID NO: 9.

* * * * *